(12) United States Patent
Ong

(10) Patent No.: US 12,144,817 B2
(45) Date of Patent: *Nov. 19, 2024

(54) TESTOSTERONE ESTER TRIGLYCERIDE FORMULATIONS

(71) Applicant: Antares Pharma, Inc., Ewing, NJ (US)

(72) Inventor: Shaowei Ong, Ewing, NJ (US)

(73) Assignee: Antares Pharma, Inc., Ewing, NJ (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/405,984

(22) Filed: Aug. 18, 2021

(65) Prior Publication Data

US 2022/0079955 A1  Mar. 17, 2022

Related U.S. Application Data

(63) Continuation of application No. 16/847,067, filed on Apr. 13, 2020, now Pat. No. 11,123,352, which is a continuation of application No. 16/117,963, filed on Aug. 30, 2018, now Pat. No. 10,646,495.

(60) Provisional application No. 62/552,190, filed on Aug. 30, 2017.

(51) Int. Cl.
| | |
|---|---|
| *A61K 47/44* | (2017.01) |
| *A61K 9/00* | (2006.01) |
| *A61K 9/10* | (2006.01) |
| *A61K 9/107* | (2006.01) |
| *A61K 31/5685* | (2006.01) |
| *A61K 47/14* | (2017.01) |

(52) U.S. Cl.
CPC ........ *A61K 31/5685* (2013.01); *A61K 9/0019* (2013.01); *A61K 9/10* (2013.01); *A61K 9/107* (2013.01); *A61K 47/14* (2013.01); *A61K 47/44* (2013.01)

(58) Field of Classification Search
CPC .... A61K 31/5685; A61K 9/0019; A61K 9/10; A61K 9/107; A61K 47/14; A61K 47/44
See application file for complete search history.

(56) References Cited

U.S. PATENT DOCUMENTS

| 6,090,800 A | 7/2000 | Unger et al. |
| 2008/0317844 A1 | 12/2008 | Dudley |
| 2013/0225544 A1 | 8/2013 | Nachaegari et al. |
| 2016/0175572 A1 | 6/2016 | Crowley et al. |

FOREIGN PATENT DOCUMENTS

| JP | 2008537960 A | 10/2008 |
| JP | 2011-519846 A | 7/2011 |
| JP | 2013-516433 A | 5/2013 |
| JP | 2015516845 A | 6/2015 |
| WO | 2011063774 A2 | 6/2011 |
| WO | 2011082384 A2 | 7/2011 |

OTHER PUBLICATIONS

European Search Report and Written Opinion for EP 18851108.3; dated Apr. 22, 2021; 22 pages.
Samyn Pieter et al: "Quality and Statistical Classification of Brazilian Vegetable Oils Using Mid-Infrared and Raman Spectroscopy", Applied Spectroscopy., vol. 66, No. 5, May 1, 2012, 552-565, XP055785485, US ISSN: 0003-7028, DOI: 10.1366/11-06484.
Salam Darine A. et al: "Effect of Butylated Hydroxytoluene (BHT) on the Aerobic Biodegradation of a Model Vegetable Oil in Aquatic Media", Environmental Science & Technology, vol. 46, No. 12, Jun. 11, 2012, 6798-6805, XP055785505, US ISSN: 0013-936X, DOI: 10.1021 / es2046712 Retrieved from the Internet: URL:https://pubs.acs.org/doi/pdf/10.1021 /es2046712.
Himoudy Iman: "Preservatives and their role in Pharma and Clinical Research", Int. J. Pharm. Sci & Scient Res., vol. 2, No. 4, Sep. 29, 2016, 134-151, XP055785568, Retrieved from the Internet: URL:https://biocoreopen.org/ijpsr/Preservatives-and-their-role-in-Pharma-and-Cli n ical-Research. php.
Florey Klaus: "Testosterone Enanthate", Analytical Profiles of Drug Substances vol. 4, 1975, vol. 4, Jan. 1, 1975, 452-465, XP055785587, Retrieved from the Internet: URL:https:// www.sciencedirect.com/science/article/pil/S0099542808600234 ?via=ihub.
Srinivas-Shankar Upendram et al: "Drug Insight: testosterone preparations", Nature Clinical Practice Urology, vol. 3, No. 12, Dec. 1, 2006, 653-665, XP055785612, GB ISSN: 1743-4270, DOI: 10.1038/ncpuro0650 Retrieved from the Internet: URL:http://www.nature.com/articles/ncpuro0650.pdf.
International Search Report mailed Dec. 18, 2018, in connection with International Patent Application No. PCT/US2018/048856 (4 pages).
Written Opinion mailed Dec. 18, 2018, in connection with International Patent Application No. PCT/US2018/048856 (6 pages).
Irby et al. "Lipid-Drug Conjugate for Enhancing Drug Delivery", Molecular Pharmaceutics, 2017, vol. 14, pp. 1325-1338. [Published Jan. 12, 2017) p. 1326, Figure 1C; p. 1330, Figure 4b (14 pages).
Jain et al. "Steroid-Coupled liposomes for Targeted Delivery to Tumors", Therapeutic Delivery, 2010, vol. 1(2), pp. 345-357, p. 353, Figure 3 (13 pages).
Centrafoods—Product Specifications, Jan. 22, 2012 (Jan. 22, 2012) p. 1 (1 page).
Jokic et al., "Fatty Acid Composition of Oil Obtained from Soybeans by Extraction with Supercritical Carbon Dioxide". Czech. J. Food Sci., vol. 31, pp. 116-125 (Year:2013).
Canadian Office Action dated Apr. 7, 2021 for Canadian Patent Application No. 3,072,198, 4 pages.
Office Action mailed Oct. 14, 2021, in connection with Canadian Patent Application No. 3,072,198 (3 pages).
Extended European Search Reported mailed Oct. 14, 2021 in connection with European Patent Application No. 18851108.3 (25 pages).

(Continued)

*Primary Examiner* — Barbara P Badio
(74) *Attorney, Agent, or Firm* — Morgan, Lewis & Bockius LLP

(57) ABSTRACT

Testosterone ester triglyceride formulations, optionally further including adducts. Methods of in-situ control of the manufacture or formation of such adducts are also described.

16 Claims, 46 Drawing Sheets

(56) References Cited

OTHER PUBLICATIONS

Craig, Christine M., "Xyosted (testosterone enanthate) Injection," Product Quality Reviews, May 30, 2017, pp. 1-62, https://www.accessdata.fda.gov/drugsatfda_docs/nda/2019/209863Orig1s000ChemR.pdf.
Vesper, Anne-Rose, "Synthesis of novel C2-symmetric testosterone dimers and evaluation of antiproliferative activity on androgen-dependent and -independent prostate cancer cell lines," Steroids, 2016, 115:98-104.
Notification of Reasons for Rejection for Japanese Patent Application No. 2022-007070, dated Feb. 21, 2023, 12 pages.
Examination Report issued in European Application No. 18851108.3, dated Aug. 30, 2023, 7 pages.
Decision of Rejection for Japanese Patent Application No. 2022-007070 mailed Sep. 19, 2023, 6 pages.
Office Action issued in Canadian Patent Application No. 3,177,229, dated Feb. 8, 2024, 4 pages.
Final Japanese Office Action for related Japanese Patent Application No. 2022-007070, mailed Apr. 1, 2024, 3 pages.

TESTOSTERONE ESTER TRIGLYCERIDE FORMULATIONS

CROSS REFERENCE TO RELATED APPLICATIONS

This application claims the benefit of U.S. Provisional Patent Application No. 62/552,190, filed on Aug. 30, 2017, which is incorporated by reference in its entirety.

FIELD OF THE INVENTION

The invention relates generally to testosterone ester triglyceride formulations.

BACKGROUND OF THE INVENTION

Testosterone is the primary male sex hormone and an anabolic steroid. In men, testosterone plays a key role in the development of male reproductive tissues such as the testis and prostate, and promotes secondary sexual characteristics such as increased muscle and bone mass, and the growth of body hair. Testosterone enanthate is the heptanoic acid derived ester of testosterone, and thus a prodrug of testosterone. Testosterone enanthate is less polar than free testosterone, and affords a sustained in vivo delivery of testosterone upon parenteral administration, by being slowly absorbed from the lipid phase. Thus testosterone enanthate can be administered at longer time intervals, for example one to four weeks.

SUMMARY OF THE INVENTION

In one embodiment, the invention relates to a pharmaceutical formulation including a testosterone ester of Formula 1, an antioxidant, and a pharmaceutically acceptable carrier including one or more triglycerides of Formula 2:

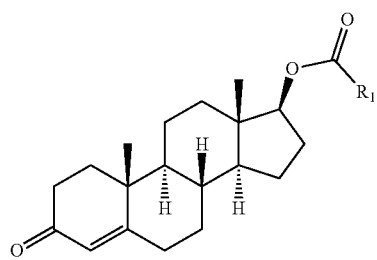

Formula 1

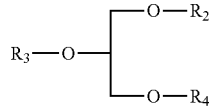

Formula 2 wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and stearic acid. In some embodiments, $R_1$ is propyl, butyl, pentyl, hexyl, heptyl, octyl, nonyl, decyl, undecyl, dodecyl, cyclopentylethyl, or unsaturated analogs thereof. In some embodiments, the testosterone ester is testosterone enanthate, testosterone cipionate, testosterone propionate, or testosterone undecanoate. In some embodiments, the pharmaceutical formulation is for parenteral administration. In some embodiments, the testosterone ester is testosterone enanthate. In some embodiments, the triglyceride is one of LLL, OLL, OOL, OOO, PLL, POL, POO, or SOL. In some embodiments, the pharmaceutically acceptable carrier includes a vegetable oil. In some embodiments, the vegetable oil is sesame oil. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium.

In one embodiment, the invention relates to a pharmaceutical formulation including testosterone enanthate, sesame oil, and BHT. In one embodiment, the invention relates to a pharmaceutical formulation including testosterone enanthate, sesame oil, and tocopherol. In some embodiments, the pharmaceutical formulation is for parenteral administration.

In one embodiment, the invention relates to a testosterone ester adduct of Formula 3:

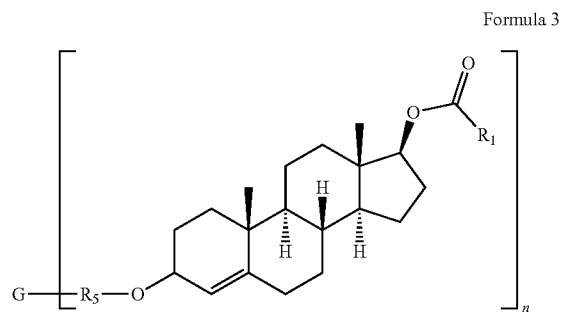

Formula 3 wherein $R_1$ is an alkyl or alkenyl substituent which can be the same or different at each independent occurrence, $R_5$ is an acyl group corresponding to an unsaturated fatty acid, G is a glycerol, monoglyceride, or diglyceride residue, n is 1, 2, or 3, and the testosterone residue is connected to an allylic or doubly allylic carbon of $R_5$. In some embodiments, the testosterone ester adduct has Formula 4. In some embodiments, $R_1$ is one of propyl, butyl, pentyl, hexyl, heptyl, octyl, nonyl, decyl, undecyl, dodecyl, cyclopentylethyl, and/or unsaturated analogs thereof. In some embodiments, $R_1$ is hexyl.

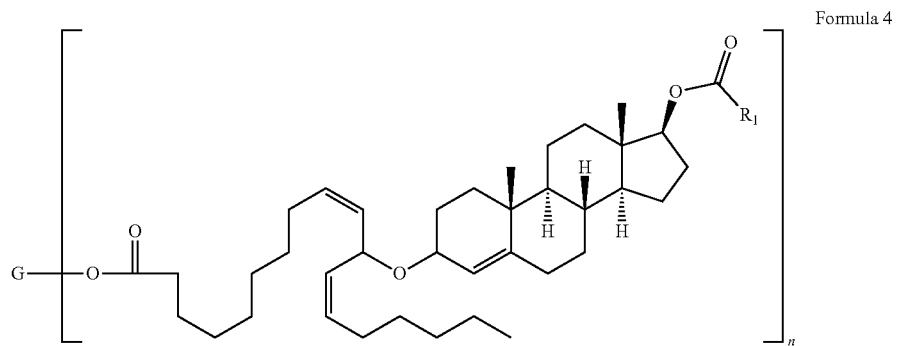
Formula 4
In some embodiments, the invention relates to a testosterone ester adduct of any one of Formulas 5 to 9:
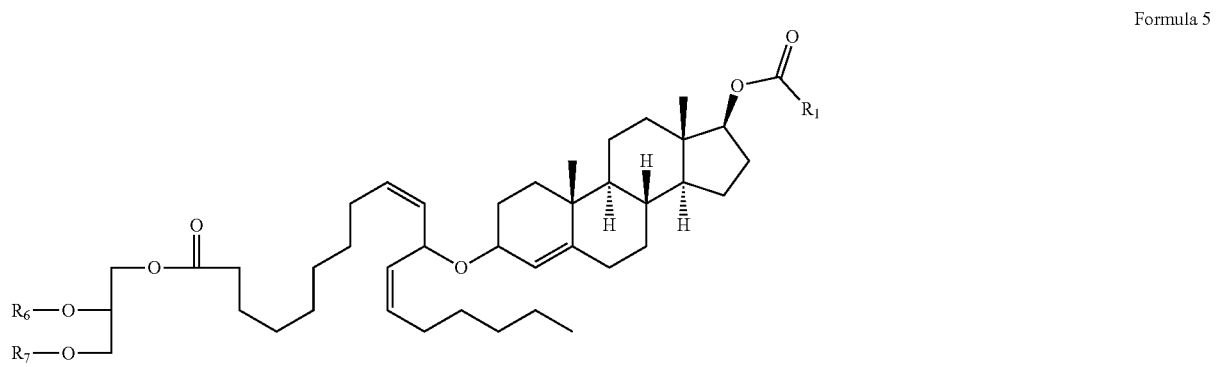
Formula 5
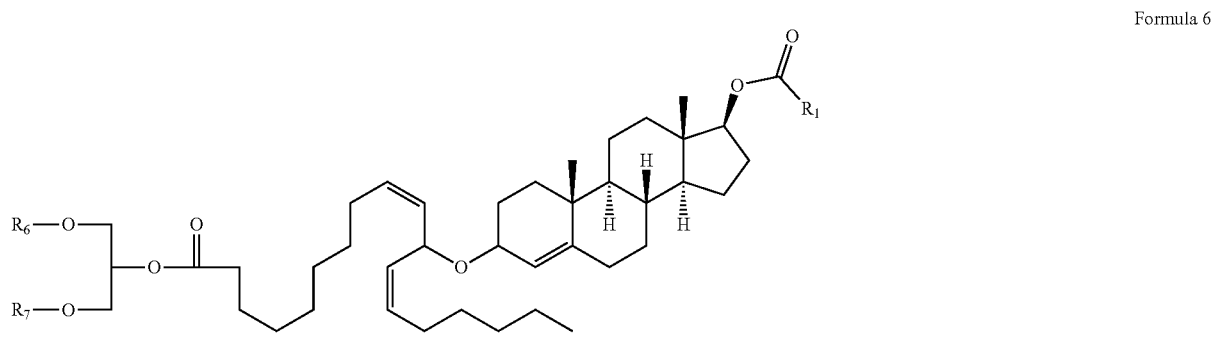
Formula 6

-continued
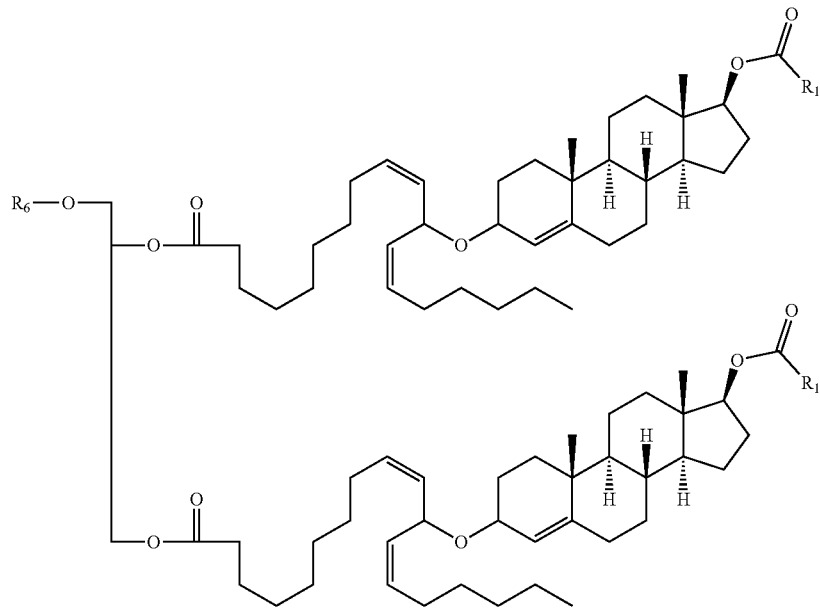
Formula 7
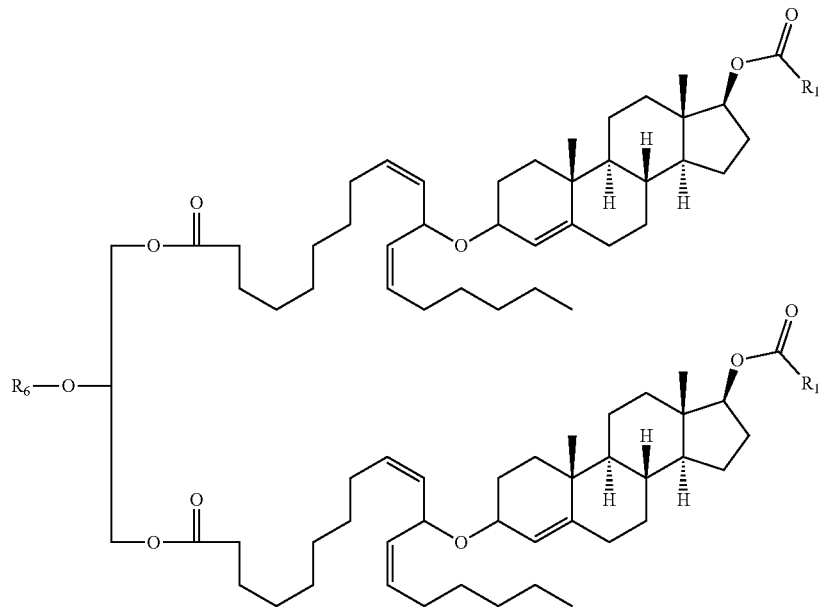
Formula 8

-continued
Formula 9
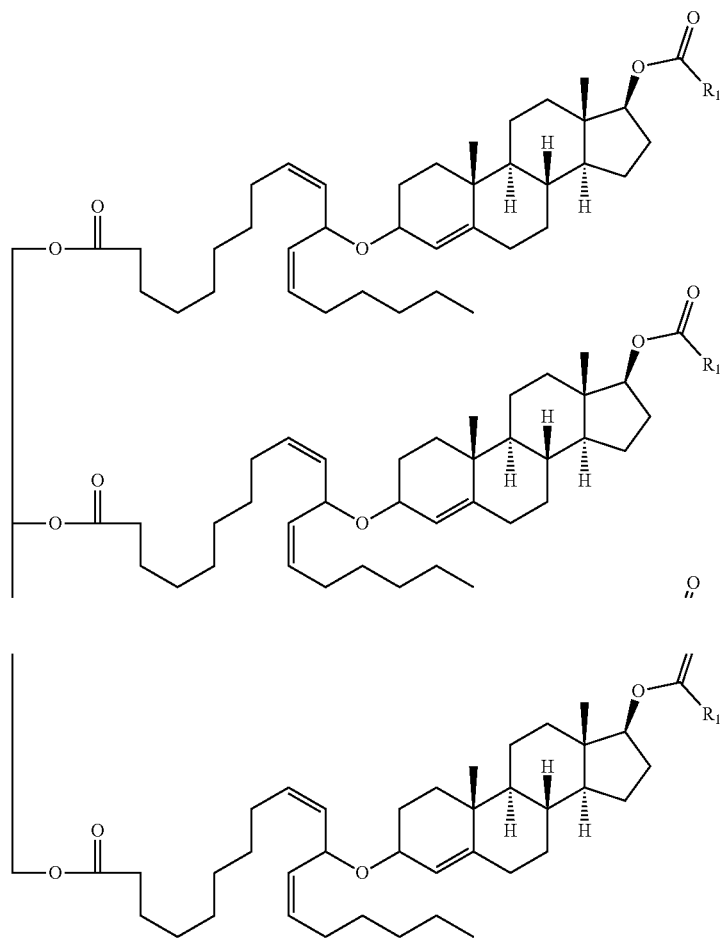
wherein each one of $R_6$ and $R_7$ is independently an acyl group corresponding to a fatty acid selected from the group consisting of linoleic acid, oleic acid, palmitic acid, ricinoleic acid, linolenic acid, and stearic acid.
In some embodiments, the invention relates to a testosterone ester adduct of Formula 10:
Formula 10
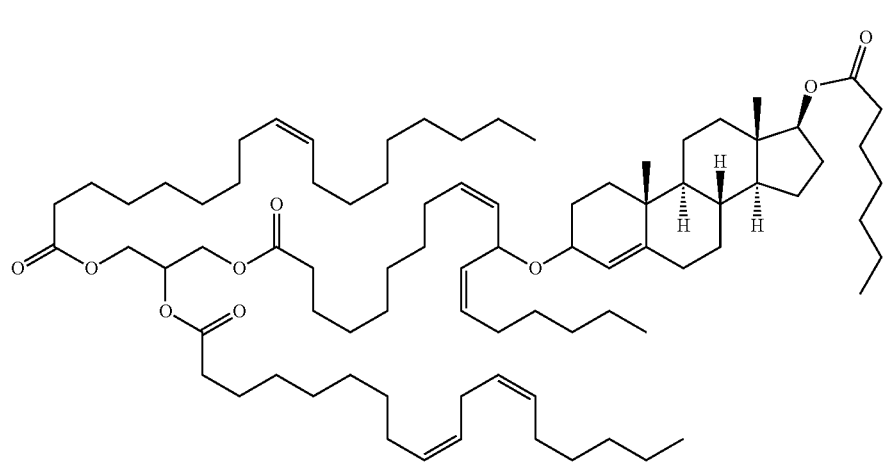

In some embodiments, the invention relates to a testosterone ester adduct of Formula 11:

In some embodiments, the adduct has Formula 10. In some embodiments, the adduct has Formula 11. In some

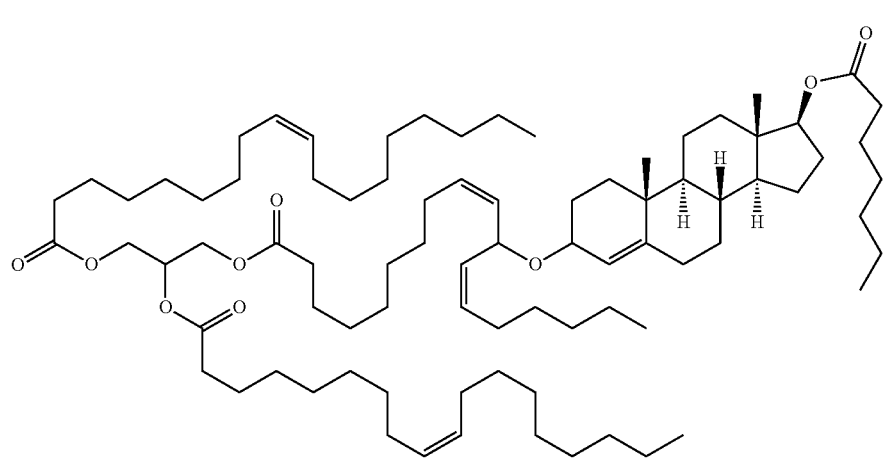

Formula 11

In yet another embodiment, the present invention relates to the testosterone ester formulation described above optionally in combination with a testosterone adduct described above. Such adducts may be useful for, at least, formulation stability purposes. In some embodiments, such adducts may be useful for tagging, identifying, or authenticating a testosterone ester formulation.

Thus, in some embodiments, the invention relates to pharmaceutical formulation including a testosterone ester of Formula 1, a pharmaceutically acceptable carrier including one or more triglycerides of Formula 2, and a testosterone ester adduct of any one of Formulas 3 to 11, wherein $R_1$ is an alkyl or alkenyl substituent, and each of $R_2$, $R_3$, and $R_4$ is an acyl group corresponding to a fatty acid selected from the group consisting of linoleic acid, oleic acid, palmitic acid, ricinoleic acid, linolenic acid, and stearic acid. In some embodiments, $R_1$ is selected at each independent occurrence from the group consisting of propyl, butyl, pentyl, hexyl, heptyl, octyl, nonyl, decyl, undecyl, dodecyl, cyclopentylethyl, and/or unsaturated analogs thereof. In some embodiments, the pharmaceutical formulation is for parenteral administration. In some embodiments, the testosterone ester is testosterone enanthate, testosterone cipionate, testosterone propionate, or testosterone undecanoate. In some embodiments, the testosterone ester is testosterone enanthate. In some embodiments, the triglyceride is one of LLL, OLL, OOL, OOO, PLL, POL, POO, and SOL. In some embodiments, the pharmaceutically acceptable carrier includes a vegetable oil. In some embodiments, the pharmaceutical formulation further includes an antioxidant. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium.

In such embodiments, the concentration of an adduct of the present invention may be between 0.000 mg/ml and the concentration of the testosterone ester of the formulation. In one embodiment, the invention relates to pharmaceutical formulation including testosterone enanthate, sesame oil, BHT, and one or more testosterone adducts of Formulas 3 to 11.

embodiments, the concentration of testosterone enanthate is from 50 mg/mL to 200 mg/mL. In some embodiments, the concentration of BHT is from 0.01% to 0.1%, or from 0.1 mg/mL to 1 mg/mL. In some embodiments, the concentration of a testosterone ester adduct is less than the concentration of testosterone enanthate. In some embodiments, the total concentration of testosterone ester adducts is less than the concentration of testosterone enanthate. In some embodiments, the pharmaceutical formulation is for parenteral administration.

In one embodiment, the invention relates to a stable testosterone ester pharmaceutical formulation including a testosterone ester of Formula 1, an antioxidant, and a pharmaceutically acceptable carrier including one or more triglycerides of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the stress (e.g., light) stability of the formulation is assessed between 30 and 60 days after making the formulation, by measuring the concentration of available testosterone ester and comparing it to the initial testosterone ester concentration in the formulation.

In some embodiments, the pharmaceutical formulation is for parenteral administration.

In one embodiment, the invention relates to a light stable testosterone ester pharmaceutical formulation including a testosterone ester of Formula 1, an antioxidant, and a pharmaceutically acceptable carrier including one or more triglycerides of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed between 30 and 60 days after making the formulation, by measuring the concentration of available testosterone ester and comparing it to the initial testosterone ester concentration in the formulation, and by detecting the optional presence and measuring the concentration of one or more testosterone ester adducts of any one of Formulas 3 to 11 in the formulation. In some embodiments, the pharmaceutical formulation is for parenteral administration.

In one embodiment, the invention relates to a light stable testosterone ester pharmaceutical formulation including a testosterone ester of Formula 1, an antioxidant, and a pharmaceutically acceptable carrier including a triglyceride of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed by exposing the pharmaceutical formulation to UV light at 200 watt hours/square meter and visible light exposure of not less than 1.2 million lux hours, measuring the concentration of available testosterone ester, and comparing it to the initial testosterone ester concentration in the formulation. In some embodiments, the pharmaceutical formulation is for parenteral administration.

In one embodiment, the invention relates to a light stable testosterone ester pharmaceutical formulation including a testosterone ester of Formula 1, an antioxidant, and a pharmaceutically acceptable carrier including a triglyceride of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed by exposing the pharmaceutical formulation to UV light at 200 watt hours/square meter and visible light exposure of not less than 1.2 million lux hours, measuring the concentration of available testosterone ester, comparing it to the initial testosterone ester concentration in the formulation, and detecting the presence and measuring the concentration of a testosterone ester adduct of any one of Formulas 3 to 11 in the formulation. In some embodiments, the pharmaceutical formulation is for parenteral administration.

In one embodiment, the invention relates to a light stable testosterone ester pharmaceutical formulation, wherein the concentration of available testosterone ester in the formulation is at least 66.8% to 75.0% of the initial testosterone ester concentration in the formulation. In some embodiments, the pharmaceutical formulation is for parenteral administration.

In some embodiments, the invention relates to a light stable testosterone ester pharmaceutical formulation including a testosterone ester adduct of any one of Formulas 3 to 11, wherein the concentration of the testosterone ester adduct in the formulation is less than the concentration of available testosterone ester in the formulation. In some embodiments, the pharmaceutical formulation is for parenteral administration.

In one embodiment, the invention relates to a method of measuring the light stability of a testosterone ester pharmaceutical formulation including a testosterone ester of Formula 1, and a pharmaceutically acceptable carrier including one or more triglycerides of Formula 2, the method including the steps of measuring the initial testosterone ester concentration in the formulation, then, after a period of time, measuring the concentration of available testosterone ester in the formulation, and comparing the two concentrations, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid. In some embodiments, the method further includes exposing the pharmaceutical formulation to UV light at 200 watt hours/square meter and visible light exposure of not less than 1.2 million lux hours. In some embodiments, the pharmaceutical formulation further includes an antioxidant such as butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium. In some embodiments, the period of time is between 30 and 60 days. In some embodiments, the method further includes detecting the presence and measuring the concentration of a testosterone ester adduct of any one of Formulas 3 to 11 in the pharmaceutical formulation.

BRIEF DESCRIPTION OF THE DRAWINGS

The foregoing summary, as well as the following detailed description of embodiments of the invention, will be better understood when read in conjunction with the appended drawings and figures.

Figure 1:
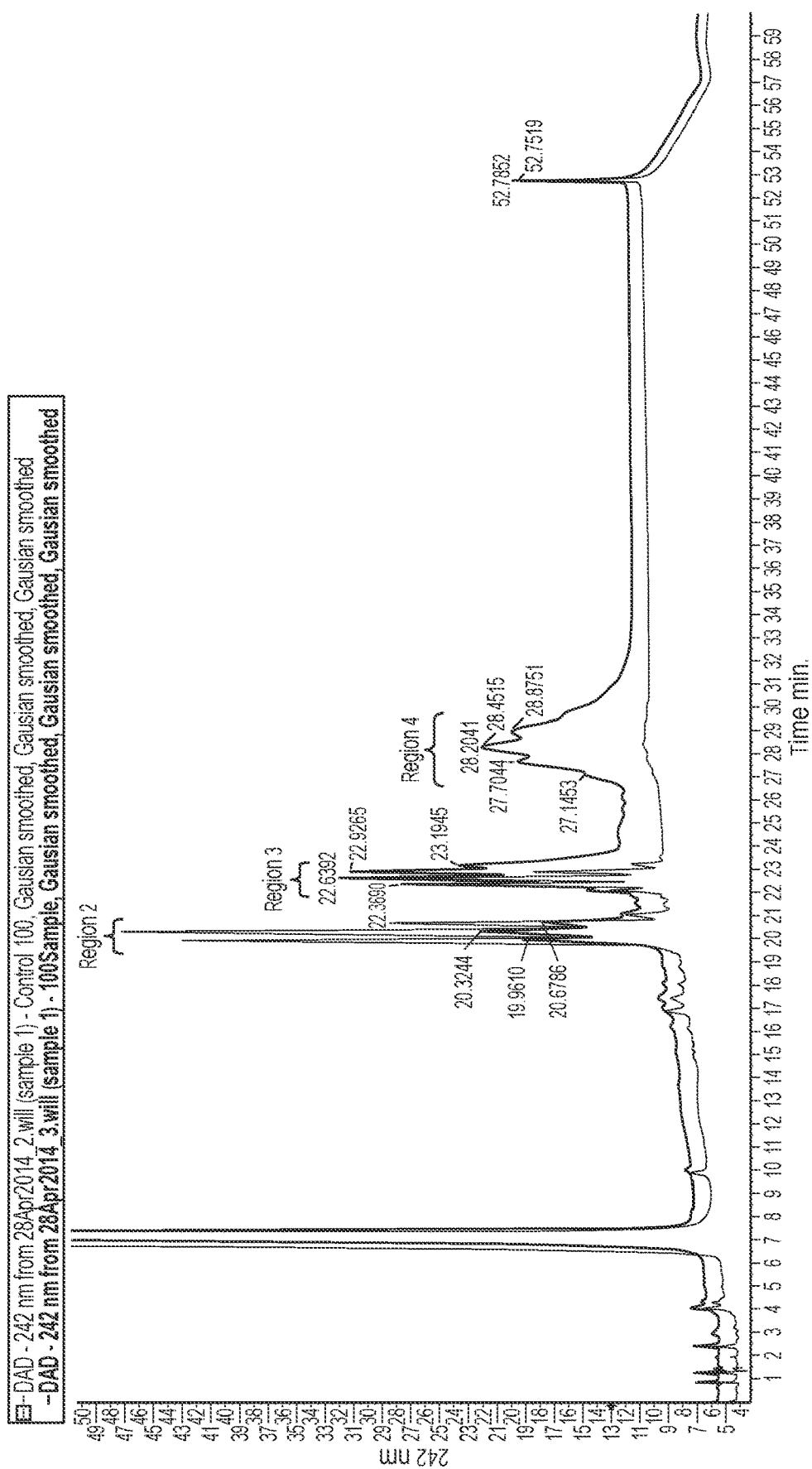
FIG. 1 illustrates UV (242 nm) chromatograms overlaid: control sample (blue) and light stress sample (pink).

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention is directed to a testosterone ester formulation, a testosterone ester adduct, a combination of the testosterone ester formulation and optionally the testosterone ester adduct and a method of controlling the manufacture or formation of the testosterone ester adduct in-situ.

Definitions

Unless defined otherwise, all technical and scientific terms used herein have the same meaning as is commonly understood by one of skill in the art to which this invention belongs. All patents and publications referred to herein are incorporated by reference in their entireties.

As used herein, the terms "administer," "administration," or "administering" refer to (1) providing, giving, dosing, and/or prescribing by either a health practitioner or his authorized agent or under his or her direction according to the disclosure, and/or (2) putting into, taking, or consuming by a subject, for example a mammal, including a human, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. In some embodiments, simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the subject to whom the dose is to be administered, the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of testosterone ester. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a testosterone ester, and/or testosterone) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g., organ or tumor-targeting, lymphocyte targeting), to modify or improve aqueous solubility of a drug (e.g., i.v. preparations and eyedrops), to improve topical drug delivery (e.g., dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C-enriched or $^{14}$C-enriched carbons, are within the scope of this invention.

As used herein, three letter codes can be used to refer to triglycerides, where each letter refers to a particular fatty acid. Individual fatty acids, substituent fatty acids, substituted fatty acids, or fatty acid radicals can be referred to by their one letter initial, see for example The United States Pharmacopeial Convention, 2015, Sesame Oil. For example, fatty acid radicals can be designated as linoleic (L), oleic (O), palmitic (P), and stearic (S), and the common abbreviations for triglycerides are: trilinolein (LLL), 1,2-dilinoleoyl-3-oleoyl-rac-glycerol (OLL), 1,2-dilinoleoyl-3-palmitoyl-rac-glycerol (PLL), 1,2-dioleoyl-3-linoleoyl-rac-glycerol (OOL), 1-palmitoyl-2-oleoyl-3-linoleoyl-rac-glycerol (POL), triolein (OOO), 1-linoleoyl-2-oleoyl-3-stearoyl-rac-glycerol (SOL), 1,2-dioleoyl-3-palmitoyl-rac-glycerol (POO), and the like. Where necessary, a fatty acid one letter code can be underlined in order to distinguish a fatty acid radical (underlined), from a one letter code describing a different entity. For example, "O" for oleic acid can be distinguished from "O" for oxygen.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5%, or the like, of the stated number or numerical range.

As used herein, the term "about" means that amounts, sizes, formulations, parameters, shapes and other quantities and characteristics are not, and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method, or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range, e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$— (where t is 1 or 2), —$S(O)_tOR^a$ (where t is 1 or 2), —$S(O)_tN(R^a)_2$ (where t is 1 or 2), or $PO_3(R^a)_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. The alkyl moiety, whether saturated or unsaturated, may be branched, straight chain, or cyclic.

An "alkene" or "alkenyl" moiety refers to a group consisting of at least two carbon atoms and at least one carbon-carbon double bond, and an "alkyne" moiety refers to a group consisting of at least two carbon atoms and at least one carbon-carbon triple bond.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$— (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$— (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$— (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

DETAILED DESCRIPTION

Formulations

In one embodiment, the invention relates to a pharmaceutical formulation including a testosterone ester of Formula 1, or a pharmaceutically acceptable salt, solvate, hydrate, cocrystal, or prodrug thereof, an antioxidant, and a pharmaceutically acceptable carrier including one or more triglycerides of Formula 2:

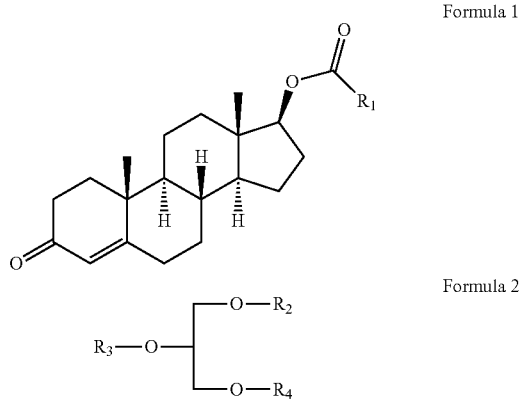

Formula 1

Formula 2 wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and stearic acid. In some embodiments, $R_1$ is propyl, butyl, pentyl, hexyl, heptyl, octyl, nonyl, decyl, undecyl, dodecyl, cyclopentylethyl, or unsaturated analogs thereof. In some embodiments, the testosterone ester is testosterone enanthate, testosterone cipionate, testosterone propionate, or testosterone undecanoate. In some embodiments, the testosterone ester is testosterone enanthate.

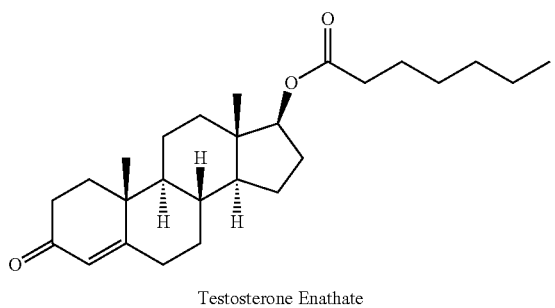

Testosterone Enathate

Other drugs can be used in the formulation, in particular drugs with an α,β-unsaturated ketone moiety, for example cortisone or hydrocortisone. In some embodiments, various other active ingredients can be included in the formulation, for example nonsteroidal estrogens such as benzestrol, broparoestrol, chlorotrianisene, dienestrol, diethylstilboestrol, diethylstilboestrol dipropionate, dimestrol, fosfestrol, hexoestrol, methallenestril and methestrol, and steroidal estrogens such as colpormon, conjugated estrogenic hormones, equilenin, equilin, estradiol, 17-beta-estradiol, estriol, estrone, ethinyl estradiol, estradiol benzoate, estradiol 17-beta-cypionate, polyestradiol phosphate, mestranol, moxestrol, mytatrienediol, quinestradiol, quinestrol, progestogens such as allylestrenol, anagestone, chlormardinone acetate, delmadinone acetate, demegestone, desogestrel, dimethisterone, drospirenone, dydrogesterone, ethynilestrenol, ethisterone, ethynodiol, ethynodiol diacetate, fluorogestone acetate, gestodene, gestonorone caproate, haloprogesterone, 17-hydroxy-16-methylene-delta-progesterone, 17-alpha-hydroxyprogesterone, 17-alpha-hydroxygesterone caproate, lynestrenol, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, natural progesterone, promegestone, quingestrone, trengestone; androgens such as boldenone, cloxotestosterone, fluoxymesterone, mestanolone, mesteronolone, 17-methyltestosterone, testosterone 17-beta-cypionate, testosterone enanthate, testosterone nicotinate, testosterone phenylacetate, testosterone propionate, 17-alpha-methyltestosterone 3-cyclopentyl enol ether, norethandrolone, normethandrone, oxandrolone, oxymesterone, oxymetholone, prasterone, stanolone, stanolozol, testosterone, and/or tiomesterone. The active agent may be an anti-hormone. For example, the pharmaceutical active agent may include but is not limited to an estrogen, androgen, or progestogen, an anti estrogen such as tamoxifen, 4-OH tamoxifen, anti progestogens and anti androgens. Generally, any drug suitable for parenteral administration can be used in the formulations of the invention.

Any glycerides, including triglycerides, diglycerides, and/or monoglycerides, suitable for parenteral administration, can be used in the formulations of the invention. In some embodiments, the triglyceride is one of LLL, OLL, OOL, 000, PLL, POL, POO, or SOL. In one embodiment, triglycerides can also include SSL, SLS, LLS, LSL, MML, MLM, MML, LLM, SSM, SMS, MMM, SSS, and LLL. Long, medium, short, and mixed length chain triglycerides can be used. Triglycerides also include any triglyceride including residues of any known fatty acids, or any other shorter chain saturated or unsaturated acids. Fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, and/or cerotic acid. While fatty acids are primarily present in the formulations described herein as residues part of a triglyceride, diglyceride, or monoglyceride, independent fatty acids can be part of the formulations as well. All triglycerides, diglycerides, monoglycerides, and/or fatty acids described herein can form the adducts described herein with a testosterone ester, for example testosterone enanthate.

In some embodiments, the pharmaceutically acceptable carrier includes a vegetable oil. In some embodiments, the vegetable oil is sesame oil. Other oils, including vegetal or nonvegetal, can be used, for example castor oil, cottonseed oil, soybean oil, and/or safflower oil. Generally, any oil suitable for parenteral administration can be used in the formulations of the invention.

Any antioxidant suitable for parenteral administration can be used in the formulations of the invention. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium.

In one embodiment, the invention relates to a pharmaceutical formulation including testosterone enanthate, sesame oil, and BHT. In one embodiment, the invention relates to a pharmaceutical formulation including testosterone enanthate, sesame oil, and tocopherol.

Adducts for Optional Inclusion in a Formulation

In another embodiment, the invention relates to a testosterone ester adduct of Formula 3:

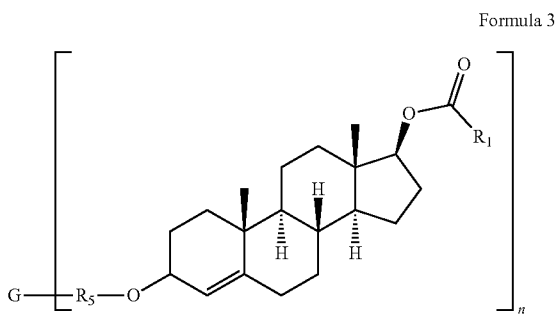

Formula 3 wherein $R_1$ is an alkyl or alkenyl substituent which can be the same or different at each independent occurrence, $R_5$ is an acyl group corresponding to an unsaturated fatty acid, G is a glycerol, monoglyceride, or diglyceride residue, n is 1, 2, or 3, and the testosterone residue is connected to an allylic or doubly allylic carbon of $R_5$.

Such adducts can be separated after such adducts are made and formulated alone, or can be formulated in combination with other constituents, such as those described herein.

Adducts of Formula 3 can be made purposefully or may form unexpectedly or unpredictably, under various conditions, in drug formulations described herein which include an α,β-unsaturated ketone moiety and a glyceride, for example a mono, di, or triglyceride, having an unsaturated acyl residue. In some embodiments, the invention relates to an isolated testosterone ester adduct of Formula 3, or an isolated testosterone ester adduct of any formula described herein.

In some embodiments, the conditions that lead to the formation of adducts described herein, are referred to as stressor conditions, including, but not limited to, exposure to light, and/or exposure to an oxidant atmosphere, for example exposure to oxygen, and/or exposure to any stressor condition known in the art. A testosterone ester, such as testosterone enanthate (TE), is an example of a drug including an α,β-unsaturated ketone moiety, and sesame oil is an example of an oil including triglycerides containing unsaturated acyl moieties, for example double bonds and/or homoconjugated double bonds such as the linoleoyl side chain. Without wishing to be bound by any particular theory, the adducts described herein can be made or occur as a result of the addition of an α,β-unsaturated ketone compound, for example a testosterone derivative, to a hydrocarbon chain, for example a hydrocarbon chain included in a fatty acid, wherein addition occurs adjacent to a double bond.

In some embodiments, the adducts described herein can be made or occur as a result of autoxidation. Without wishing to be bound by any particular theory, unsaturated acyl moieties and side chains are labile to autoxidation in the presence of oxygen, light, or light and oxygen. The autoxidation of these side chains generates a hydroperoxide group, for example a linoleoyl hydroperoxide, along with a free radical, for example a linoleoyl free radical, and a peroxy radical, for example a linoleoyl peroxy radical (Scheme 5). Because the linoleoyl free radical, and the linoleoyl peroxy radical are reactive, the autoxidation is an autocatalytic chain reaction.

The extent of oxidation of a mixture of TGs can be measured by a USP test called the Peroxide Value (PV). The peroxide value is defined as the amount of peroxide oxygen per 1 kilogram of fat or oil (milli-eqivalent of $O_2$/kg of oil). Generally, the PV of a mixture of TGs, whether containing a drug or not, increases over time, indicating that the TGs in the mixture is oxidized over time. Without wishing to be bound by any particular theory, when the TGs become oxidized in the presence of an α,β-unsaturated ketone moiety, the ketone moiety can react with the carbon atom attached to the peroxy moiety to afford various adducts described herein.

In some embodiments, the testosterone ester adduct has Formula 4. In some embodiments, $R_1$ is one of propyl, butyl, pentyl, hexyl, heptyl, octyl, nonyl, decyl, undecyl, dodecyl, cyclopentylethyl, and/or unsaturated analogs thereof. In some embodiments, $R_1$ is hexyl.

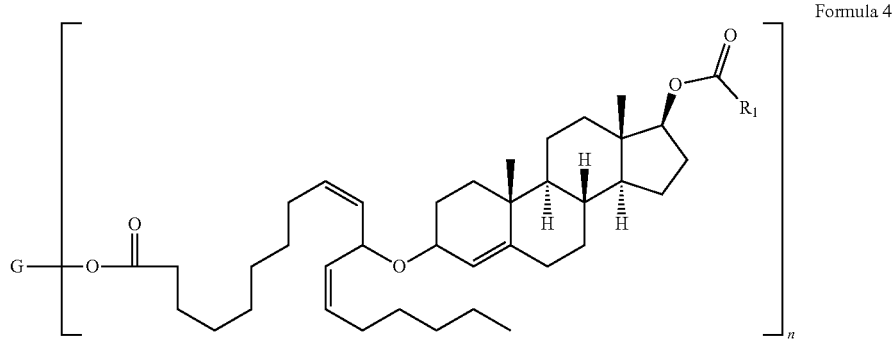

Formula 4

In some embodiments, the invention relates to a testosterone ester adduct of any one of Formulas 5 to 9:
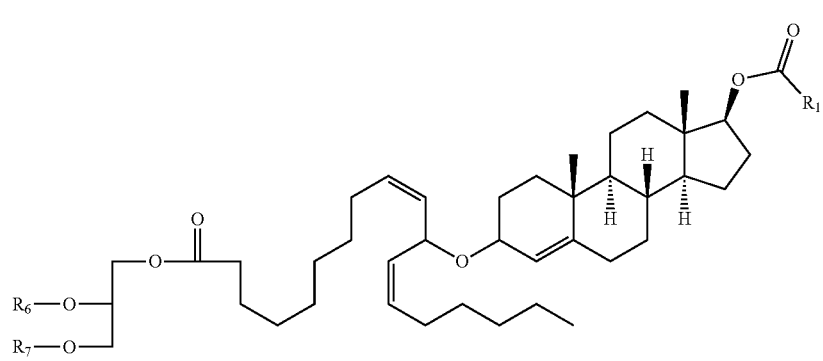
Formula 5
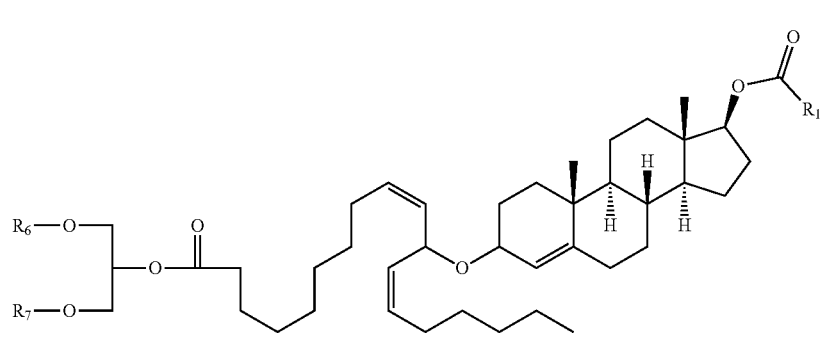
Formula 6
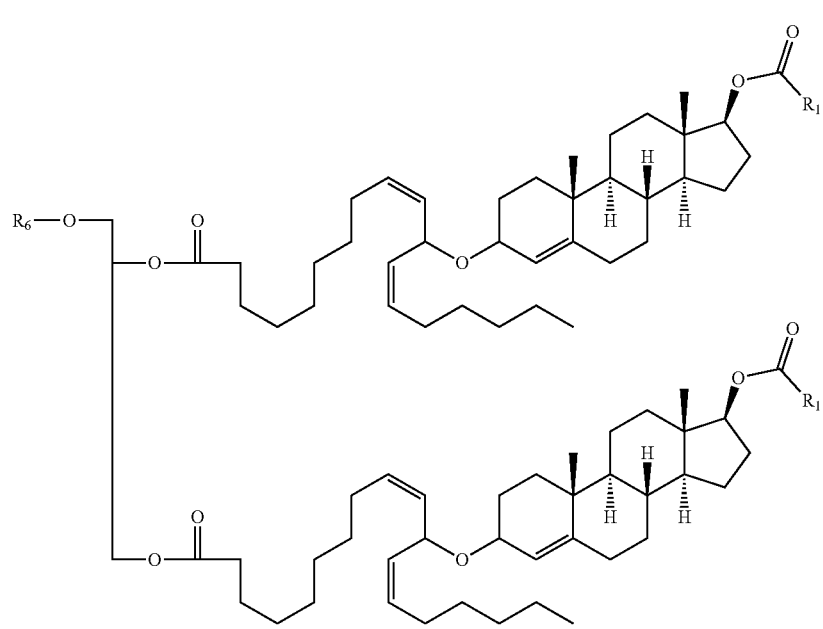
Formula 7

-continued
Formula 8
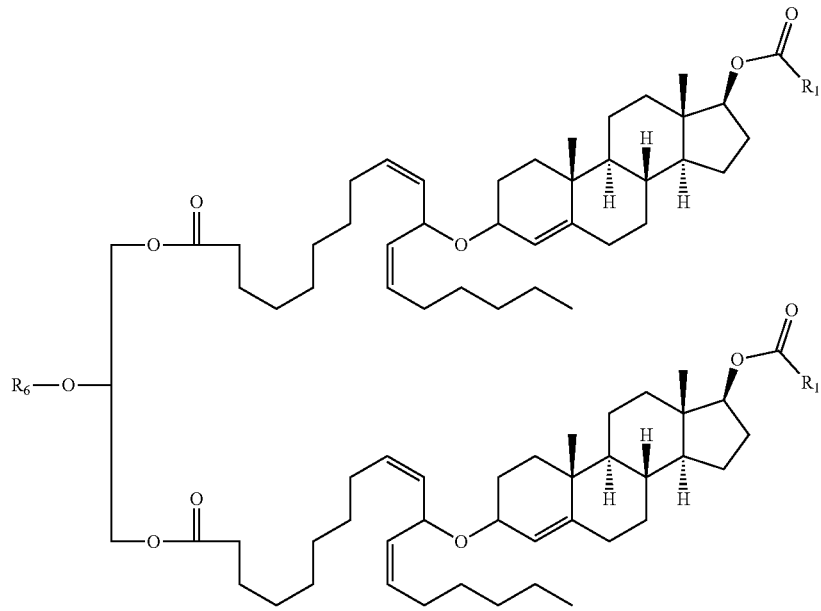
Formula 9
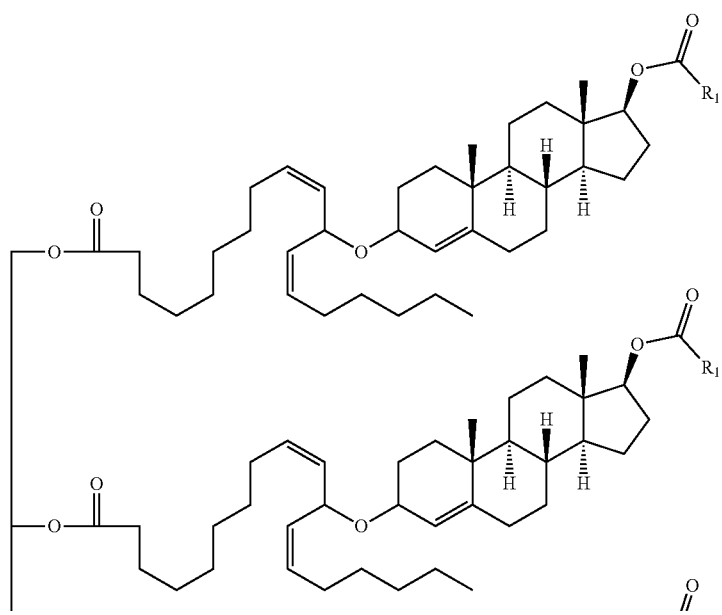
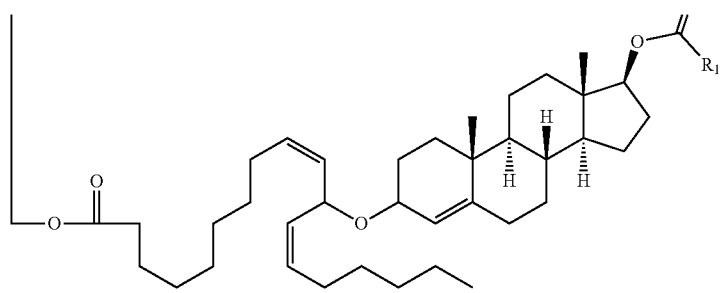
wherein each one of $R_6$ and $R_7$ is independently an acyl group corresponding to a fatty acid selected from the group consisting of linoleic acid, oleic acid, palmitic acid, ricinoleic acid, linolenic acid, and stearic acid.

In some embodiments, the invention relates to a testosterone ester adduct of Formula 10:

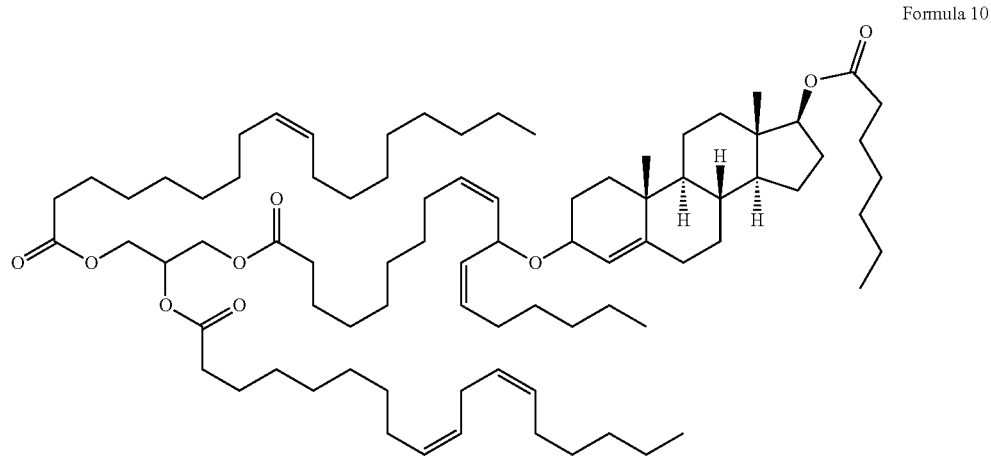

Formula 10

In some embodiments, the invention relates to a testosterone ester adduct of Formula 11:

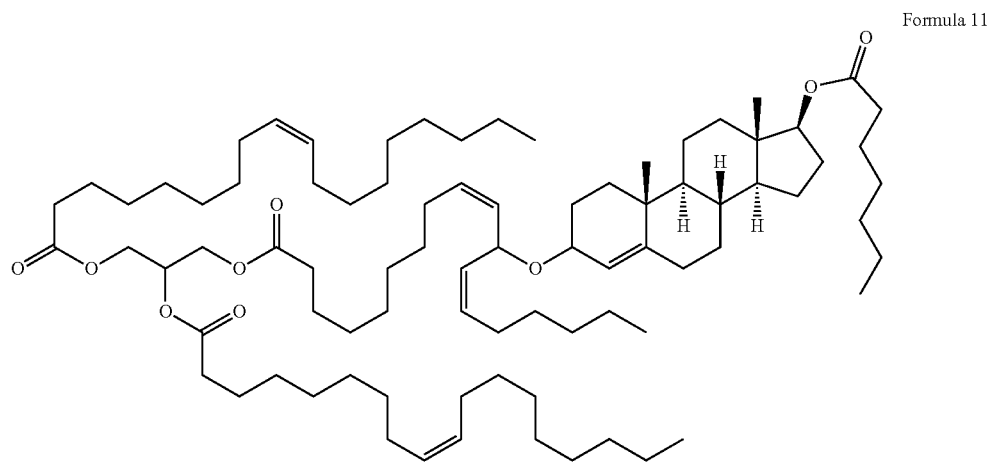

Formula 11

The adducts described herein can have various other formulas. Without wishing to be bound by any particular theory, the geometry of any fatty acid chain double bonds is generally conserved following the adduct formation process, but in some embodiments, the geometry can change. Also, without wishing to be bound by any particular theory, while the addition occurs generally at allylic and doubly allylic positions, addition can occur at other positions as well, for example homoallylic positions. Adducts of the following Formulas 12 to 16 can thus be formed, wherein G is a glycerol, monoglyceride, or diglyceride residue, and n is 1, 2, or 3.

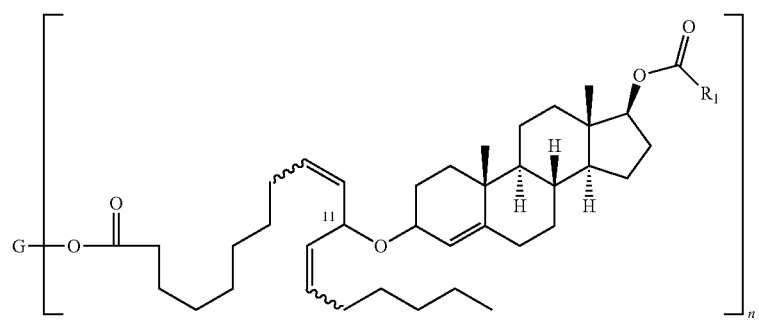
Formula 12
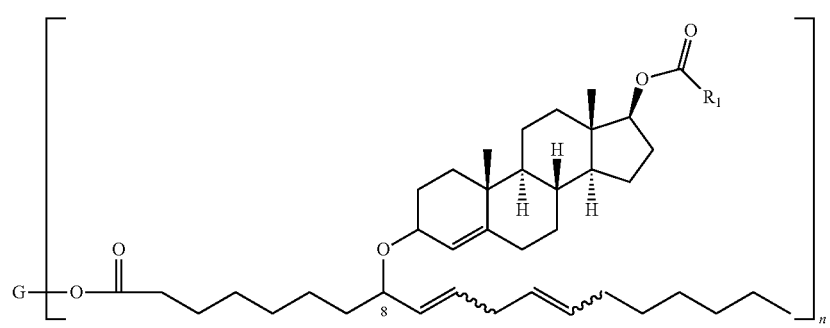
Formula 13
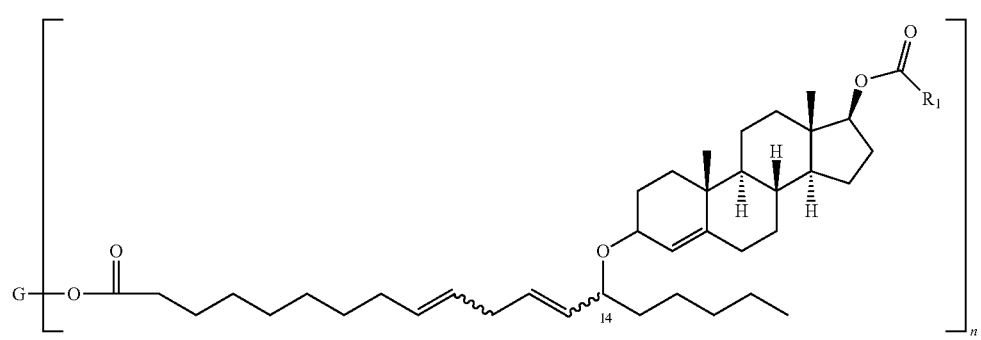
Formula 14
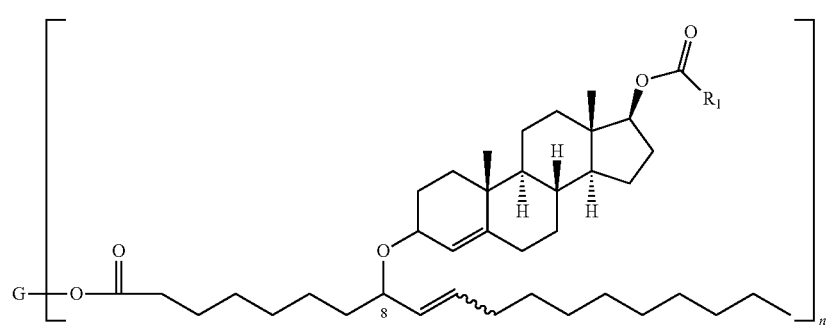
Formula 15
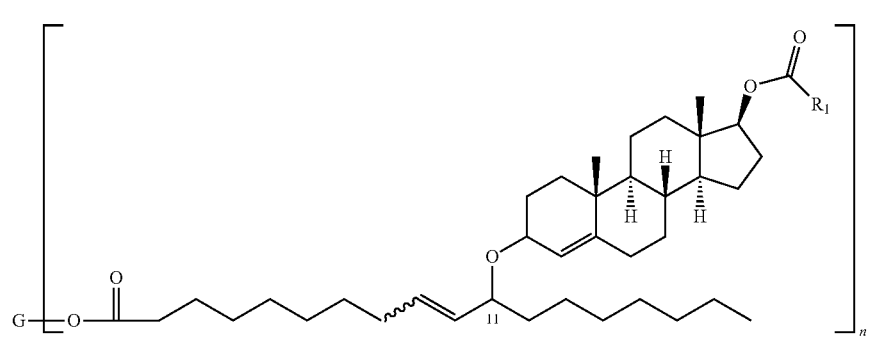
Formula 16

Regioisomeric adducts of the following Formulas 17 to 22 can also be formed, wherein P, L, O, and S correspond to the respective fatty acid acyl groups, and the testosterone residue is linked at any possible position along the fatty acid side chain.

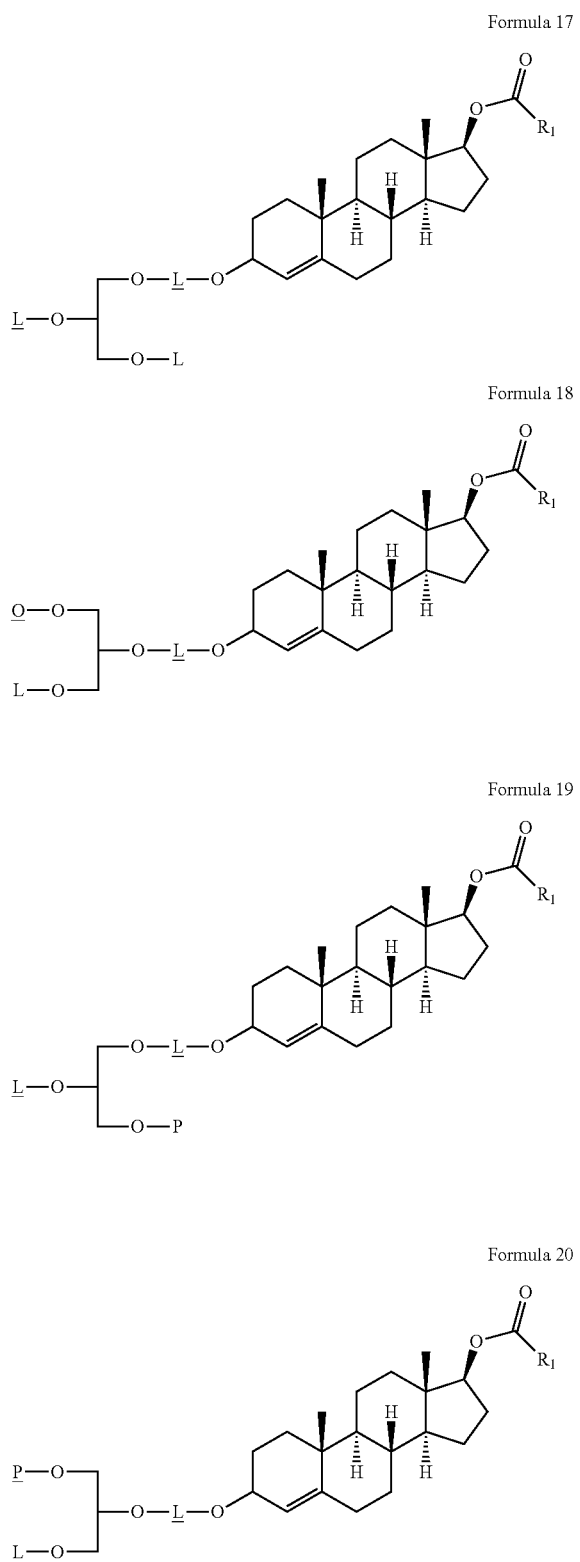

Formula 17

Formula 18

Formula 19

Formula 20

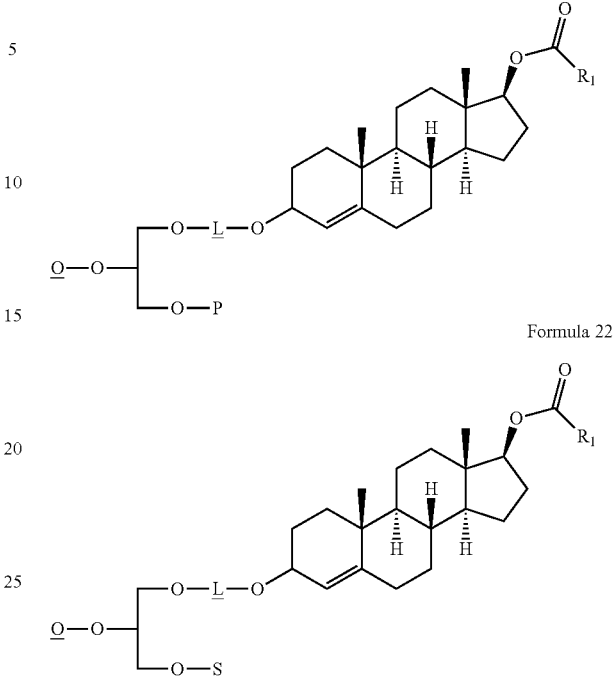

Formula 21

Formula 22

In some embodiments, the testosterone ester triglyceride adducts described herein can be made or form when a percentage of the initial testosterone ester in the formulation is transformed, over a period of time, into an adduct thereof, under various conditions described herein.

In some embodiments, the percentage of the initial testosterone ester in a formulation, for example testosterone enanthate, which is converted into an adduct of testosterone ester with a triglyceride, is less than about 0.001%, about 0.001%, about 0.002%, about 0.003%, about 0.004%, about 0.005%, about 0.006%, about 0.007%, about 0.008%, about 0.009%, about 0.01%, about 0.015%, about 0.02%, about 0.025%, about 0.03%, about 0.035%, about 0.04%, about 0.045%, about 0.05%, about 0.055%, about 0.06%, about 0.065%, about 0.07%, about 0.075%, about 0.08%, about 0.085%, about 0.09%, about 0.095%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, or more than about 1%.

In some embodiments, the percentage of the initial testosterone ester in a formulation, for example testosterone enanthate, which is converted into an adduct of testosterone ester with a triglyceride, is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments, a percentage of the initial testosterone ester, for example testosterone enanthate, is converted into an adduct of testosterone ester with a triglyceride after about 1 hour, after about 2 hours, after about 3 hours, after about 4 hours, after about 5 hours, after 6 about hours, after about 7 hours, after about 8 hours, after about 9 hours, after about 10 hours, after about 11 hours, after about 12 hours, after about 13 hours, after about 14 hours, after about 15 hours, after about 16 hours, after about 17 hours, after about 18 hours, after about 19 hours, after about 20 hours, after about 21 hours, after about 22 hours, after about 23 hours, after about 24 hours, after about 1 day, after about 2 days, after about 3 days, after about 4 days, after about 5 days, after 6 about days, after about 7 days, after about 8 days, after about 9 days, after about 10 days, after about 15 days, after about 20 days, after about 25 days, after about 30 days, after about 35 days, after about 40 days, after about 45 days, after about 50 days, after about 55 days, after about 60 days, after about 90 days, after about 120 days, after about 180 days, after about 1 week, after about 2 weeks, after about 3 weeks, after about 4 weeks, after about 5 weeks, after 6 about weeks, after about 7 weeks, after about 8 weeks, after about 9 weeks, after about 10 weeks, after about 1 month, after about 2 months, after about 3 months, after about 4 months, after about 5 months, after 6 about months, after about 7 months, after about 8 months, after about 9 months, after about 10 months, after about 11 months, after about 12 months, after about 18 months, after about 36 months, after about 1 year, after about 2 years, after about 3 years, after about 4 years, after about 5 years, or after 6 about years.

In some embodiments, a percentage of the initial testosterone ester, for example testosterone enanthate, is converted into an adduct of testosterone ester with a triglyceride during normal storage conditions, for example while in a prefilled syringe (PFS) or vial. In some embodiments, the PFS can be exposed to ambient light, or can be shielded from light, for example in any type of opaque container such as a cardboard box. In some embodiments, a percentage of the initial testosterone ester, for example testosterone enanthate, is converted into an adduct of testosterone enanthate with a triglyceride under enhanced light conditions, for example 200 watt hours/square meter and visible light exposure of not less than 1.2 million lux hours. In some embodiments, a percentage of the initial testosterone ester in a pharmaceutical formulation, for example testosterone enanthate, is converted into an adduct of testosterone ester with a triglyceride after exposing the pharmaceutical formulations to ambient light, or to UV light and/or visible light amounts which are equivalents to exposure to ambient light for about 1 hour, for about 2 hours, for about 3 hours, for about 4 hours, for about 5 hours, for about 6 hours, for about 7 hours, for about 8 hours, for about 9 hours, for about 10 hours, for about 11 hours, for about 12 hours, for about 13 hours, for about 14 hours, for about 15 hours, for about 16 hours, for about 17 hours, for about 18 hours, for about 19 hours, for about 20 hours, for about 21 hours, for about 22 hours, for about 23 hours, for about 24 hours, for about 1 day, for about 2 days, for about 3 days, for about 4 days, for about 5 days, for 6 about days, for about 7 days, for about 8 days, for about 9 days, for about 10 days, for about 15 days, for about 20 days, for about 25 days, for about 30 days, for about 35 days, for about 40 days, for about 45 days, for about 50 days, for about 55 days, for about 60 days, for about 90 days, for about 120 days, for about 180 days, for about 1 week, for about 2 weeks, for about 3 weeks, for about 4 weeks, for about 5 weeks, for 6 about weeks, for about 7 weeks, for about 8 weeks, for about 9 weeks, for about 10 weeks, for about 1 month, for about 2 months, for about 3 months, for about 4 months, for about 5 months, for 6 about months, for about 7 months, for about 8 months, for about 9 months, for about 10 months, for about 11 months, for about 12 months, for about 18 months, for about 36 months, for about 1 year, for about 2 years, for about 3 years, for about 4 years, for about 5 years, for 6 about years, or for any other period of time.

Controlling or Inhibiting Formation of Adducts In-Situ—

The creation or formation of testosterone ester triglyceride adducts described herein can be controlled or the formation thereof inhibited in-situ by adding to the formulation an antioxidant.

Thus, in certain embodiments the invention relates generally to the addition of an antioxidant (such a butylated hydroxytoluene (BHT)) to a testosterone ester formulation, such as a testosterone enanthate injectable drug formulation, and thus controlling the in-situ manufacture or creation of an adduct of the present invention.

Such control can improve the photo-stability of the drug formulation. Without being limited by any particular theory, the invention which controls the in-situ formation of an adduct works in part because the formation of lipid peroxides is inhibited during the aging of the formulation product, and/or exposure to light. The inhibition of peroxides formation, for example lipid peroxides formation, applies as well to the ingredients before the formulation product is in its final form. The invention relates as well to identifying important products formed under light stress, and products which account, at least in part, for the decline of testosterone ester concentration in a testosterone ester formulation under various aging conditions.

Without wishing to be bound by theory, BHT acts as a free radical scavenger during the manufacture or creation of an adduct of the present invention. It stops the autoxidation of TGs by donating a hydrogen atom to convert the peroxy radicals to the hydroperoxides and TG radicals to TGs, while generating a BHT radical, as shown in Scheme 6. Once formed, the BHT radical cannot react further because the large tert-butyl groups create so much steric hindrance that the oxygen atom bearing the unpaired electron cannot make the required contact with other molecules to allow a reaction. Formation of the BHT radical stops radical chain reactions, for example the autoxidation of a triglyceride, more specifically, the autoxidation of the unsaturated triglyceride side chain.

Oxidation of triglyceride containing oil can be effectively controlled or inhibited in the presence of 0.06-0.07% of an antioxidant (e.g., BHT). In some embodiments, TGs oxidation can be inhibited in the presence of from about 0.01% to about 0.1% BHT, or any other suitable antioxidant, for example tocopherol. In other embodiments, TGs oxidation can be inhibited in the presence of from about 0.05% to about 0.5% BHT, or any other suitable antioxidant. As described herein, the peroxide value (PV) level of a mixture of triglycerides can be maintained at a lower level in time, e.g., <12, by adding an antioxidant to the mixture, compared to the PV level of approximately 70-80 without antioxidant. PV levels in a formulation can be determined after various periods of time after making the formulation, for example after about 1 month, after about 2 months, after about 3 months, after about 4 months, after about 5 months, after 6 about months, after about 7 months, after about 8 months, after about 9 months, after about 10 months, after about 11 months, after about 12 months, after about 18 months, or after about 36 months.

An alternative measure of available testosterone ester concentration is to measure degradation in the absence and in the presence of an antioxidant, wherein addition of an antioxidant results in reduced levels of degradation. In some embodiments, by adding an antioxidant to a particular formulation, formation of an adduct over a certain period of time is reduced by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, compared to formation occurring during a similar period of time in a formulation without added antioxidant.

In some embodiments, the invention relates to a pharmaceutical formulation including a testosterone ester of Formula 1, a pharmaceutically acceptable carrier including one or more triglycerides of Formula 2, and a testosterone ester adduct of any one of Formulas 3 to 22, wherein $R_1$ is an alkyl or alkenyl substituent, and each of $R_2$, $R_3$, and $R_4$ is an acyl group corresponding to a fatty acid selected from the group consisting of linoleic acid, oleic acid, palmitic acid, ricinoleic acid, linolenic acid, and stearic acid. In some embodiments, $R_1$ is selected at each independent occurrence from the group consisting of propyl, butyl, pentyl, hexyl, heptyl, octyl, nonyl, decyl, undecyl, dodecyl, cyclopentylethyl, and/or unsaturated analogs thereof. In some embodiments, the testosterone ester is testosterone enanthate, testosterone cipionate, testosterone propionate, or testosterone undecanoate. In some embodiments, the testosterone ester is testosterone enanthate. In some embodiments, the triglyceride is one of LLL, OLL, OOL, OOO, PLL, POL, POO, and SOL. In some embodiments, the pharmaceutically acceptable carrier includes a vegetable oil. In some embodiments, the pharmaceutical formulation further includes an antioxidant. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium.

The testosterone ester adduct of any one of Formulas 3 to 22 can be optionally present in any of the formulations described herein, typically either as a result of an unpredictable or controlled in-situ creation, or as a result of intentionally introducing such an adduct in the formulation. The concentration of the adduct in the formulation can be any concentration, but it will generally be less than the concentration of the corresponding testosterone ester in the formulation at any given moment in time.

Stable Formulations In one embodiment, the invention relates to a light stable testosterone ester pharmaceutical formulation including a testosterone ester of Formula 1, an antioxidant, and a pharmaceutically acceptable carrier including one or more triglycerides of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed between 30 and 60 days after making the formulation, by measuring the concentration of available testosterone ester and comparing it to the initial testosterone ester concentration in the formulation.

In one embodiment, the invention relates to a light stable testosterone ester pharmaceutical formulation including a testosterone ester of Formula 1, an antioxidant, and a pharmaceutically acceptable carrier including one or more triglycerides of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and optionally an adduct of the present invention.

The light stability of the formulation is assessed between 30 and 60 days after making the formulation, by measuring the concentration of available testosterone ester and comparing it to the initial testosterone ester concentration in the formulation, and by detecting the presence and measuring the concentration of one or more testosterone ester adducts of any one of Formulas 3 to 22 in the formulation.

The light stability of any formulation described herein can be assessed at any time after the initial formulation is made. For example, light stability can be assessed after about 1 hour, after about 2 hours, after about 3 hours, after about 4 hours, after about 5 hours, after 6 about hours, after about 7 hours, after about 8 hours, after about 9 hours, after about 10 hours, after about 11 hours, after about 12 hours, after about 13 hours, after about 14 hours, after about 15 hours, after about 16 hours, after about 17 hours, after about 18 hours, after about 19 hours, after about 20 hours, after about 21 hours, after about 22 hours, after about 23 hours, or after about 24 hours.

Light stability can also be assessed after about 1 day, after about 2 days, after about 3 days, after about 4 days, after about 5 days, after 6 about days, after about 7 days, after about 8 days, after about 9 days, after about 10 days, after about 15 days, after about 20 days, after about 25 days, after about 30 days, after about 35 days, after about 40 days, after about 45 days, after about 50 days, after about 55 days, after about 60 days, after about 90 days, after about 120 days, or after about 180 days.

Light stability can also be assessed after about 1 week, after about 2 weeks, after about 3 weeks, after about 4 weeks, after about 5 weeks, after 6 about weeks, after about 7 weeks, after about 8 weeks, after about 9 weeks, or after about 10 weeks. Light stability can also be assessed after about 1 month, after about 2 months, after about 3 months, after about 4 months, after about 5 months, after 6 about months, after about 7 months, after about 8 months, after about 9 months, after about 10 months, after about 11 months, after about 12 months, after about 18 months, or after about 36 months. Light stability can also be assessed after about 1 year, after about 2 years, after about 3 years, after about 4 years, after about 5 years, after 6 about years, or any number of years after the initial formulation was made.

In one embodiment, the invention relates to a light stable testosterone ester pharmaceutical formulation including a testosterone ester of Formula 1, an antioxidant, and a pharmaceutically acceptable carrier including a triglyceride of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed by exposing the pharmaceutical formulation to UV light at 200 watt hours/square meter and visible light exposure of not less than 1.2 million lux hours, measuring the concentration of available testosterone ester, and comparing it to the initial testosterone ester concentration in the formulation.

In one embodiment, the invention relates to a light stable testosterone ester pharmaceutical formulation including a testosterone ester of Formula 1, an antioxidant, and a pharmaceutically acceptable carrier including a triglyceride of Formula 2, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid, and the light stability of the formulation is assessed by exposing the pharmaceutical formulation to UV light at 200 watt hours/square meter and visible light exposure of not less than 1.2 million lux hours, measuring the concentration of available testosterone ester, comparing it to the initial testosterone ester concentration in the formulation, and detecting the presence and measuring the concentration of a testosterone ester adduct of any one of Formulas 3 to 22 in the formulation.

The light stability of the formulations described herein is assessed by exposing the pharmaceutical formulation to UV light at 200 watt hours/square meter and visible light exposure of not less than 1.2 million lux hours, but any light exposure values can be used. For example, light stability can be determined after exposing the pharmaceutical formulations to UV light and/or visible light amounts which are equivalents to exposure to ambient light for about 1 hour, for about 2 hours, for about 3 hours, for about 4 hours, for about 5 hours, for about 6 hours, for about 7 hours, for about 8 hours, for about 9 hours, for about 10 hours, for about 11 hours, for about 12 hours, for about 13 hours, for about 14 hours, for about 15 hours, for about 16 hours, for about 17 hours, for about 18 hours, for about 19 hours, for about 20 hours, for about 21 hours, for about 22 hours, for about 23 hours, for about 24 hours, or the like.

Light stability can also be determined after exposing the pharmaceutical formulations to UV light and/or visible light amounts which are equivalents to exposure to ambient light for about 1 day, for about 2 days, for about 3 days, for about 4 days, for about 5 days, for 6 about days, for about 7 days, for about 8 days, for about 9 days, for about 10 days, for about 15 days, for about 20 days, for about 25 days, for about 30 days, for about 35 days, for about 40 days, for about 45 days, for about 50 days, for about 55 days, for about 60 days, for about 90 days, for about 120 days, or for about 180 days, or the like.

Light stability can also be determined after exposing the pharmaceutical formulations to UV light and/or visible light amounts which are equivalents to exposure to ambient light for about 1 week, for about 2 weeks, for about 3 weeks, for about 4 weeks, for about 5 weeks, for 6 about weeks, for about 7 weeks, for about 8 weeks, for about 9 weeks, for about 10 weeks, for about 1 month, for about 2 months, for about 3 months, for about 4 months, for about 5 months, for 6 about months, for about 7 months, for about 8 months, for about 9 months, for about 10 months, for about 11 months, for about 12 months, for about 18 months, for about 36 months, for about 1 year, for about 2 years, for about 3 years, for about 4 years, for about 5 years, for 6 about years, or for any suitable period of time.

In one embodiment, the invention relates to a light stable testosterone ester, wherein the concentration of available testosterone ester is at least 66.8% to 75.0% of the initial testosterone ester concentration. In some embodiments, the concentration of available testosterone ester at any time after the initial formulation was made is at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the initial testosterone ester concentration.

In some embodiments, the invention relates to a light stable testosterone ester including a testosterone ester adduct of any one of Formulas 3 to 22, wherein the concentration of the testosterone ester adduct in the formulation is less than the concentration of available testosterone ester at any time after the initial formulation is made.

In one embodiment, the invention relates to a method of measuring the light stability of a testosterone ester pharmaceutical formulation including a testosterone ester of Formula 1, and a pharmaceutically acceptable carrier including one or more triglycerides of Formula 2, the method including the steps of measuring the initial testosterone ester concentration in the formulation, after a period of time, measuring the concentration of available testosterone ester in the formulation, and comparing the two concentrations, wherein $R_1$ is an alkyl or alkenyl substituent, and each of $R_2$, $R_3$, and $R_4$ is an acyl group corresponding to a fatty acid such as linoleic acid, oleic acid, palmitic acid, ricinoleic acid, linolenic acid, and/or stearic acid. In some embodiments, the method further includes exposing the pharmaceutical formulation to UV light at 200 watt hours/square meter and visible light exposure of not less than 1.2 million lux hours. Light stability can also be determined after exposing the pharmaceutical formulations to ambient light for a period of time, or to UV light and/or visible light amounts which are equivalents to exposure to ambient light for a period of time. In some embodiments, the pharmaceutical formulation further includes an antioxidant such as butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium. In some embodiments, the period of time is between 30 and 60 days. In some embodiments, the method further includes detecting the presence and measuring the concentration of a testosterone ester adduct of any one of Formulas 3 to 22 in the pharmaceutical formulation.

Measuring the concentration of available testosterone ester in the formulation can be assessed at any time after the initial formulation is made. For example, the concentration of available testosterone ester in the formulation can be assessed after about 1 hour, after about 2 hours, after about 3 hours, after about 4 hours, after about 5 hours, after 6 about hours, after about 7 hours, after about 8 hours, after about 9 hours, after about 10 hours, after about 11 hours, after about 12 hours, after about 13 hours, after about 14 hours, after about 15 hours, after about 16 hours, after about 17 hours, after about 18 hours, after about 19 hours, after about 20 hours, after about 21 hours, after about 22 hours, after about 23 hours, or after about 24 hours.

The concentration of available testosterone ester in the formulation can also be assessed after about 1 day, after about 2 days, after about 3 days, after about 4 days, after about 5 days, after 6 about days, after about 7 days, after about 8 days, after about 9 days, after about 10 days, after about 15 days, after about 20 days, after about 25 days, after about 30 days, after about 35 days, after about 40 days, after about 45 days, after about 50 days, after about 55 days, after about 60 days, after about 90 days, after about 120 days, or after about 180 days.

The concentration of available testosterone ester in the formulation can also be assessed after about 1 week, after about 2 weeks, after about 3 weeks, after about 4 weeks, after about 5 weeks, after 6 about weeks, after about 7 weeks, after about 8 weeks, after about 9 weeks, or after about 10 weeks. Light stability can also be assessed after about 1 month, after about 2 months, after about 3 months, after about 4 months, after about 5 months, after 6 about months, after about 7 months, after about 8 months, after about 9 months, after about 10 months, after about 11 months, after about 12 months, after about 18 months, or after about 36 months. Light stability can also be assessed after about 1 year, after about 2 years, after about 3 years, after about 4 years, after about 5 years, after 6 about years, or any number of years after the initial formulation was made.

The concentration of available testosterone ester in the formulation can also be determined after exposing the pharmaceutical formulations to ambient light, or to UV light and/or visible light amounts which are equivalents to exposure to ambient light for about 1 hour, for about 2 hours, for about 3 hours, for about 4 hours, for about 5 hours, for about 6 hours, for about 7 hours, for about 8 hours, for about 9 hours, for about 10 hours, for about 11 hours, for about 12 hours, for about 13 hours, for about 14 hours, for about 15 hours, for about 16 hours, for about 17 hours, for about 18 hours, for about 19 hours, for about 20 hours, for about 21 hours, for about 22 hours, for about 23 hours, for about 24 hours, or the like.

The concentration of available testosterone ester in the formulation can also be determined after exposing the pharmaceutical formulations to ambient light, or to UV light and/or visible light amounts which are equivalents to exposure to ambient light for about 1 day, for about 2 days, for about 3 days, for about 4 days, for about 5 days, for 6 about days, for about 7 days, for about 8 days, for about 9 days, for about 10 days, for about 15 days, for about 20 days, for about 25 days, for about 30 days, for about 35 days, for about 40 days, for about 45 days, for about 50 days, for about 55 days, for about 60 days, for about 90 days, for about 120 days, or for about 180 days, or the like.

The concentration of available testosterone ester in the formulation can also be determined after exposing the pharmaceutical formulations to ambient light, or to UV light and/or visible light amounts which are equivalents to exposure to ambient light for about 1 week, for about 2 weeks, for about 3 weeks, for about 4 weeks, for about 5 weeks, for 6 about weeks, for about 7 weeks, for about 8 weeks, for about 9 weeks, for about 10 weeks, for about 1 month, for about 2 months, for about 3 months, for about 4 months, for about 5 months, for 6 about months, for about 7 months, for about 8 months, for about 9 months, for about 10 months, for about 11 months, for about 12 months, for about 18 months, for about 36 months, for about 1 year, for about 2 years, for about 3 years, for about 4 years, for about 5 years, for 6 about years, or for any suitable period of time.

Pharmaceutical Compositions

In some embodiments, the concentration of the testosterone ester described herein is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the testosterone ester described herein is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the testosterone ester described herein is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical formulations described herein.

In some embodiments, the concentration of the testosterone ester described herein is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical formulations described herein.

In some embodiments, the amount of each of the active and/or inactive pharmaceutical ingredients provided in the pharmaceutical compositions of the invention, such as a testosterone ester, a triglyceride, and/or an antioxidant, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g in a pharmaceutical formulation described herein.

In some embodiments, the amount of each of the active and/or inactive pharmaceutical ingredients provided in the pharmaceutical compositions of the invention, such as a testosterone ester, a triglyceride, and/or an antioxidant, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g in a pharmaceutical formulation described herein.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. Effective dosages from 50 to 200 mg per week are also examples of dosages that may be used. In one embodiment, the effective weekly dosage is about 50 mg. In one embodiment, the effective weekly dosage is about 100 mg. In one embodiment, the effective weekly dosage is about 150 mg. In one embodiment, the effective weekly dosage is about 200 mg. In one embodiment, the effective weekly dosage is about 250 mg.

The exact dosage will depend upon the route of administration, the form in which the compound is administered, the gender and age of the subject to be treated, the body weight of the subject to be treated, and the preference and experience of the attending physician. The clinically-established dosages of testosterone ester, for example testosterone enanthate, may also be used if appropriate.

In some embodiments, the amount of testosterone ester adduct in a formulation, for example the amount of testosterone enanthate adduct, relative to the amount of testosterone ester in the formulation, for example the amount of testosterone enanthate, is less than about 0.001% (w/w), about 0.001% (w/w), about 0.002% (w/w), about 0.003% (w/w), about 0.004% (w/w), about 0.005% (w/w), about 0.006% (w/w), about 0.007% (w/w), about 0.008%, (w/w) about 0.009% (w/w), about 0.01% (w/w), about 0.015% (w/w), about 0.02% (w/w), about 0.025% (w/w), about 0.03% (w/w), about 0.035% (w/w), about 0.04% (w/w), about 0.045% (w/w), about 0.05% (w/w), about 0.055% (w/w), about 0.06% (w/w), about 0.065% (w/w), about 0.07% (w/w), about 0.075% (w/w), about 0.08% (w/w), about 0.085% (w/w), about 0.09% (w/w), about 0.095% (w/w), about 0.1% (w/w), about 0.15% (w/w), about 0.2% (w/w), about 0.25% (w/w), about 0.3% (w/w), about 0.35% (w/w), about 0.4% (w/w), about 0.45% (w/w), about 0.5% (w/w), about 0.55% (w/w), about 0.6% (w/w), about 0.65% (w/w), about 0.7% (w/w), about 0.75% (w/w), about 0.8% (w/w), about 0.85% (w/w), about 0.9% (w/w), about 0.95% (w/w), about 1% (w/w), or more than about 1% (w/w).

In some embodiments, the lower limit of quantitation of the testosterone ester adduct relative to the total level of testosterone ester is 0.1%. In some embodiments, the lower limit of quantitation of the testosterone adduct relative to the total level of testosterone is 0.1%.

In some embodiments, the amount of testosterone ester adduct in a formulation, for example the amount of testosterone enanthate adduct, relative to the amount of testosterone ester in the formulation, for example the amount of testosterone enanthate, is about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), about 30% (w/w), about 31% (w/w), about 32% (w/w), about 33% (w/w), about 34% (w/w), about 35% (w/w), about 36% (w/w), about 37% (w/w), about 38% (w/w), about 39% (w/w), about 40% (w/w), about 41% (w/w), about 42% (w/w), about 43% (w/w), about 44% (w/w), about 45% (w/w), about 46% (w/w), about 47% (w/w), about 48% (w/w), about 49% (w/w), or about 50% (w/w).

In some embodiments, the concentration of optionally testosterone enanthate adduct in the formulation ranges from 0.000 mg/mL to 25 mg/ml, 0.005 mg/mL to 25 mg/mL, from 0.025 mg/mL to 37.5 mg/mL, from 0.05 mg/mL to 50 mg/mL, from 0.075 mg/mL to 62.5 mg/mL, from 0.1 mg/mL to 75 mg/mL, from 0.125 mg/mL to 100 mg/mL, from 0.175 mg/mL to 125 mg/mL, from 0.2 mg/mL to 175 mg/mL, from 0.25 mg/mL to 200 mg/mL, or from 0.275 mg/mL to 250 mg/mL. In some embodiments, the concentration of testosterone enanthate adduct ranges from 0.005 mg/mL to 100 mg/mL.

In some embodiments, the concentration of testosterone enanthate adduct is about 0.005 mg/mL. In some embodiments, the concentration of testosterone enanthate adduct is about 0.0075 mg/mL. In some embodiments, the concentration of testosterone enanthate adduct is about 0.01 mg/mL. In some embodiments, the concentration of testosterone enanthate adduct is about 0.0125 mg/mL. In some embodiments, the concentration of testosterone enanthate adduct is about 0.015 mg/mL. In some embodiments, the concentration of testosterone enanthate adduct is about 0.0175 mg/mL. In some embodiments, the concentration of testosterone enanthate adduct is about 0.02 mg/mL. In some embodiments, the concentration of testosterone enanthate adduct is about 0.0225 mg/mL. In some embodiments, the concentration of testosterone enanthate is about 0.0250 mg/mL.

In some embodiments, the concentration of testosterone enanthate adduct is about 0.05 mg/mL. In some embodiments, the concentration of testosterone enanthate adduct is about 0.075 mg/mL. In some embodiments, the concentration of testosterone enanthate adduct is about 0.1 mg/mL. In some embodiments, the concentration of testosterone enanthate adduct is about 0.125 mg/mL. In some embodiments, the concentration of testosterone enanthate adduct is about 0.15 mg/mL. In some embodiments, the concentration of testosterone enanthate adduct is about 0.175 mg/mL. In some embodiments, the concentration of testosterone enanthate adduct is about 0.2 mg/mL. In some embodiments, the concentration of testosterone enanthate adduct is about 0.225 mg/mL. In some embodiments, the concentration of testosterone enanthate is about 0.250 mg/mL.

In some embodiments, the concentration of testosterone enanthate adduct is about 0.5 mg/mL. In some embodiments, the concentration of testosterone enanthate adduct is about 0.75 mg/mL. In some embodiments, the concentration of testosterone enanthate adduct is about 1 mg/mL. In some embodiments, the concentration of testosterone enanthate adduct is about 1.25 mg/mL. In some embodiments, the concentration of testosterone enanthate adduct is about 1.5 mg/mL. In some embodiments, the concentration of testosterone enanthate adduct is about 1.75 mg/mL. In some embodiments, the concentration of testosterone enanthate adduct is about 2 mg/mL. In some embodiments, the concentration of testosterone enanthate adduct is about 2.25 mg/mL. In some embodiments, the concentration of testosterone enanthate is about 2.50 mg/mL. In some embodiments, the concentration of testosterone enanthate adduct is about 2.75 mg/mL. In some embodiments, the concentration of testosterone enanthate is about 3 mg/mL. In some embodiments, the concentration of testosterone enanthate adduct is about 3.25 mg/mL. In some embodiments, the concentration of testosterone enanthate is about 3.50 mg/mL. In some embodiments, the concentration of testosterone enanthate adduct is about 3.75 mg/mL. In some embodiments, the concentration of testosterone enanthate is about 4 mg/mL. In some embodiments, the concentration of testosterone enanthate adduct is about 4.25 mg/mL. In some embodiments, the concentration of testosterone enanthate is about 4.50 mg/mL. In some embodiments, the concentration of testosterone enanthate adduct is about 4.75 mg/mL. In some embodiments, the concentration of testosterone enanthate is about 5 mg/mL.

In some embodiments, the concentration of testosterone enanthate ranges from 50 mg/mL to 200 mg/mL. In some embodiments, the concentration of BHT ranges from 0.01% to 0.1%. In some embodiments, the concentration of BHT ranges from 0.1 mg/mL to 1 mg/mL. In some embodiments, the concentration of tocopherol ranges from 0.1% to 5%.

In some embodiments, the concentration of testosterone enanthate ranges from 5 mg/mL to 50 mg/mL, from 25 mg/mL to 75 mg/mL, from 50 mg/mL to 100 mg/mL, from 75 mg/mL to 125 mg/mL, from 100 mg/mL to 150 mg/mL, from 125 mg/mL to 200 mg/mL, from 175 mg/mL to 250 mg/mL, from 200 mg/mL to 350 mg/mL, from 250 mg/mL to 400 mg/mL, or from 275 mg/mL to 500 mg/mL. In some embodiments, the concentration of testosterone enanthate ranges from 50 mg/mL to 200 mg/mL. In some embodiments, the concentration of testosterone enanthate is about 50 mg/mL. In some embodiments, the concentration of testosterone enanthate is about 75 mg/mL. In some embodiments, the concentration of testosterone enanthate is about 100 mg/mL. In some embodiments, the concentration of testosterone enanthate is about 125 mg/mL. In some embodiments, the concentration of testosterone enanthate is about 150 mg/mL. In some embodiments, the concentration of testosterone enanthate is about 175 mg/mL. In some embodiments, the concentration of testosterone enanthate is about 200 mg/mL. In some embodiments, the concentration of testosterone enanthate is about 225 mg/mL. In some embodiments, the concentration of testosterone enanthate is about 250 mg/mL.

In some embodiments, the concentration of BHT ranges from 0.01% to 0.025%, from 0.015% to 0.05%, from 0.035% to 0.075%, from 0.05% to 0.085%, from 0.06% to 0.095%, or from 0.075% to 0.1%. In some embodiments, the concentration of BHT ranges from 0.075% to 0.15%, from 0.1% to 0.25%, or from 0.15% to 0.5%. In some embodiments, the concentration of BHT ranges from 0.01% to 0.1%. In some embodiments, the concentration of BHT ranges from 0.1 mg/mL to 1 mg/mL, from 0.25 mg/mL to 0.5 mg/mL, from 0.35 mg/mL to 0.75 mg/mL, from 0.5 mg/mL to 1.5 mg/mL, or from 1 mg/mL to 5 mg/mL. In some embodiments, the concentration of tocopherol ranges from 0.1% to 1%, from 0.25% to 2.5%, from 1% to 10%. In some embodiments, the concentration of tocopherol ranges from 0.1% to 5%.

In one embodiment, the invention relates to pharmaceutical formulation including testosterone enanthate, sesame oil, BHT, and one or more testosterone adduct of Formulas 3 to 22. In some embodiments, the adduct has Formula 10. In some embodiments, the adduct has Formula 11. In some embodiments, the concentration of testosterone enanthate is from 50 mg/mL to 200 mg/mL, or from 5 mg/mL to 500 mg/mL. In some embodiments, the concentration of BHT is from 0.01% to 0.1%, from 0.01% to 1%, from 0.1 mg/mL to 1 mg/mL, or from 0.1 mg/mL to 10 mg/mL. In some embodiments, the concentration of a testosterone ester adduct is less than the concentration of testosterone enanthate. In some embodiments, the total concentration of testosterone ester adducts is less than the concentration of testosterone enanthate.

Formulations of 100 mg/ml, 150 mg/ml and 200 mg/ml testosterone ester (e.g., testosterone enanthate) can each be formulated in USP oil (e.g., sesame oil) containing 0.07-1.0% antioxidant (e.g., BHT) and optionally further including an adduct of the present invention.

Other Testosterone or Testosterone Derivative Adducts

This disclosure is not limited to testosterone ester adducts with mono-, di-, and/or triglycerides, and includes any testosterone derivative adduct with a mono-, di-, and/or triglyceride, including adducts of testosterone with a mono-, di-, and/or triglyceride. All methods and conditions of occurring, making, controlling, or using testosterone ester adducts described herein are equally applicable to these other testosterone or testosterone derivative adducts.

In some embodiments, the invention relates to a testosterone or testosterone derivative adduct of Formula 23:

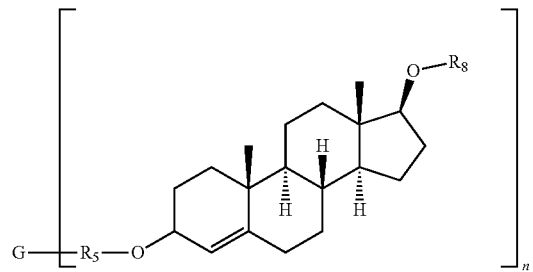

Formula 23 wherein $R_8$ is independently at each occurrence hydrogen, or any suitable substituent described herein or known in the art for testosterone, $R_5$ is an acyl group corresponding to an unsaturated fatty acid, G is a glycerol, monoglyceride, or diglyceride residue, n is 1, 2, or 3, and the testosterone residue is connected to an allylic or doubly allylic carbon of $R_5$.

In some embodiments, the testosterone or testosterone derivative adduct has Formula 24:

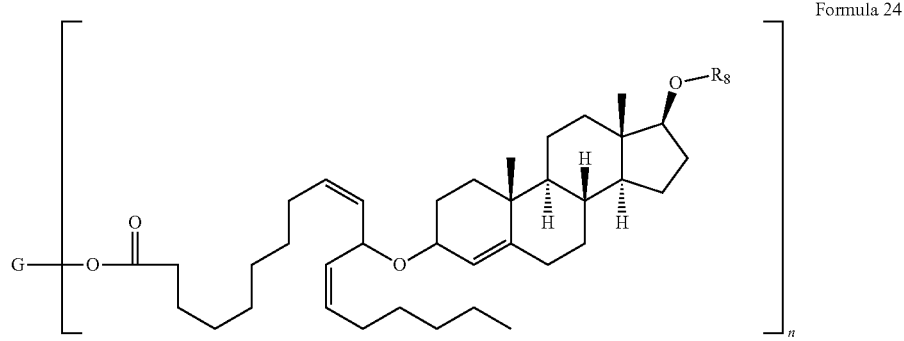

Formula 24 wherein $R_8$ is independently at each occurrence hydrogen, or any suitable substituent described herein or known in the art for testosterone, G is a glycerol, monoglyceride, or diglyceride residue, and n is 1, 2, or 3.

In some embodiments, the invention relates to a testosterone or testosterone derivative adduct of any one of Formulas 25 to 29:

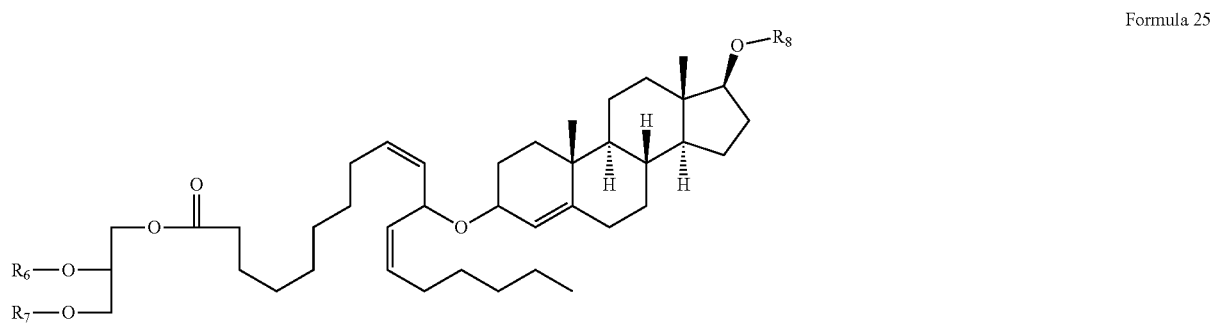

Formula 25

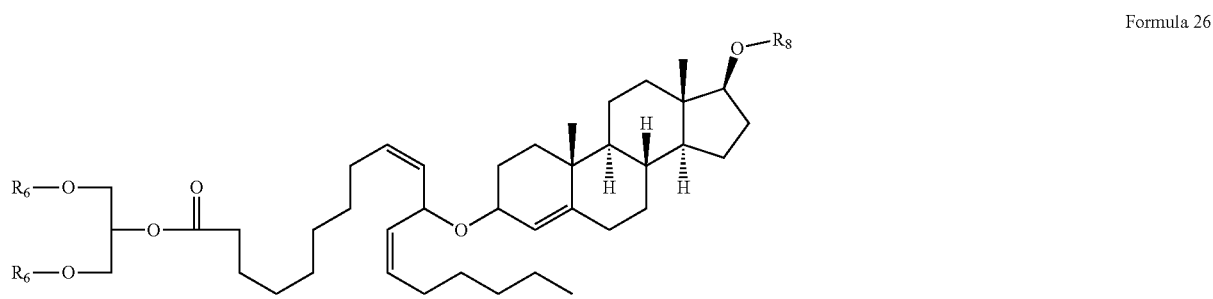

Formula 26

Formula 27
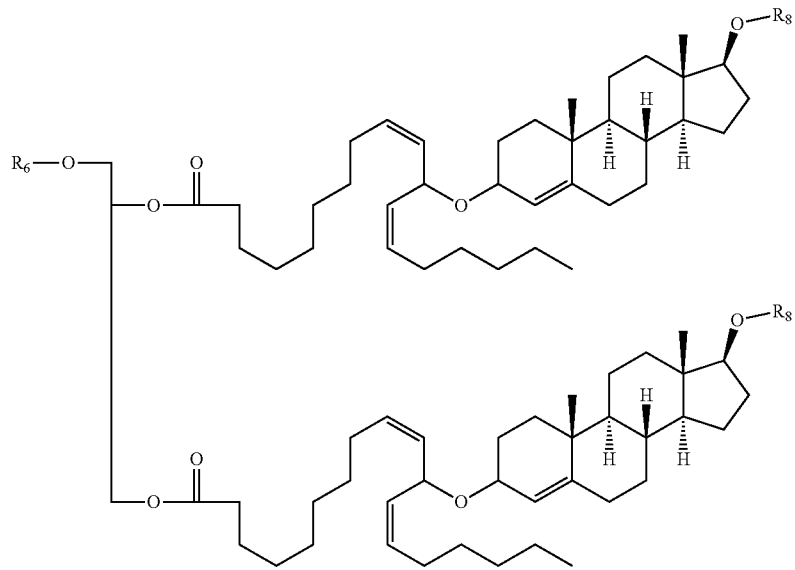
Formula 28
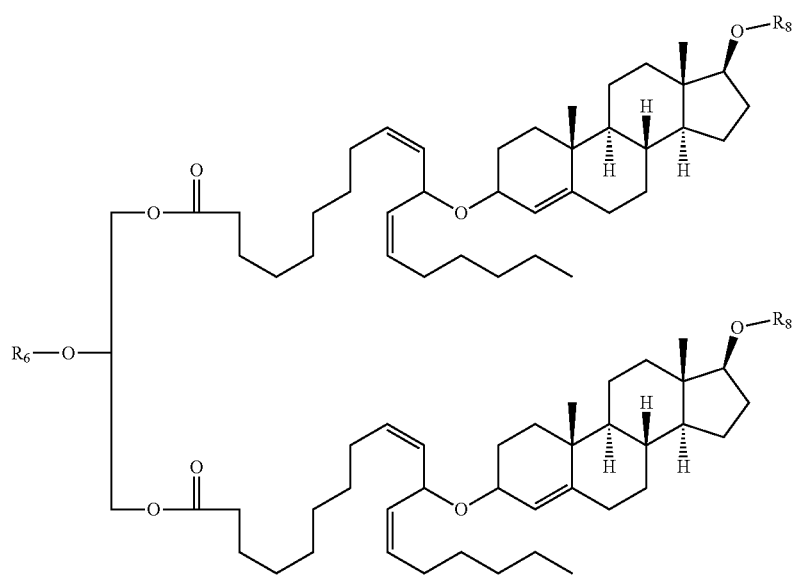

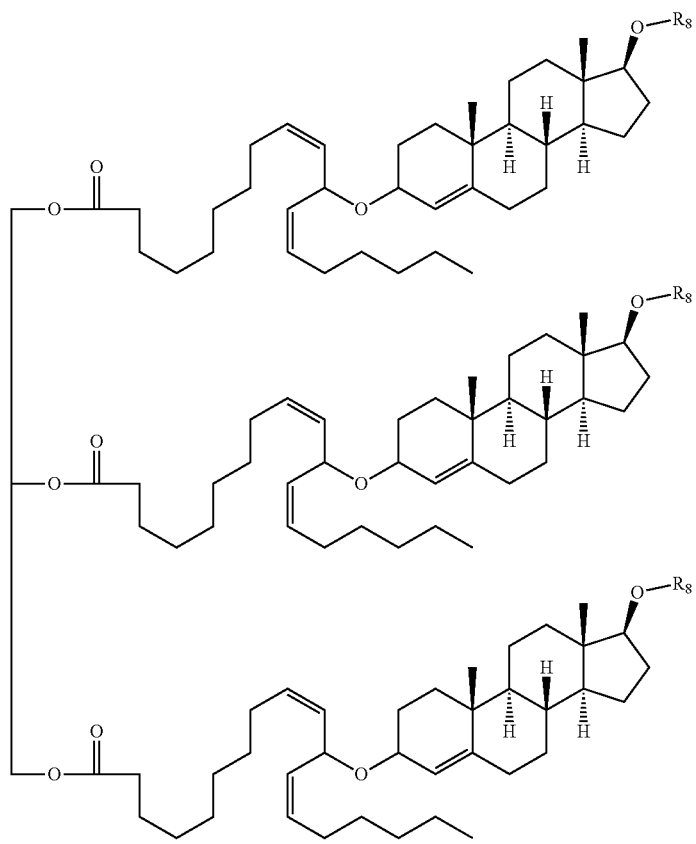

Formula 29 wherein $R_8$ is independently at each occurrence hydrogen, or any suitable substituent described herein or known in the art for testosterone, and each one of $R_6$ and $R_7$ is independently an acyl group corresponding to a fatty acid selected from the group consisting of linoleic acid, oleic acid, palmitic acid, ricinoleic acid, linolenic acid, and stearic acid.

Pharmaceutical Compositions for Injection

In some embodiments, a pharmaceutical composition is provided for injection containing an active pharmaceutical ingredient or combination of active pharmaceutical ingredients, such as a testosterone ester, for example testosterone enanthate, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal preservatives or preservative agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intradermal, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally.

Kits

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit including a composition including a therapeutically effective amount of an active pharmaceutical ingredient (e.g., a testosterone ester) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides for a kit including a composition including a therapeutically effective amount of testosterone ester alone or in combination with active pharmaceutical ingredients or a pharmaceutically acceptable salt, solvate, hydrate, cocrystal, or prodrug in an oil combined with an antioxidant in a prefilled syringe (PFS) or vial. In some embodiments, the prefilled syringe or the vial are transparent. The kit includes suitable packaging for protecting the prefilled syringe or vial from light. In some embodiments this includes an autoinjector. In other embodiments, this includes an autoinjector with a viewing window to allow inspection of the drug prior to injection. In yet other embodiments, the autoinjector is in a carton to prevent light access to the drug.

The prefilled syringe or the vial may include one dose or multiple doses. In some embodiments, a prefilled syringe or vial including multiple doses is bigger, i.e., has a larger volume than a prefilled syringe or vial including only one dose. In some embodiments, the testosterone ester triglyceride adducts described herein form in a prefilled syringe or vial during normal storage, and/or upon exposure to various amounts of light. In some embodiments, the surface area to the volume ratio of a prefilled syringe or vial gets smaller as the prefilled syringe or vial gets larger in volume. Without wishing to be bound by any particular theory, in some embodiments, the testosterone ester triglyceride adducts described herein form in higher amounts, and/or at accelerated rates, when the surface area of the prefilled syringe or vial containing a testosterone ester formulation which is exposed to light is larger. Without wishing to be bound by any particular theory, in some embodiments, the testosterone ester triglyceride adducts described herein form in lower amounts, and/or at slower rates, when the volume of the prefilled syringe or vial containing a testosterone ester formulation which is exposed to light is larger. Without wishing to be bound by any particular theory, in some embodiments, the testosterone ester triglyceride adducts described herein form in higher amounts, and/or at accelerated rates, when the surface to volume ratio of the prefilled syringe or vial containing a testosterone ester formulation which is exposed to light is larger. Without wishing to be bound by any particular theory, in some embodiments, the testosterone ester triglyceride adducts described herein form in lower amounts, and/or at slower rates, when the surface to volume ratio of the prefilled syringe or vial containing a testosterone ester formulation which is exposed to light is smaller.

In some embodiments, the percentage of the initial amount of testosterone ester in a formulation which is preserved upon storage or exposure to light is higher in a larger volume prefilled syringe or vial. In some embodiments, the percentage of the initial amount of testosterone ester in a formulation which is preserved upon storage or exposure to light is higher in a prefilled syringe or vial with a lower surface to volume ratio, compared to a prefilled syringe or vial with a higher surface to volume ratio. In some embodiments, the percentage of the initial amount of testosterone ester in a formulation which is preserved upon storage or exposure to light is higher in a multi dose prefilled syringe or vial compared to a single dose prefilled syringe or vial.

In one embodiment, a prefilled syringe or vial is filled with a formulation including about 50 mg testosterone ester. In one embodiment, a prefilled syringe or vial is filled with a formulation including about 75 mg testosterone ester. In one embodiment, a prefilled syringe or vial is filled with a formulation including about 100 mg testosterone ester. In one embodiment, a prefilled syringe or vial is filled with a formulation including about 125 mg testosterone ester. In one embodiment, a prefilled syringe or vial is filled with a formulation including about 150 mg testosterone ester. In one embodiment, a prefilled syringe or vial is filled with a formulation including about 175 mg testosterone ester. In one embodiment, a prefilled syringe or vial is filled with a formulation including about 200 mg testosterone ester. In one embodiment, a prefilled syringe or vial is filled with a formulation including about 225 mg testosterone ester. In one embodiment, a prefilled syringe or vial is filled with a formulation including about 250 mg testosterone ester. In one embodiment, a prefilled syringe or vial is filled with a formulation including about 275 mg testosterone ester. In one embodiment, a prefilled syringe or vial is filled with a formulation including about 300 mg testosterone ester. In one embodiment, a prefilled syringe or vial is filled with a formulation including any multiples of 25 mg or 50 mg of testosterone ester.

In one embodiment, a prefilled syringe or vial is filled with about 0.1 mL of a formulation including testosterone ester. In one embodiment, a prefilled syringe or vial is filled with about 0.2 mL of a formulation including testosterone ester. In one embodiment, a prefilled syringe or vial is filled with about 0.3 mL of a formulation including testosterone ester. In one embodiment, a prefilled syringe or vial is filled with about 0.4 mL of a formulation including testosterone ester. In one embodiment, a prefilled syringe or vial is filled with about 0.5 mL of a formulation including testosterone ester. In one embodiment, a prefilled syringe or vial is filled with about 0.6 mL of a formulation including testosterone ester. In one embodiment, a prefilled syringe or vial is filled with about 0.7 mL of a formulation including testosterone ester. In one embodiment, a prefilled syringe or vial is filled with about 0.8 mL of a formulation including testosterone ester. In one embodiment, a prefilled syringe or vial is filled with about 0.9 mL of a formulation including testosterone ester. In one embodiment, a prefilled syringe or vial is filled with about 1 mL of a formulation including testosterone ester. In one embodiment, a prefilled syringe or vial is filled with about 1.1 mL of a formulation including testosterone ester. In one embodiment, a prefilled syringe or vial is filled with about 1.2 mL of a formulation including testosterone ester. In one embodiment, a prefilled syringe or vial is filled with about 1.3 mL of a formulation including testosterone ester. In one embodiment, a prefilled syringe or vial is filled with about 1.4 mL of a formulation including testosterone ester. In one embodiment, a prefilled syringe or vial is filled with about 1.5 mL of a formulation including testosterone ester. In one embodiment, a prefilled syringe or vial is filled with about 1.6 mL of a formulation including testosterone ester. In one embodiment, a prefilled syringe or vial is filled with about 1.7 mL of a formulation including testosterone ester. In one embodiment, a prefilled syringe or vial is filled with about 1.8 mL of a formulation including testosterone ester. In one embodiment, a prefilled syringe or vial is filled with about 1.9 mL of a formulation including testosterone ester. In one embodiment, a prefilled syringe or vial is filled with about 2 mL of a formulation including testosterone ester. In one embodiment, a prefilled syringe or vial is filled with about 2.1 mL of a formulation including testosterone ester. In one embodiment, a prefilled syringe or vial is filled with about 2.2 mL of a formulation including testosterone ester. In one embodiment, a prefilled syringe or vial is filled with about 2.3 mL of a formulation including testosterone ester. In one embodiment, a prefilled syringe or vial is filled with about 2.4 mL of a formulation including testosterone ester. In one embodiment, a prefilled syringe or vial is filled with about 2.5 mL of a formulation including testosterone ester. In one embodiment, a prefilled syringe or vial is filled with about 2.6 mL of a formulation including testosterone ester. In one embodiment, a prefilled syringe or vial is filled with about 2.7 mL of a formulation including testosterone ester. In one embodiment, a prefilled syringe or vial is filled with about 2.8 mL of a formulation including testosterone ester. In one embodiment, a prefilled syringe or vial is filled with about 2.9 mL of a formulation including testosterone ester. In one embodiment, a prefilled syringe or vial is filled with about 3 mL of a formulation including testosterone ester.

Such kits may include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider and/or the patient. Such information may instruct the user to keep the prefilled syringe or prefilled syringe and autoinjector in a carton to protect the pharmaceutical ingredients from light. When the kit including a composition including a therapeutically effective amount of testosterone ester alone or in combination with active pharmaceutical ingredients or a pharmaceutically acceptable salt, solvate, hydrate, cocrystal, or prodrug in an oil combined with an antioxidant in a prefilled syringe or prefilled syringe in an autoinjector, the time that the prefilled syringe or autoinjector may be allowed to remain outside the light protecting packaging prior to use may be increased from a similar preparation that does not contain an antioxidant and this information may be reflected in the information provided in the kit.

In some embodiments, the invention provides a kit including (1) a composition including a therapeutically effective amount of an active pharmaceutical ingredient (e.g., a testosterone ester) or combination of active pharmaceutical ingredients or a pharmaceutically acceptable salt, solvate, hydrate, cocrystal, or prodrug thereof, and (2) a diagnostic test for determining whether a patient is in need of testosterone ester administration.

Dosages and Dosing Regimens

The amounts of the pharmaceutical compositions administered using the methods herein, such as the dosages of testosterone esters, will be dependent on the subject, e.g., human or mammal being treated, the severity of the disorder or condition, the rate of administration, the disposition of the active pharmaceutical ingredients and the discretion of the prescribing physician. Dosage in the range of 50 to 100 mg per week for administration to a human may be adequate to achieve an effective therapeutic level. At times, dosages of 50 to 100 mg per week over several weeks may be required to achieve the desired therapeutic level. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/m$^2$ of body surface area.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). Other embodiments require the pharmaceutical composition is administered for more than 1, 2, 3, 4, 5, 6, 7, 14, or 28 week(s). In some embodiments, a pharmaceutical composition is administered for less than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 50 mg to 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 50 mg to about 100 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than about 25 mg, less than about 50 mg, less than about 75 mg, less than about 100 mg, less than about 125 mg, less than about 150 mg, less than about 175 mg, less than about 200 mg, less than about 225 mg, or less than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg. In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect, e.g., by dividing such larger doses into several small doses for administration throughout the day. As those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, intradermally, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

A number of patent and non-patent publications are cited herein in order to describe the state of the art to which this invention pertains. The entire disclosure of each of these publications is incorporated by reference herein.

The following examples describe the invention in further detail. These examples are provided for illustrative purposes only, and should in no way be considered as limiting the invention.

EXAMPLES

Figure 2:
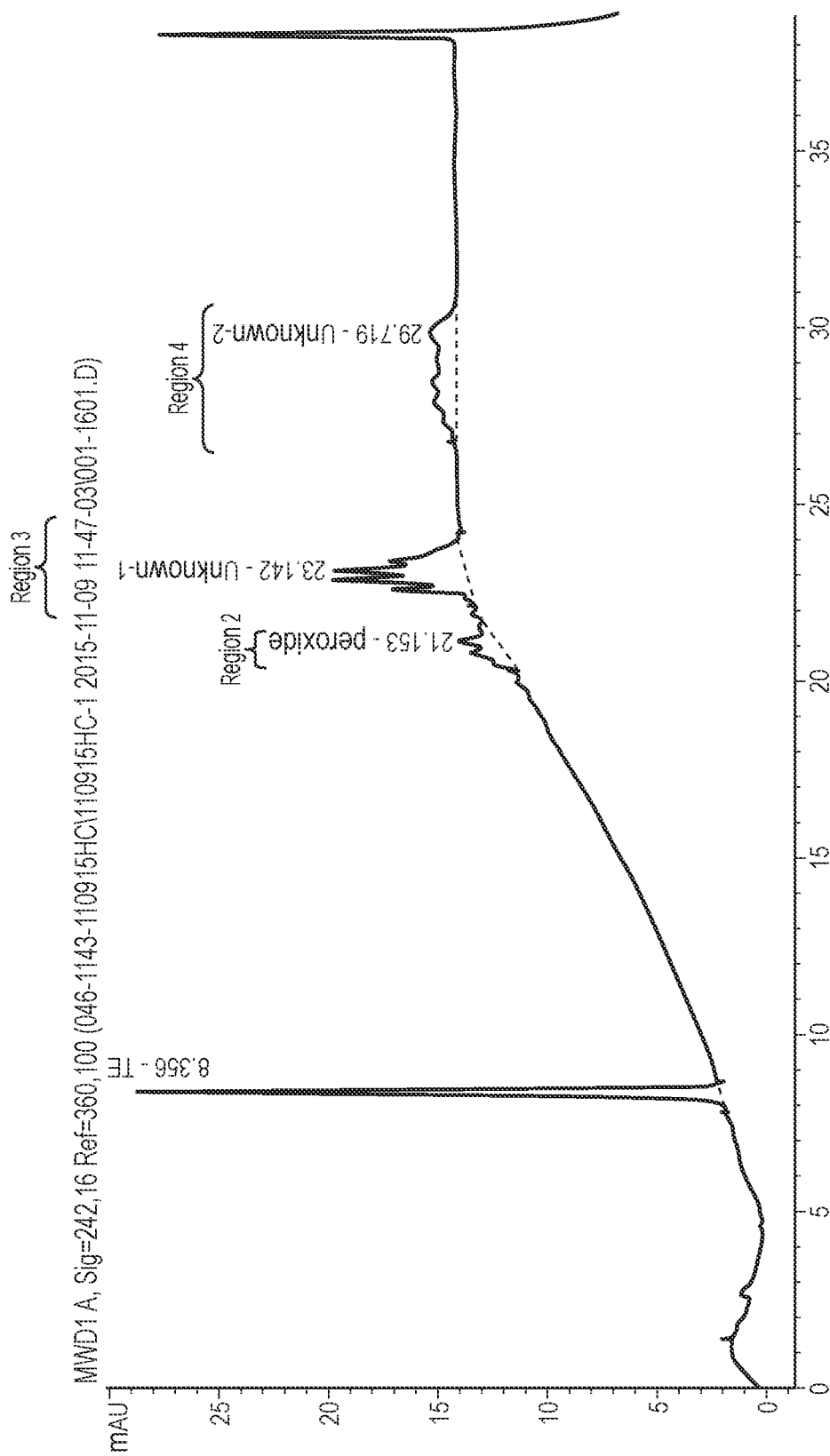
FIG. 2 illustrates a chromatogram of a crude product mix after stress treatment.
Figure 3:
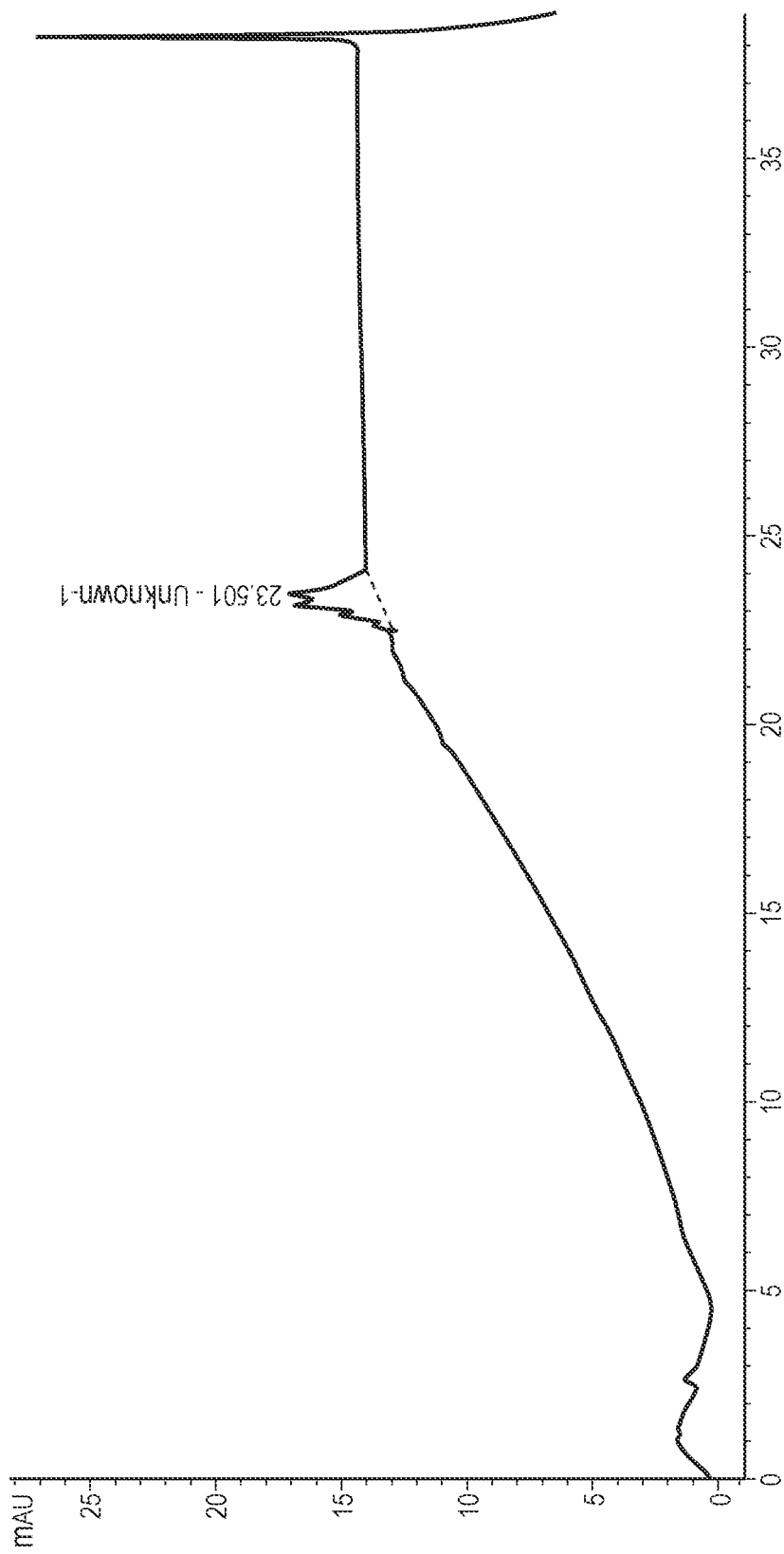
FIG. 3 illustrates a chromatogram of purified fraction 1.
Figure 4:
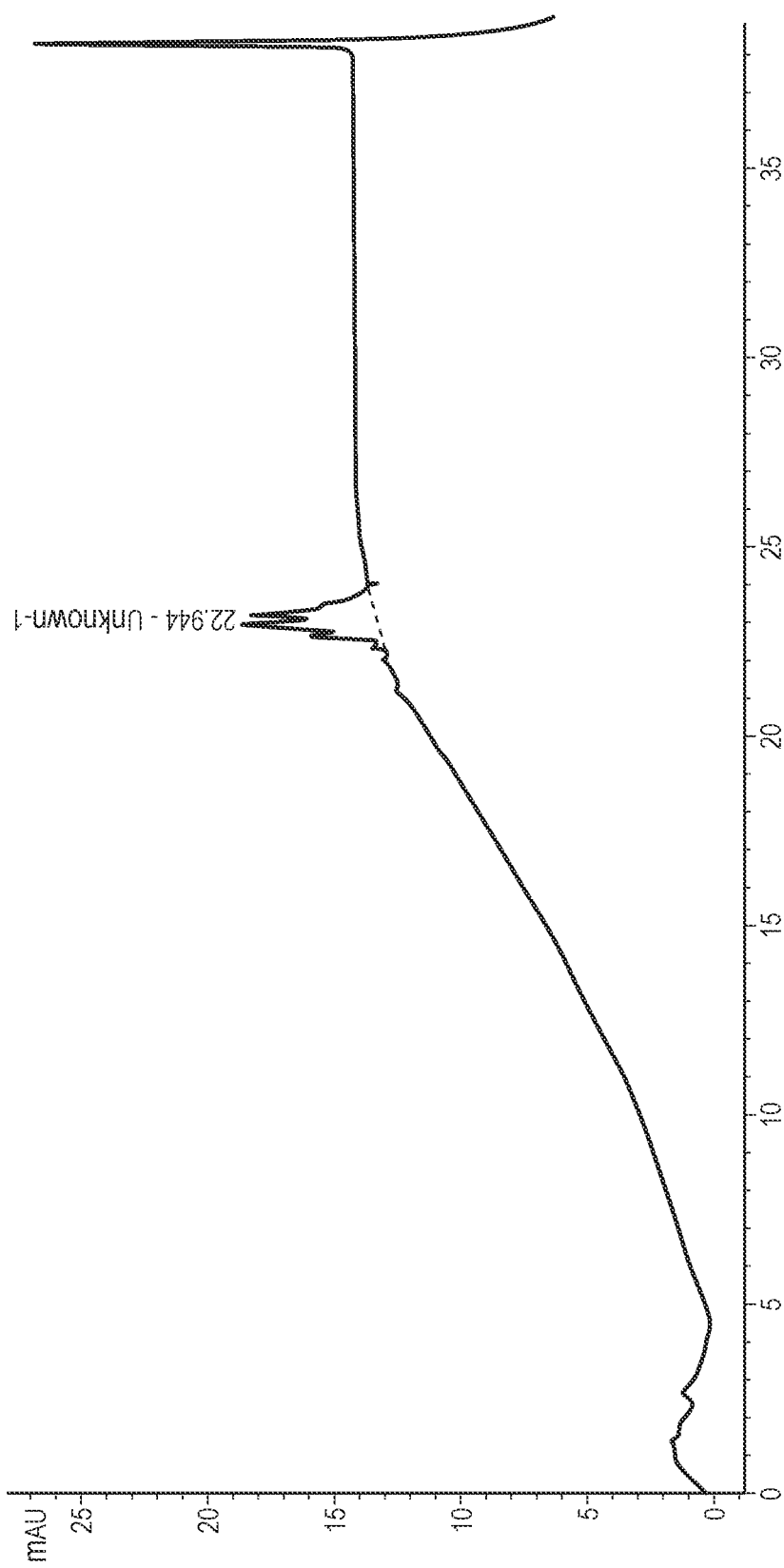
FIG. 4 illustrates a chromatogram of purified fraction 2.
Figure 5:
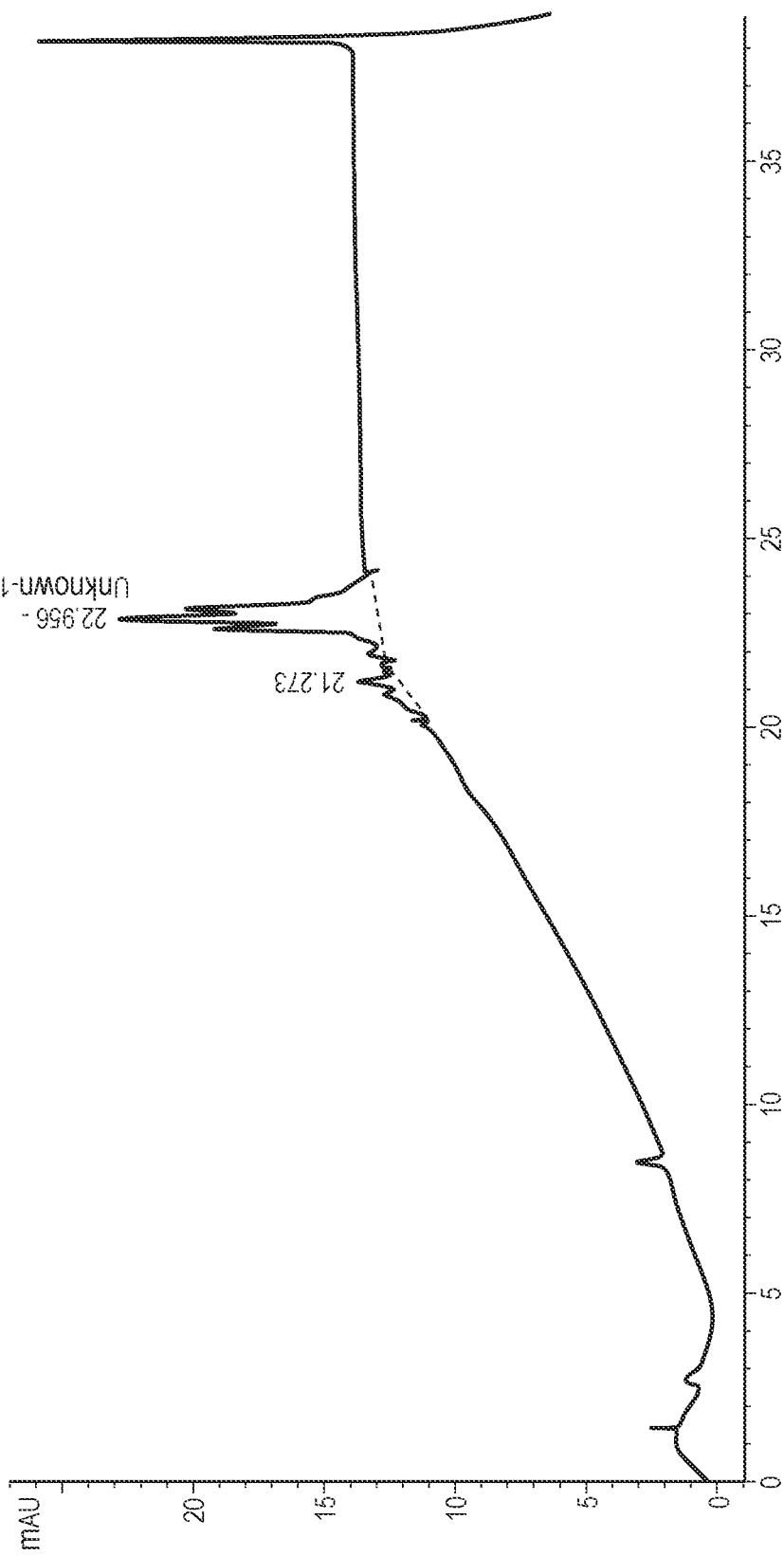
FIG. 5 illustrates a chromatogram of purified fraction 3.
Figure 6:
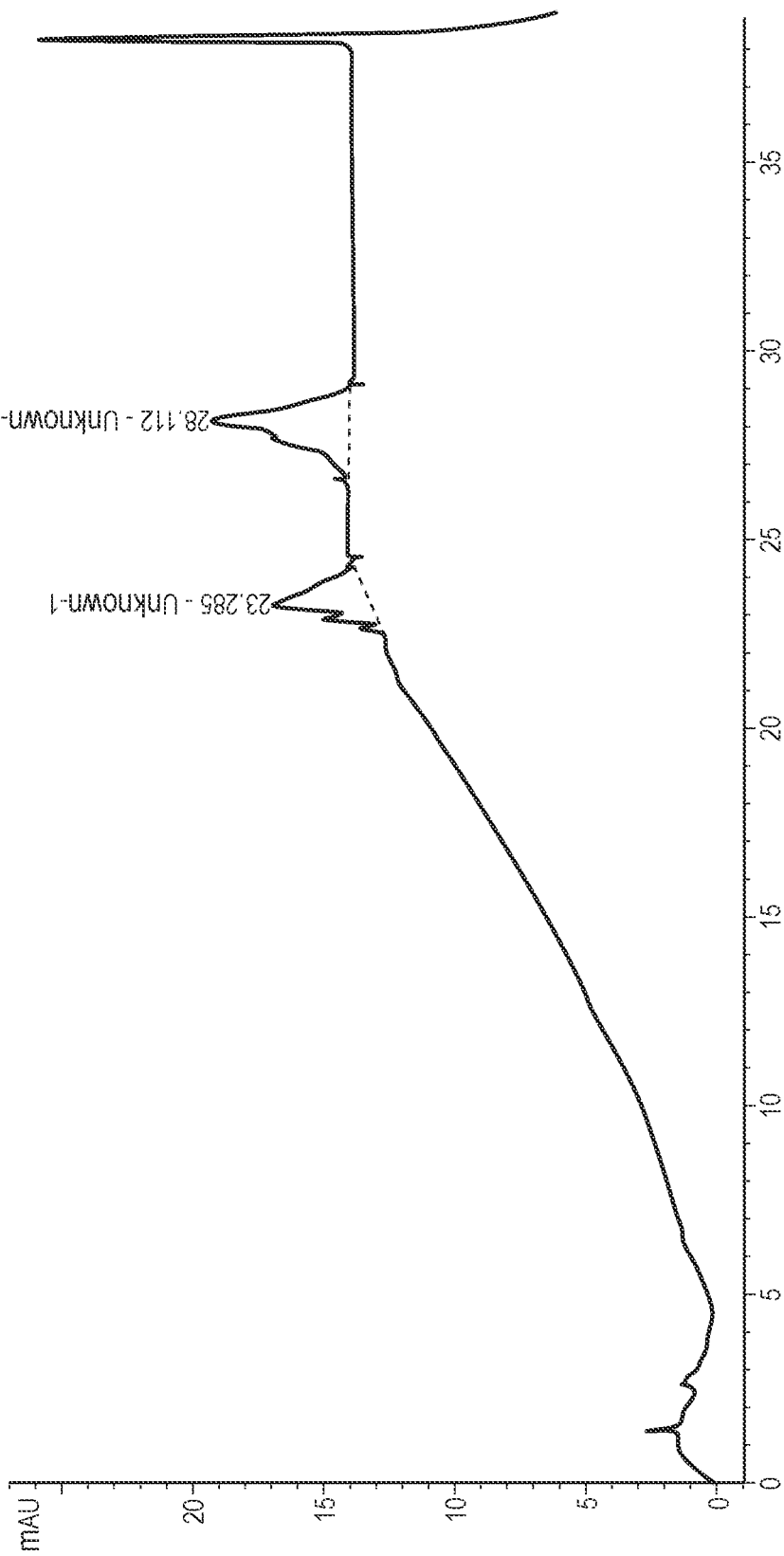
FIG. 6 illustrates a chromatogram of purified fraction 4.

Example 1: Structure Identification of Testosterone Enanthate-Triglyceride Adduct Found in Testosterone—Sesame Oil Mixture after Light Induced Stress A light stress induced product was produced by radiating 200 mg/mL of testosterone enanthate in sesame oil in accordance with ICH recommendation for UV/VIS stress treatment. At the end of stress treatment an aliquot of the crude product was chromatographed using analytical column Synergi Max-RP 80A, 150×4.6 mm, 4 μm with mobile phase A as acetonitrile/water (90/10, v/v) and mobile phase B as 100% ethanol. The results are illustrated in FIG. 2. Preliminary results suggested that peak in region 3 as illustrated in FIG. 1 was where the testosterone enanthate—triglyceride adduct eluted and not region 4.

The crude product was then purified using a preparative chromatography system using a preparative column Synergi Max-RP 80A, AXIA Packed New Column 250×21.2 mm, 4 m and ethanol as mobile phase. Region 3 was collected in several fractions. Each fraction was tested using the chromatographic condition using the analytical column Synergi Max-RP 80A, 150×4.6 mm, 4 μm described above. The chromatograms of the purified fractions are illustrated in FIGS. 3 to 6. Each of these fractions were concentrated to remove the excess ethanol solvent to yield a concentrated purified product. Fractions 1 and 2 were purer than fractions 3 or 4. Since purified product from fraction 1 was the purest, this purified product was used for the testosterone-enanthate structural identification study. The quantity collected from these purified products after evaporation are listed in Table 1.

TABLE 1

Amount of Purified Product

| Amount of Purified Product Fraction Number | Weight after Evaporation (mg) |
|---|---|
| 1 | 587 |
| 2 | 346 |
| 3 | 521 |
| 4 | 49 |

Figure 7:
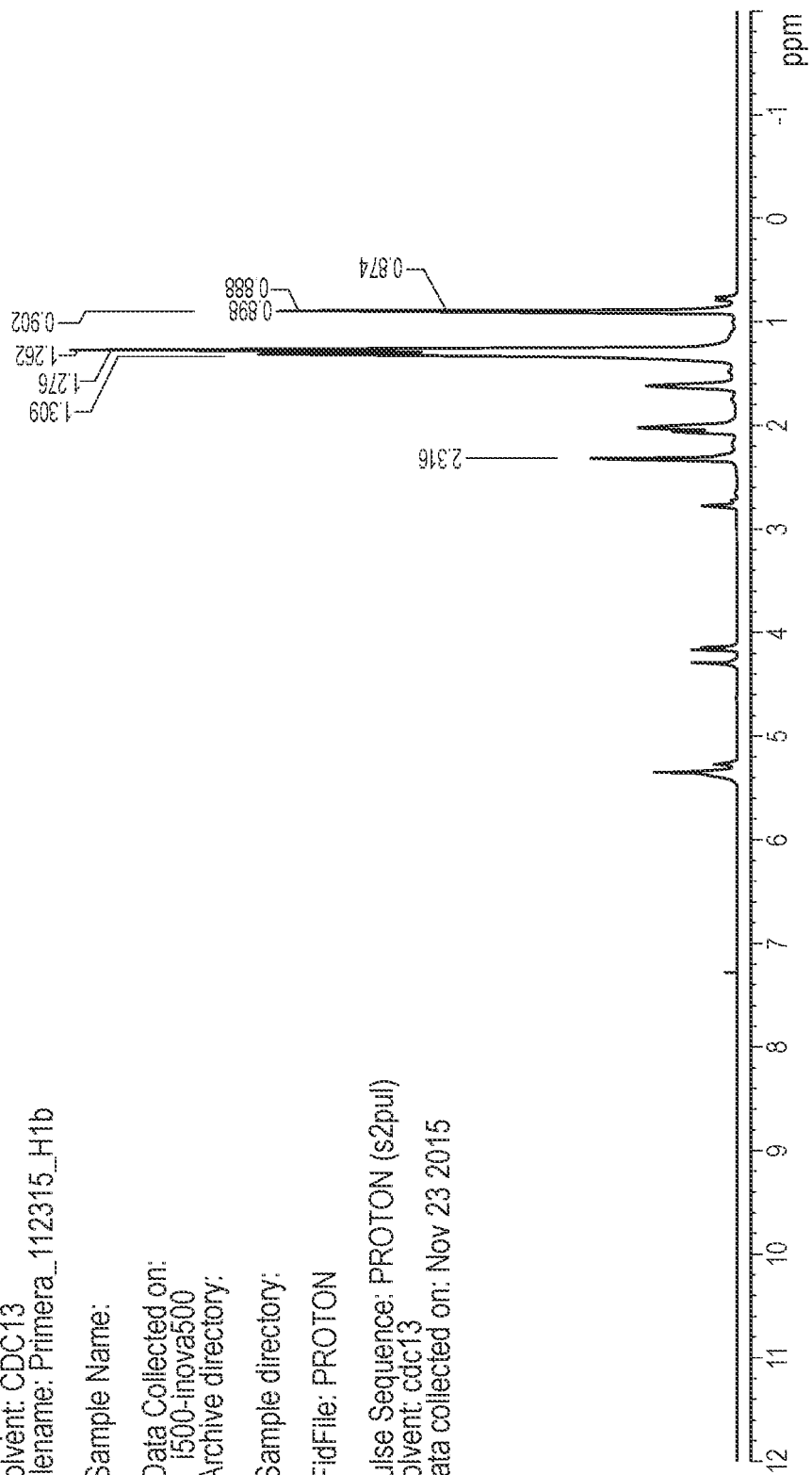
FIG. 7 illustrates the $^1$H NMR spectrum of purified product from fraction 1.
Figure 8:
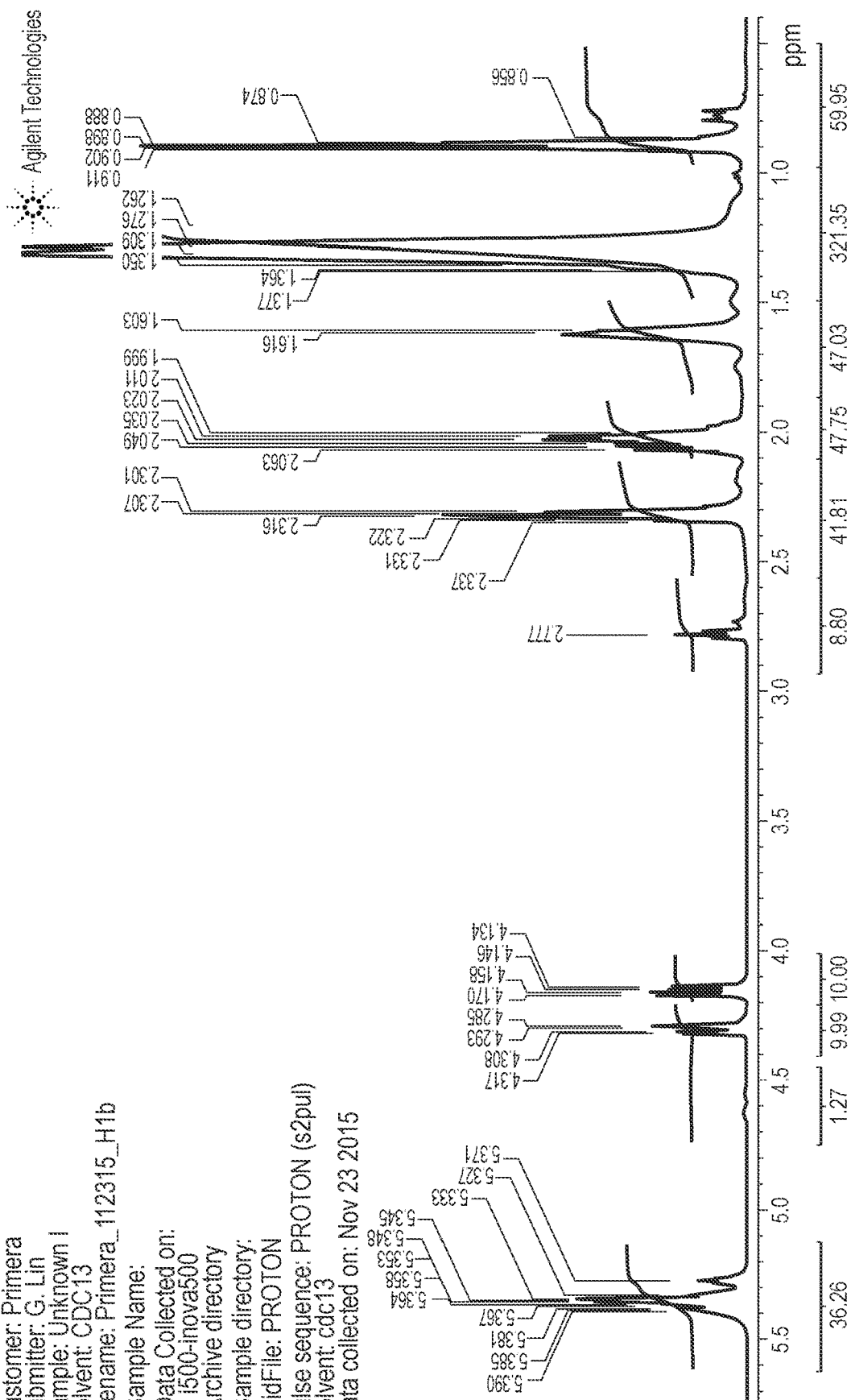
FIG. 8 illustrates the $^1$H NMR spectrum of purified product from fraction 1; the expanded NMR spectrum shows the splitting pattern of the protons of a molecule which is the major component of purified fraction 1.
Figure 9:
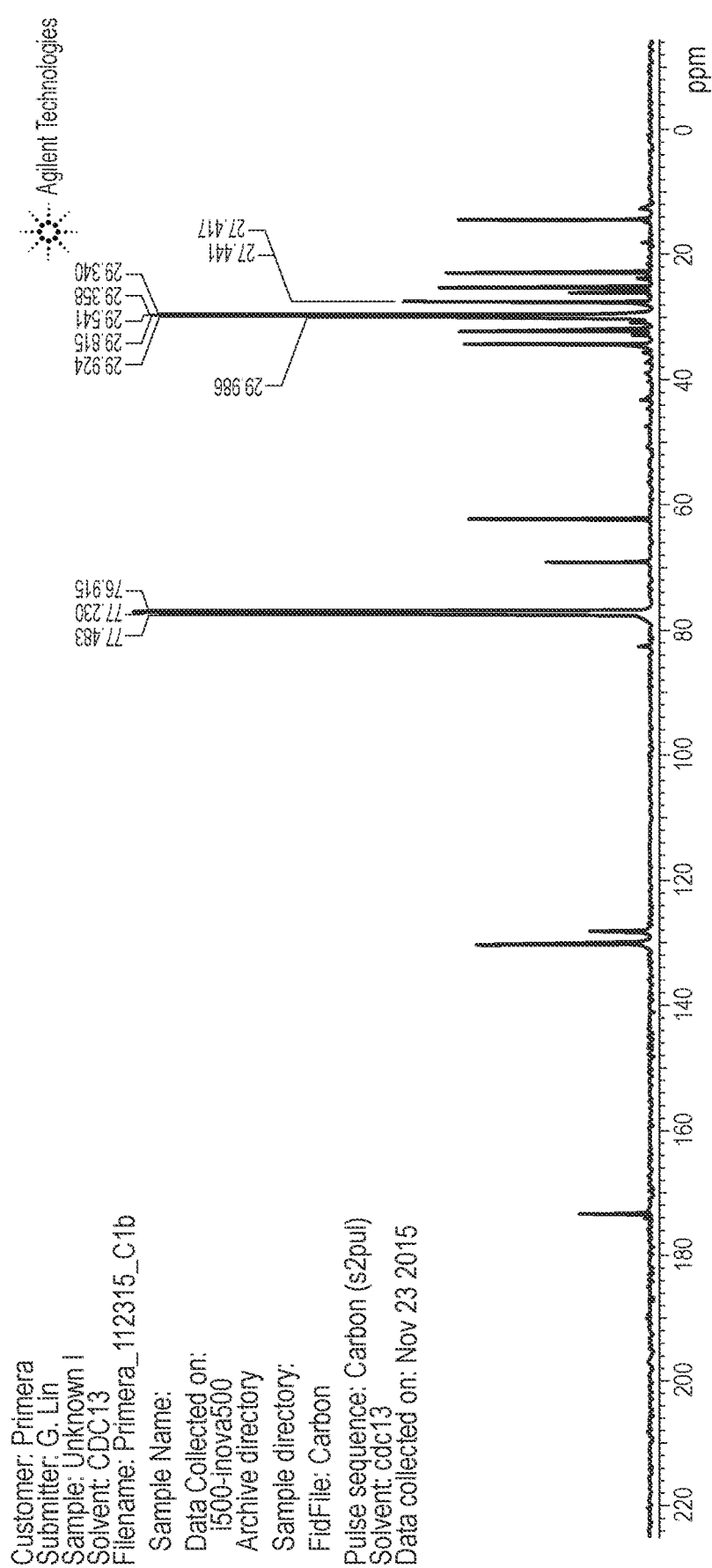
FIG. 9 illustrates the $^{13}$C NMR spectrum of purified product from fraction 1; the absence of $^3$C peak at 205-220 ppm characteristic of a ketone carbonyl (C=O) carbon suggests that the carbonyl carbon of testosterone enanthate had been altered, for example by formation of —C—O—C— bond.
Figure 10:
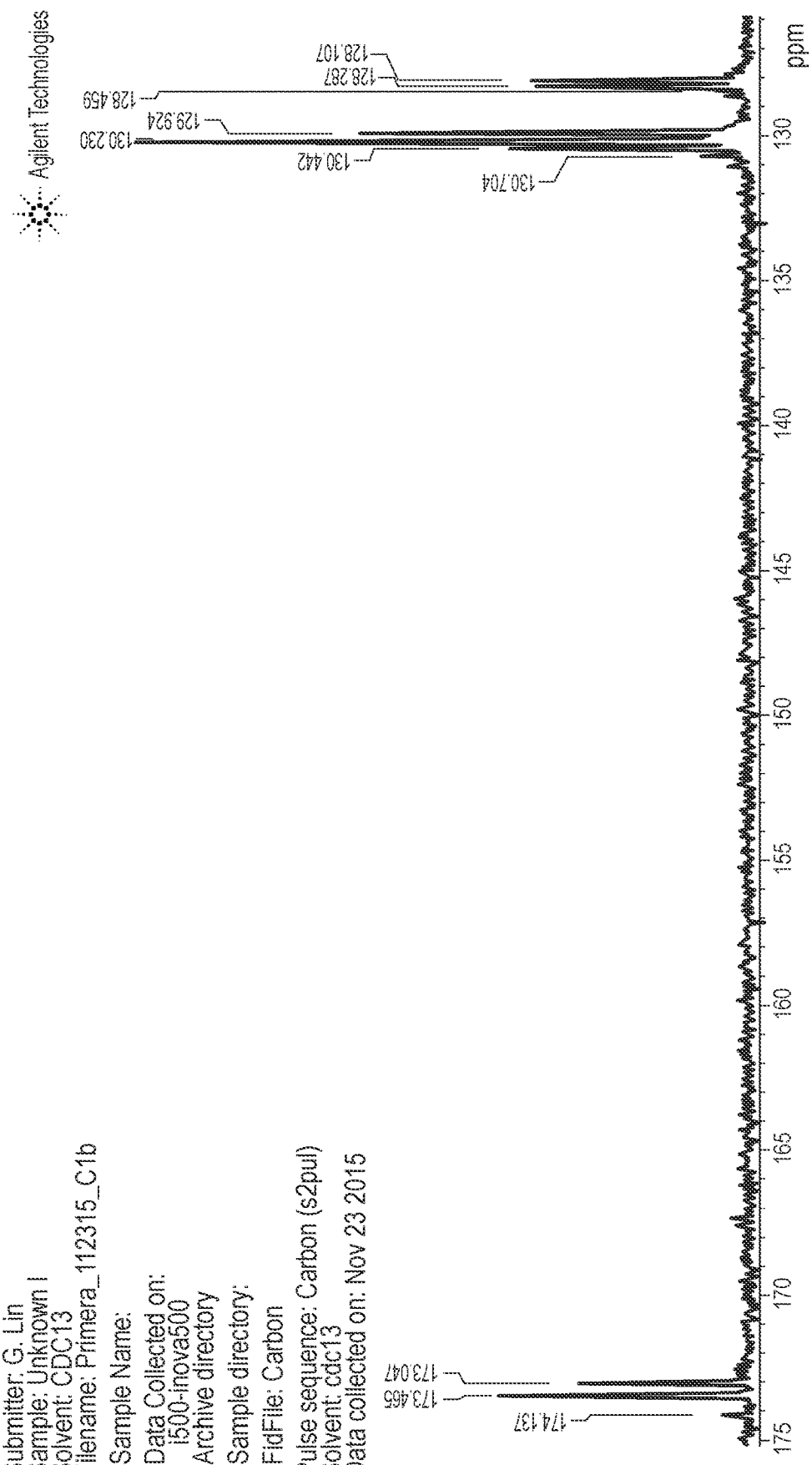
FIG. 10 illustrates the expanded $^{13}$C NMR spectrum of purified product from fraction 1 (130-175 ppm).
Figure 11:
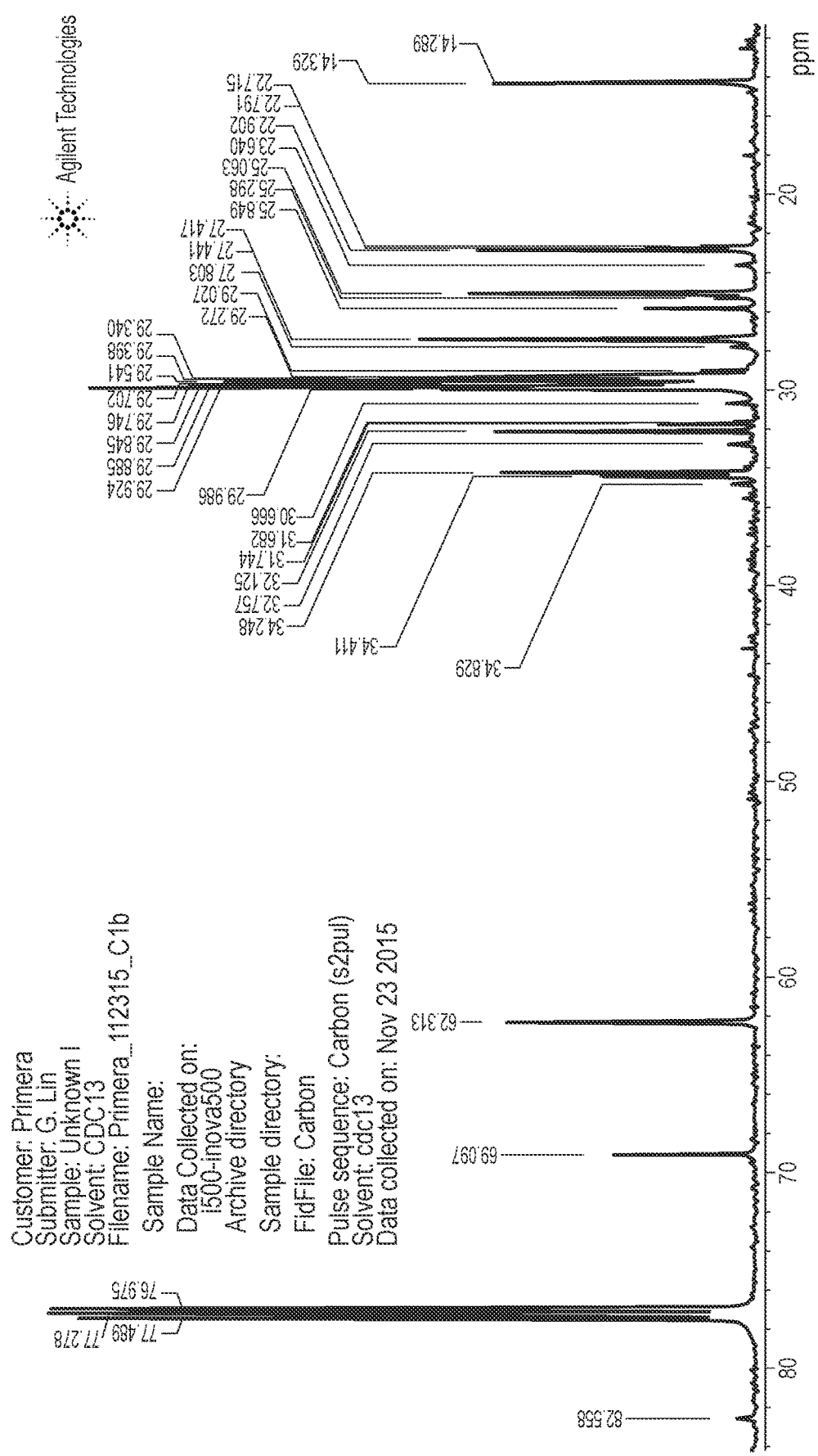
FIG. 11 illustrates the expanded $^{13}$C NMR Spectrum of purified product from fraction 1 (2-84 ppm).
Figure 12:
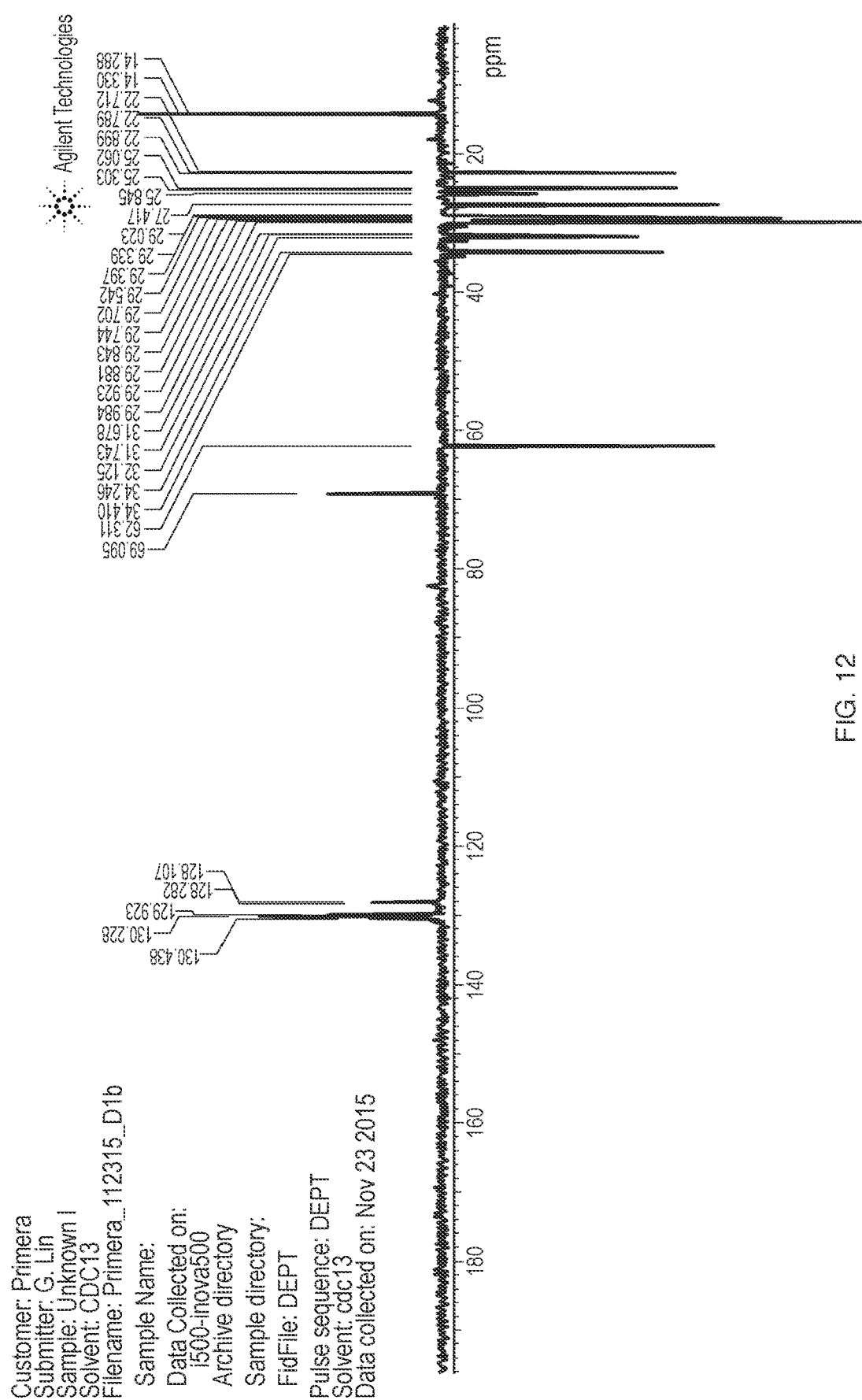
FIG. 12 illustrates the $^{13}$C DEPT NMR spectrum of purified product from fraction 1.

The structural identification study included NMR analysis. FIG. 7 illustrates the $^1$H NMR spectrum of purified product from fraction 1. FIG. 8 illustrates the $^1H$NMR spectrum of purified product from fraction 1; the expanded NMR spectrum shows the splitting pattern of the protons of a molecule which is the major component of purified fraction 1. FIG. 9 illustrates the $^{13}$C NMR spectrum of purified product from fraction 1; the absence of $^{13}$C peak at 205-220 ppm characteristic of a ketone carbonyl (C=O) carbon suggests that the carbonyl carbon of testosterone enanthate had been altered, for example by formation of —C—O—C— bond. FIG. 10 illustrates the expanded $^{13}$C NMR spectrum of purified product from fraction 1 (130-175 ppm). FIG. 11 illustrates the expanded $^{13}$C NMR Spectrum of purified product from fraction 1 (2-84 ppm). FIG. 12 illustrates the $^{13}$C DEPT NMR spectrum of purified product from fraction 1.

The structural identification study further included LC-UV coupled with Mass Spectrometry Analysis. An aliquot of purified fraction 1 was diluted to 10 µg/mL with ethanol and injected into LC-UV system coupled with an API 4000 mass spectrometer using a Synergi Max-RP 80A, 150×4.6 mm, 4 µm with mobile phase A as acetonitrile/water (90/10, v/v) and mobile phase B as 100% ethanol and a gradient run. Under this chromatographic condition four MRM with m/z=1304>1304, 1306>1306, 1704>1704, and 1706>1706 transitions were monitored simultaneously. These MRM transitions were chosen because, first, OLL and OOL are the two major triglycerides (TGs) present in sesame oil. OLL makes up about 13-30% of the triglycerides in sesame oil and OOL makes up about the other 14-25%. Second, the linoleoyl fatty acid side chain has two homoconjugated double bonds, where the C—H located in between the two double bonds is susceptible to adduct formation. Based on the molecular weights of OLL and OOL, these two molecules will have monoisotopic masses at approximately 1304 and 1306, respectively, if they form an adduct with one testosterone enanthate (TE), and a sodium atom which is abundant in the solution. If two TE molecules are attached to OLL and OOL, then the monoisotopic masses will be 1704 and 1706, respectively (Table 2). And third, screening using MRM mode provides an enhanced sensitivity.

TABLE 2

Monoisotopic Masses of Possible OLL and OOL Adducts

| Name Formula | Average MW | Mono isotopic mass | Mono isotopic mass + Na | Monoisotopic mass Na$^+$ + 1 TE (400.3) | Monoisotopic mass Na$^+$ + 2 TE (800.6) |
|---|---|---|---|---|---|
| OLL 1,2-dilinoleoyl-3-oleoyl-rac-glycerol $C_{57}H_{100}O_6$ | 881.40 | 880.8 | 903.8 | 1304.1 | 1704.4 |

TABLE 2-continued

Monoisotopic Masses of Possible OLL and OOL Adducts

| Name Formula | Average MW | Mono isotopic mass | Mono isotopic mass + Na | Monoisotopic mass Na$^+$ + 1 TE (400.3) | Monoisotopic mass Na$^+$ + 2 TE (800.6) |
|---|---|---|---|---|---|
| OOL 1,2-dioleoyl-3-linoleoyl-rac-glycerol $C_{57}H_{102}O_6$ | 883.42 | 882.8 | 905.8 | 1306.1 | 1706.4 |

Figure 13:
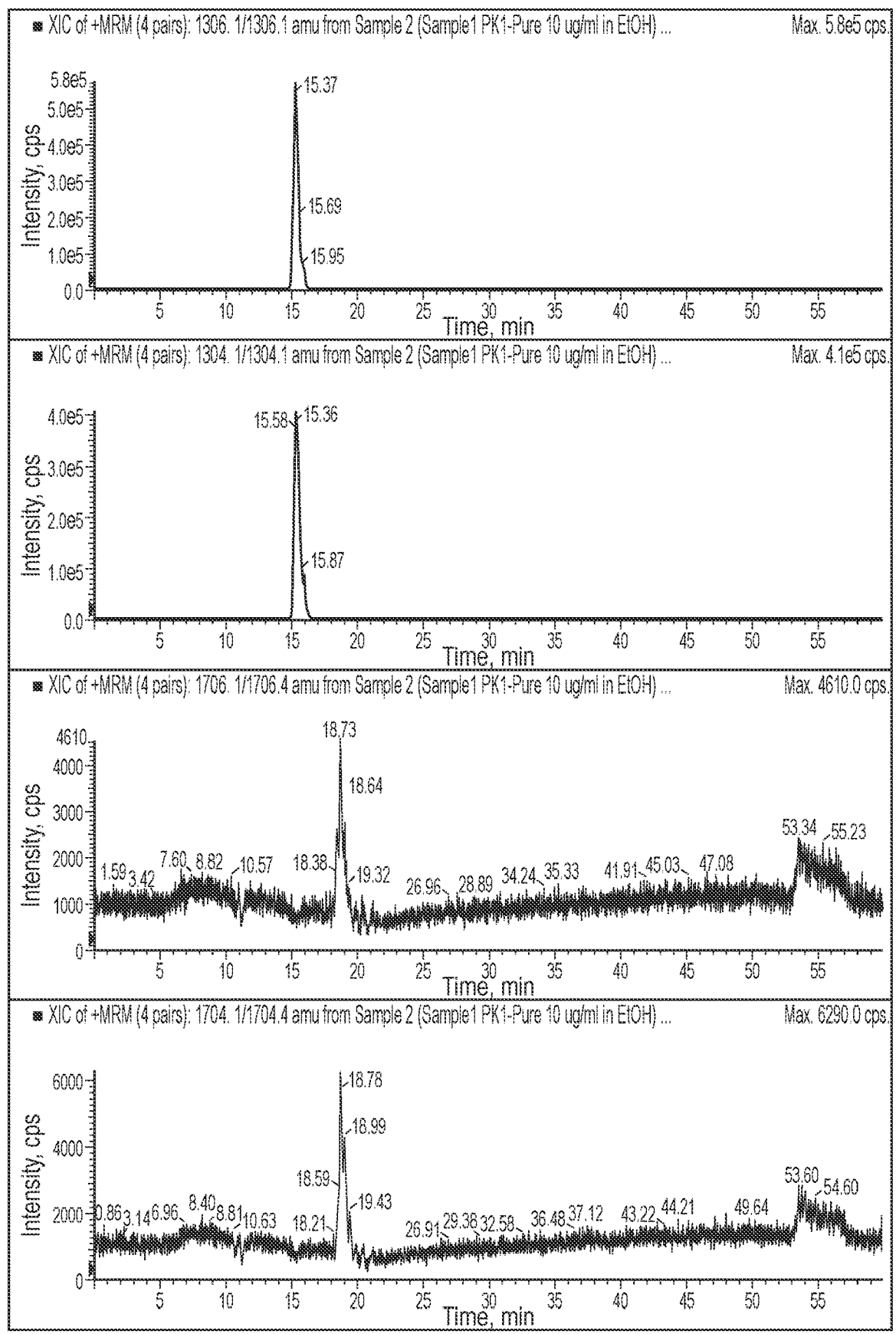
FIG. 13 illustrates the MS spectrum of purified fraction 1 in MRM transitions 1304>1304, 1306>1306, 1706>1706, and 1704>1704.

Molecules with monoisotopic masses equaled to 1304, 1306 for adducts with one TE and 1704, 1706 for adducts with two TEs were searched. The results showed that in each of transition windows 1304>1304 and 1306>1306 a significant peak was observed. In addition, there were a less intense peak detected in transition windows 1704>1704 and 1706>1706 (FIG. 13).

Figure 14:
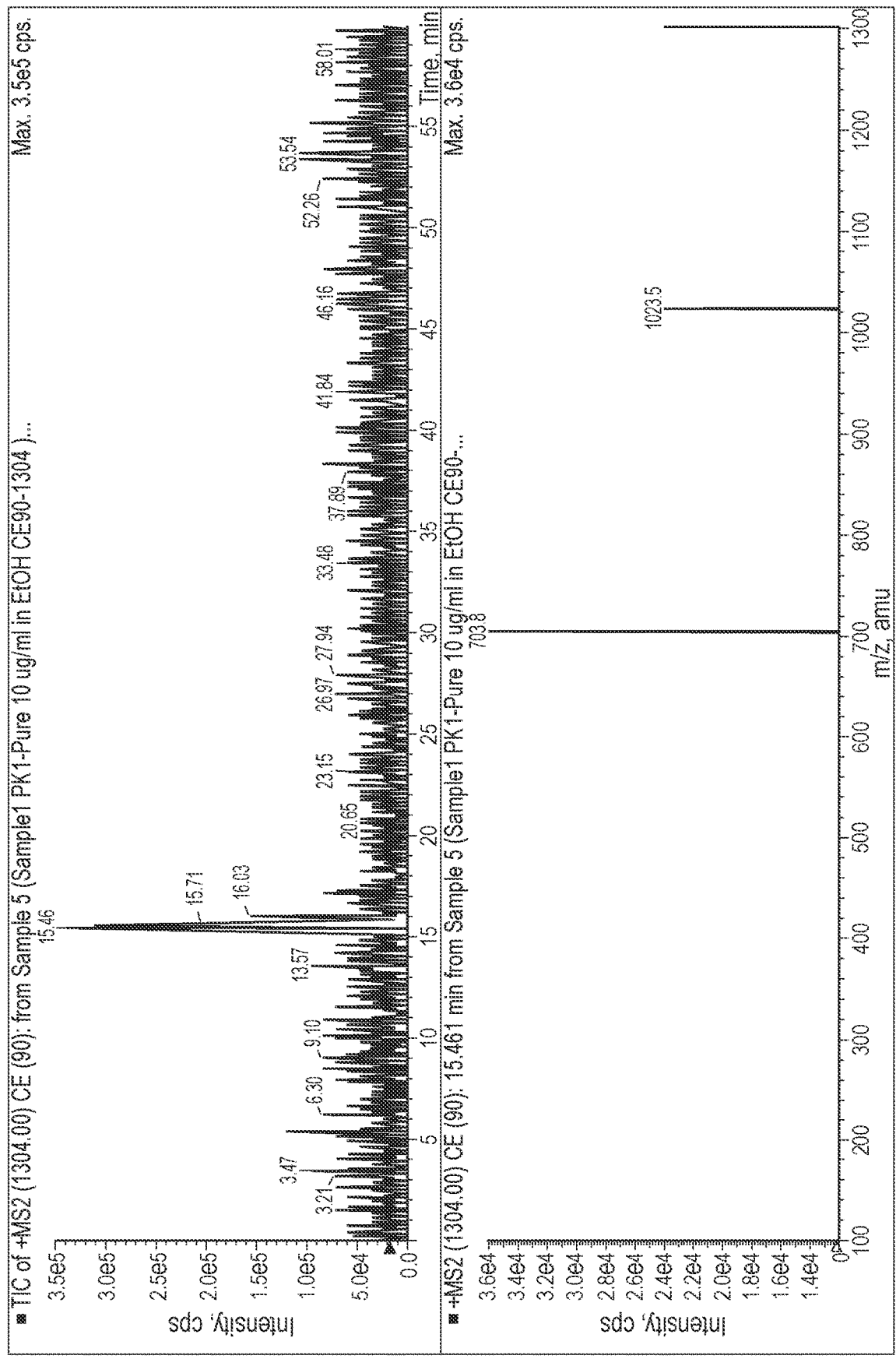
FIG. 14 illustrates the MS2 spectrum of m/z=1304 using collision energy=90 eV.
Figure 15:
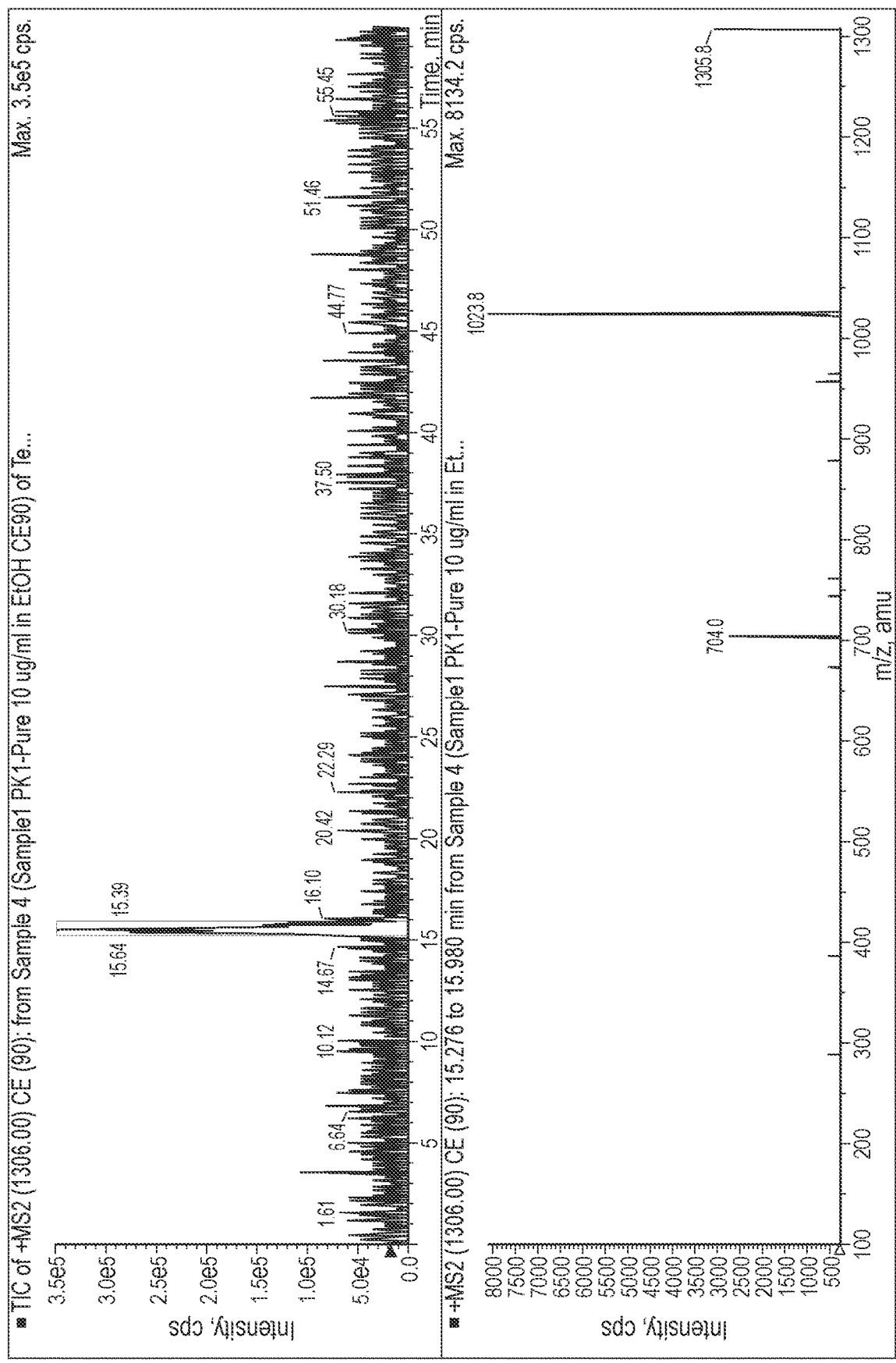
FIG. 15 illustrates the MS2 spectrum of m/z=1306 using collision energy=90 eV.
Figure 16:
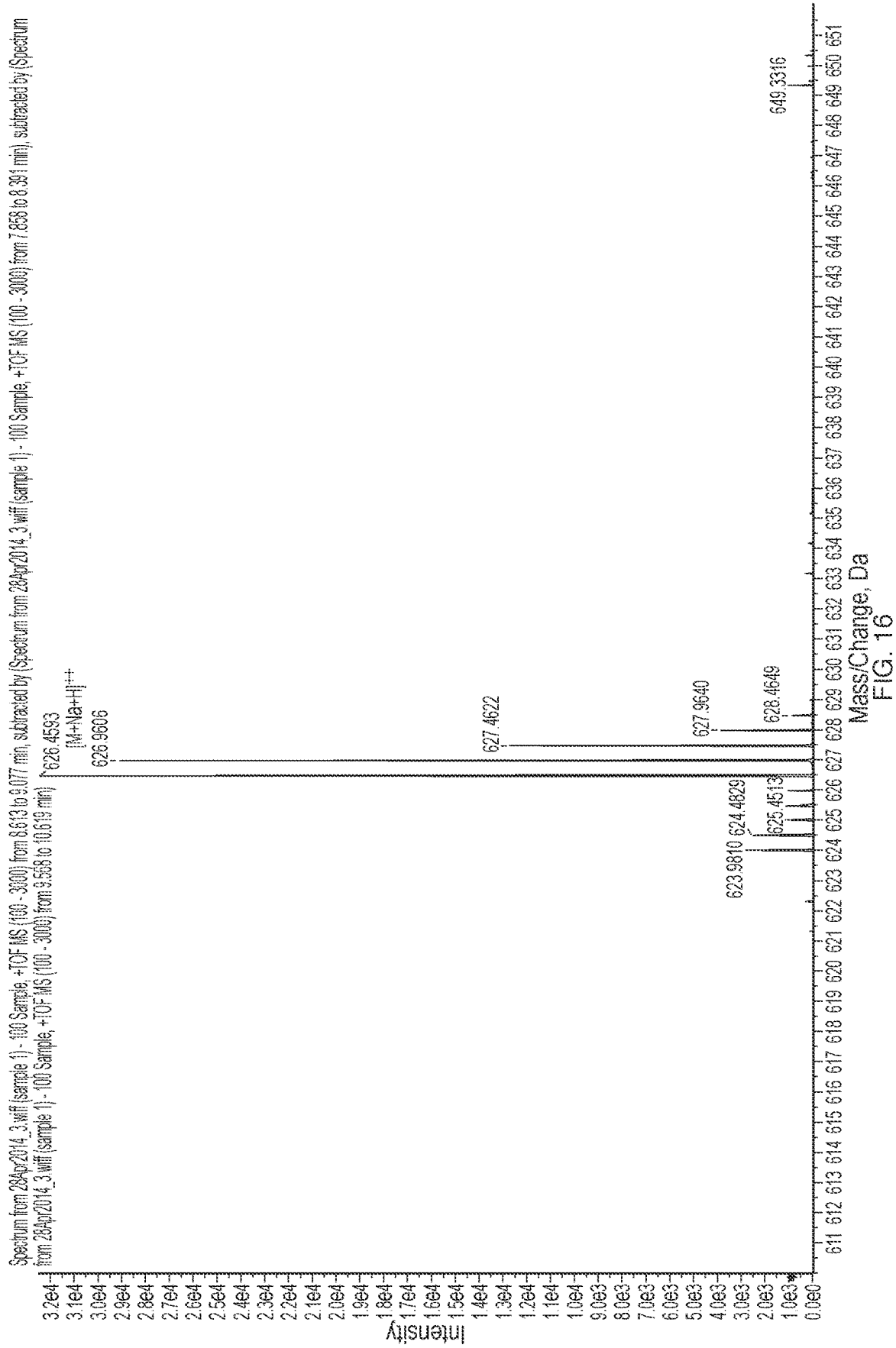
FIG. 16 illustrates a mass spectrum, the major response at ~9.8 minutes in CAD, region 1, light stress sample; proposed empirical formula: $C_{80}H_{124}O_9$ (mass error −1.9 ppm).
Figure 17:
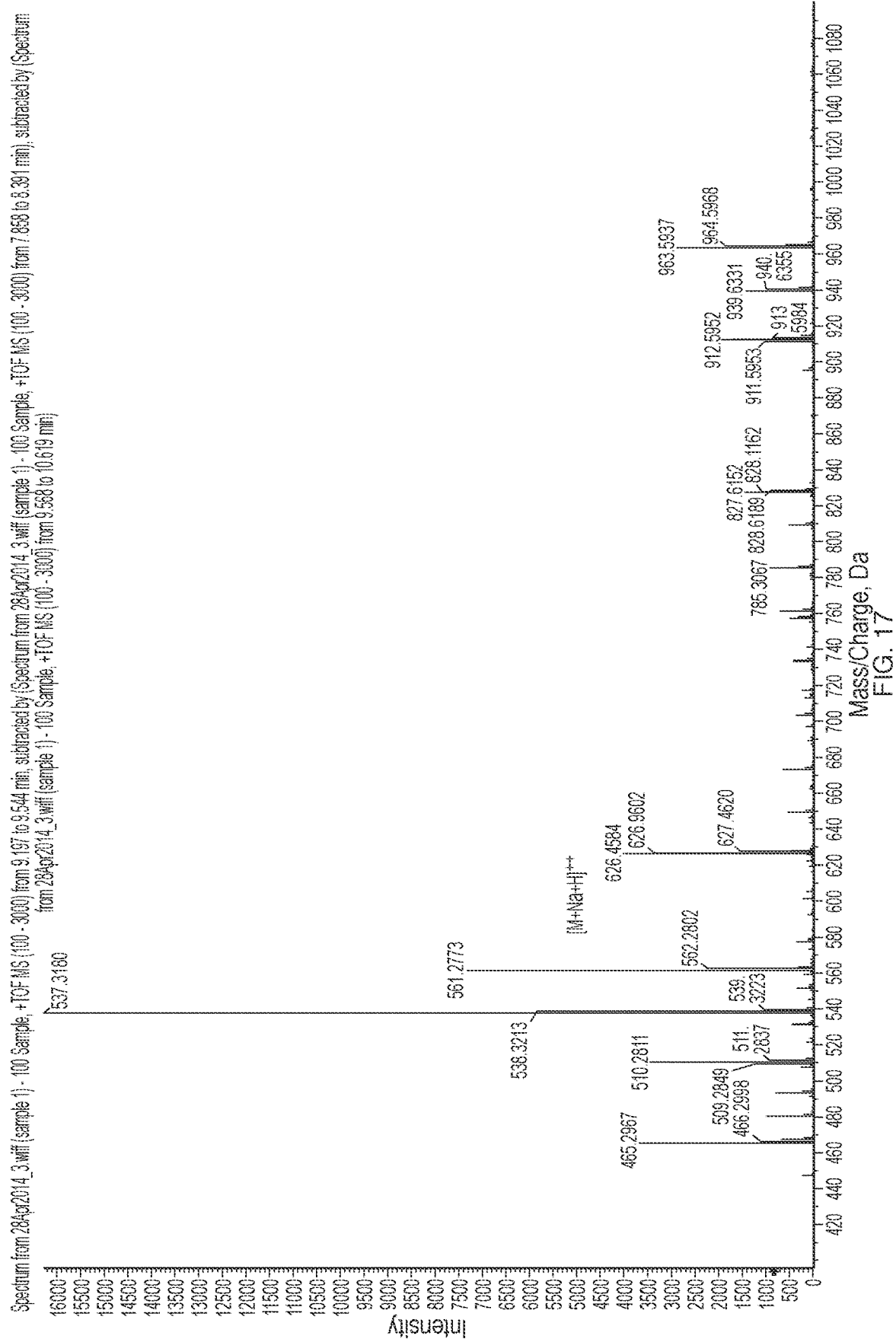
FIG. 17 illustrates a mass spectrum, the minor response at ~10.4 minutes in CAD, region 1 light stress sample.
Figure 18:
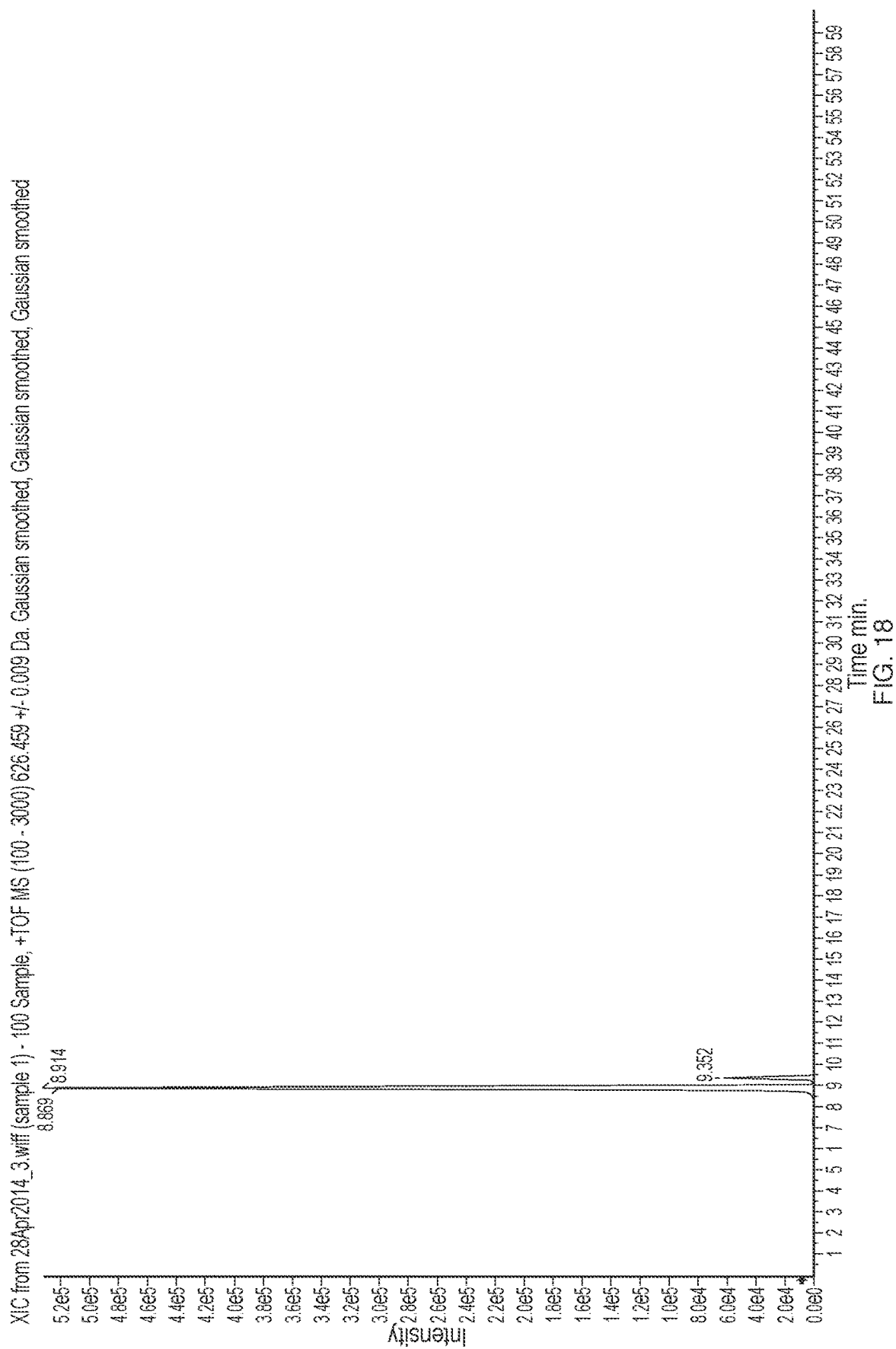
FIG. 18 illustrates an extracted ion chromatogram (XIC), light stress sample, n/z 626.
Figure 19:
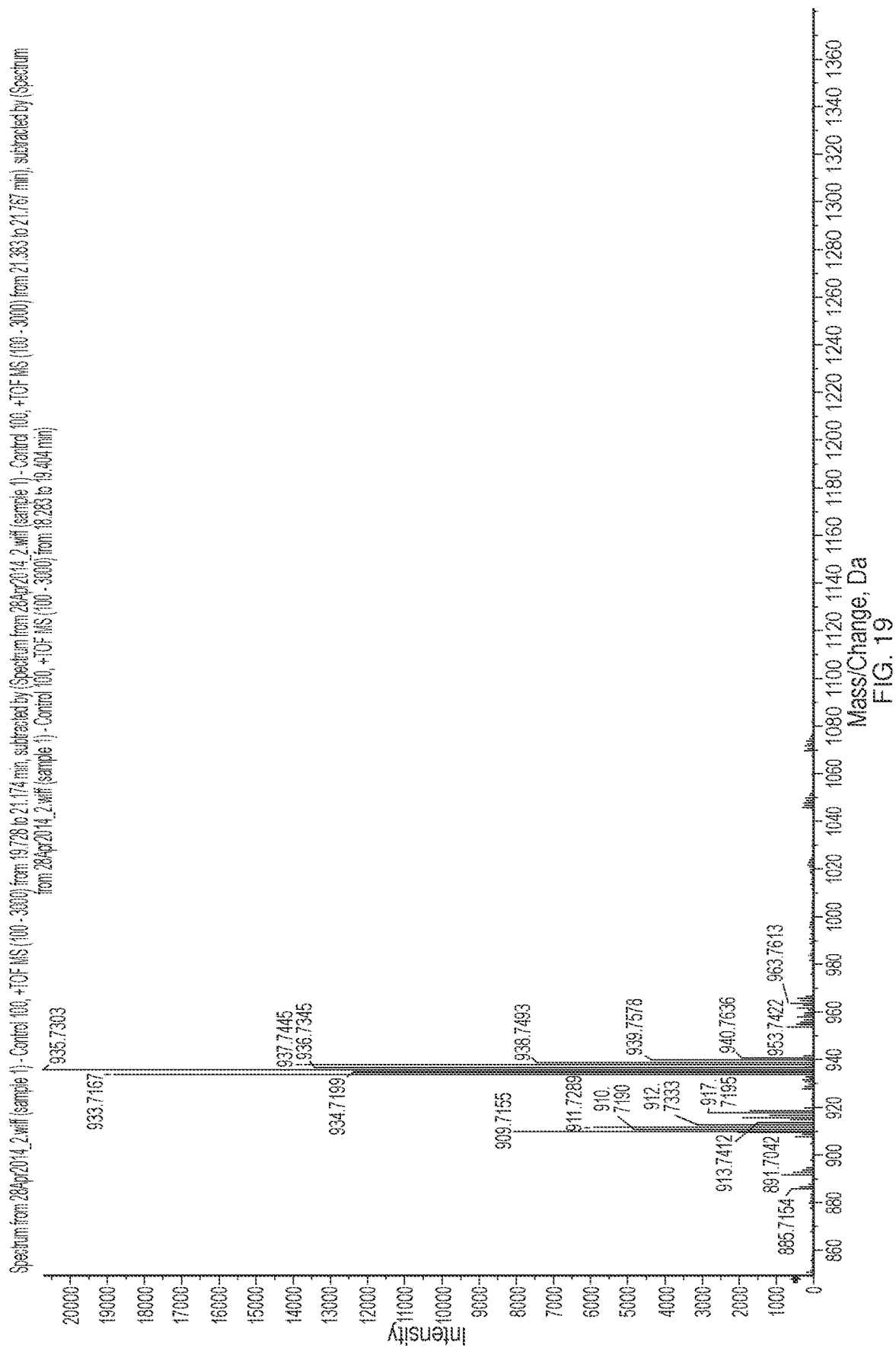
FIG. 19 illustrates the mass spectrum of control sample, region 2.
Figure 20:
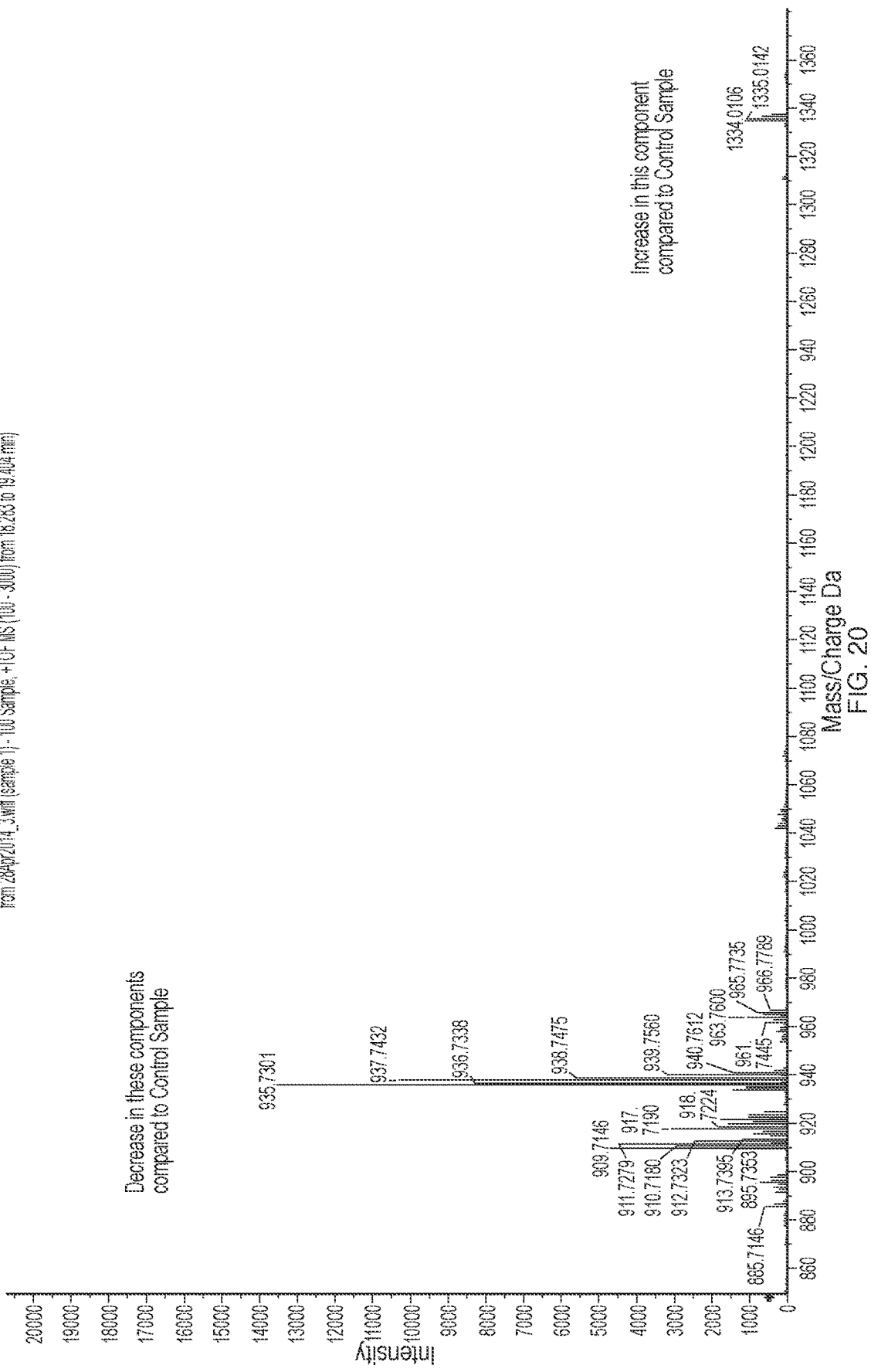
FIG. 20 illustrates the mass spectrum of light stress sample, region 2.
Figure 21:
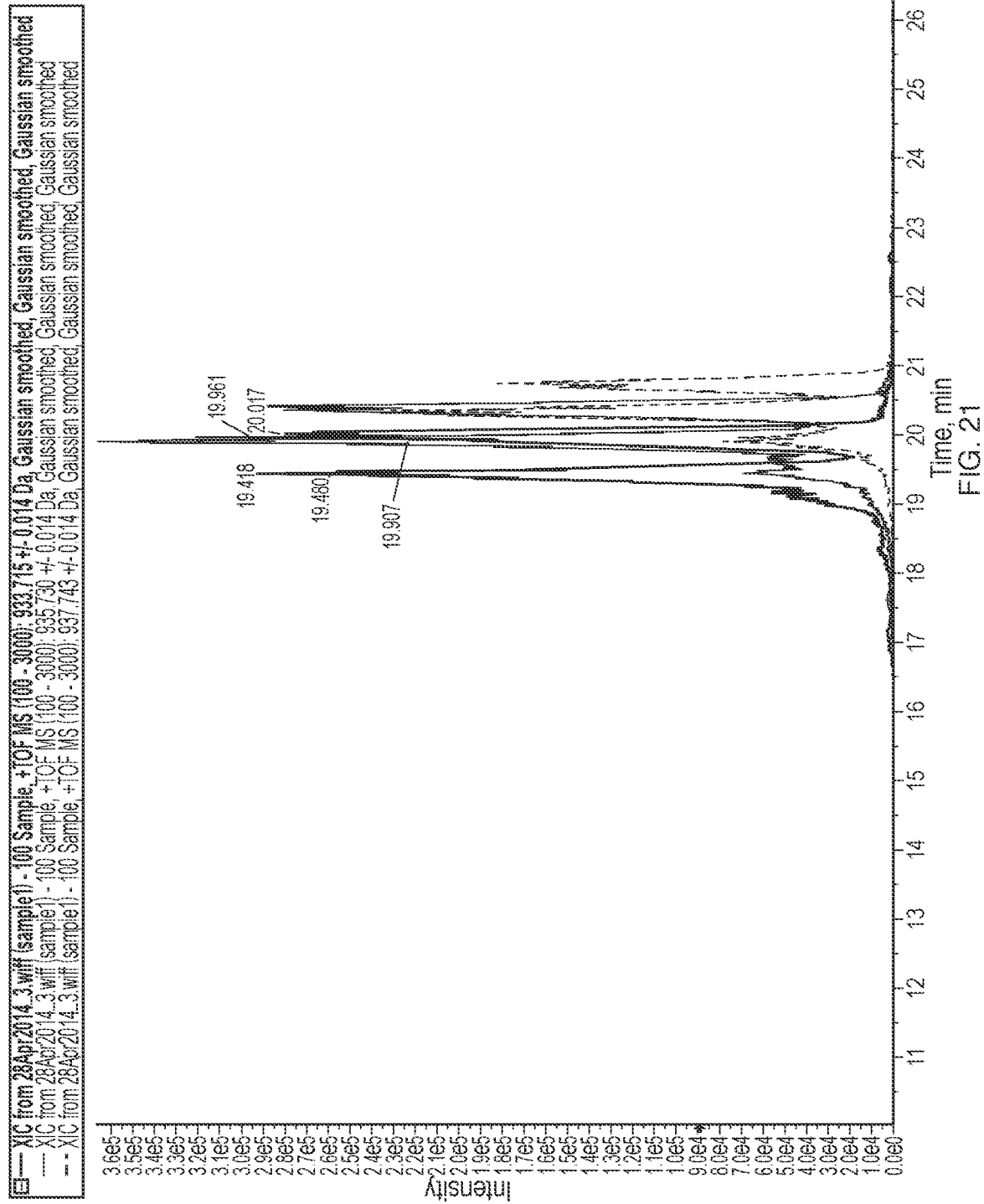
FIG. 21 illustrates XICs of light stress sample, m/z 933 (blue), 935 (pink), and 937 (orange).
Figure 22:
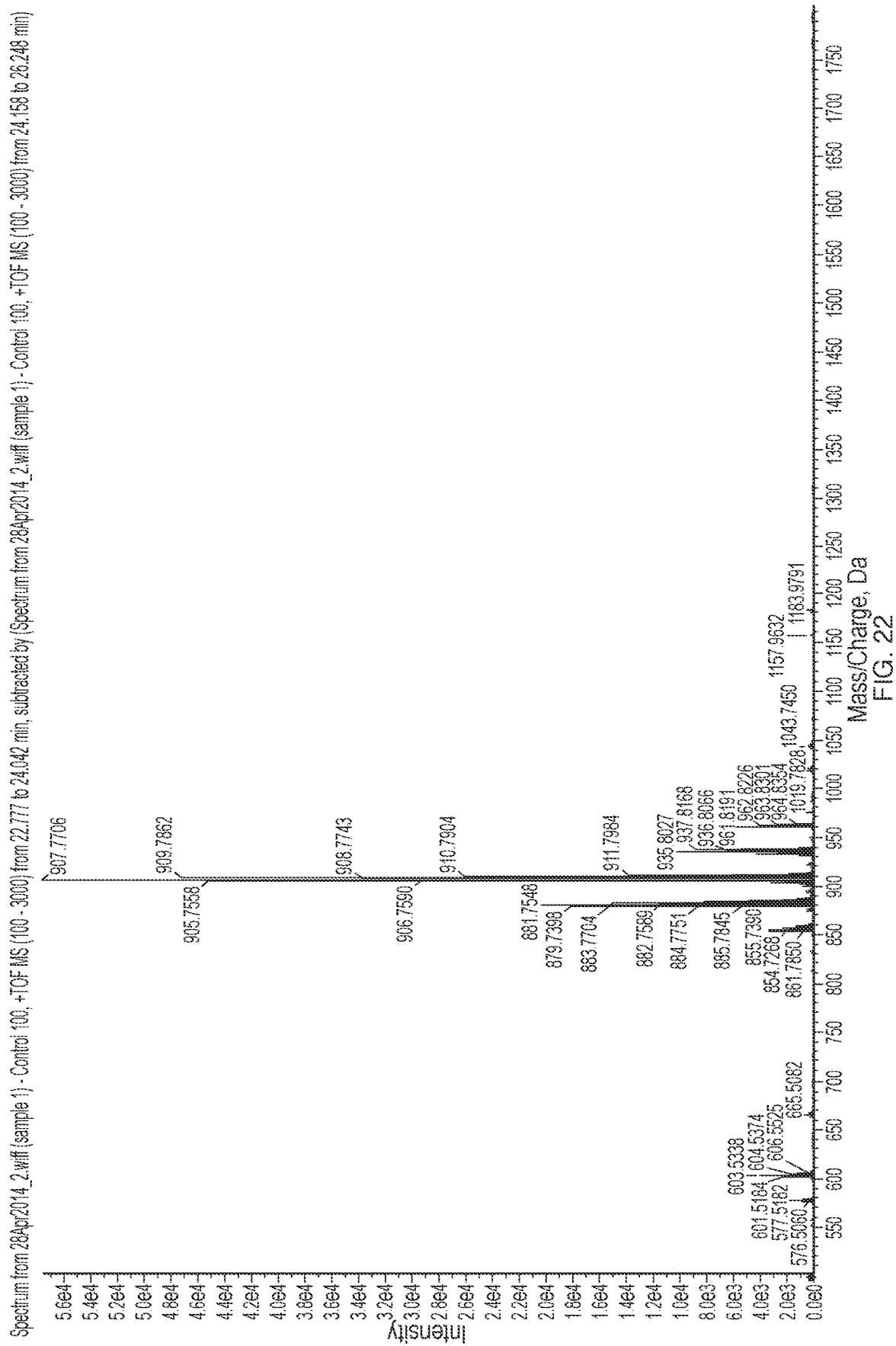
FIG. 22 illustrates the mass spectrum of control sample, region 3.
Figure 23:
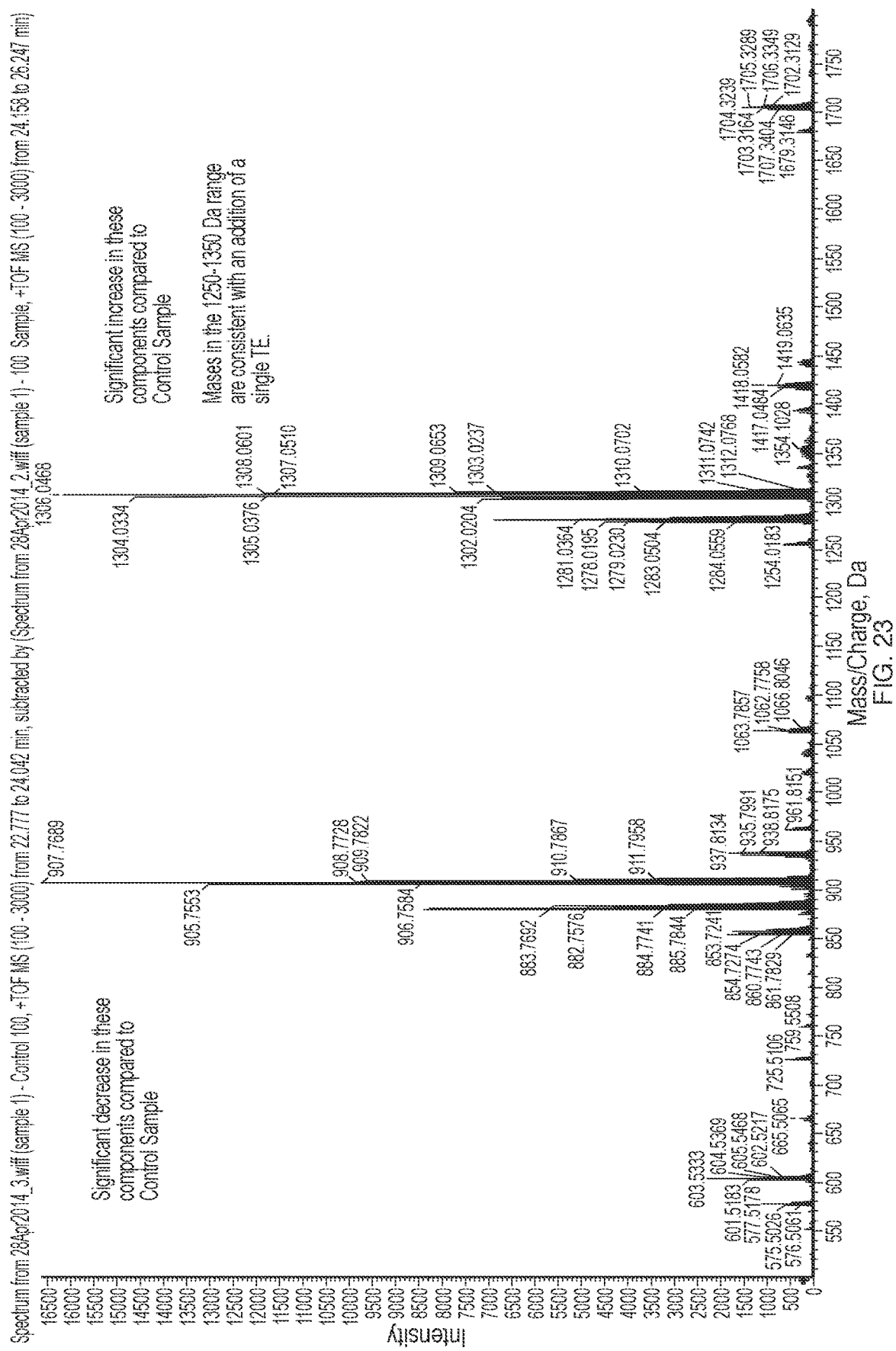
FIG. 23 illustrates the mass spectrum, 100 sample, region 3.
Figure 24:
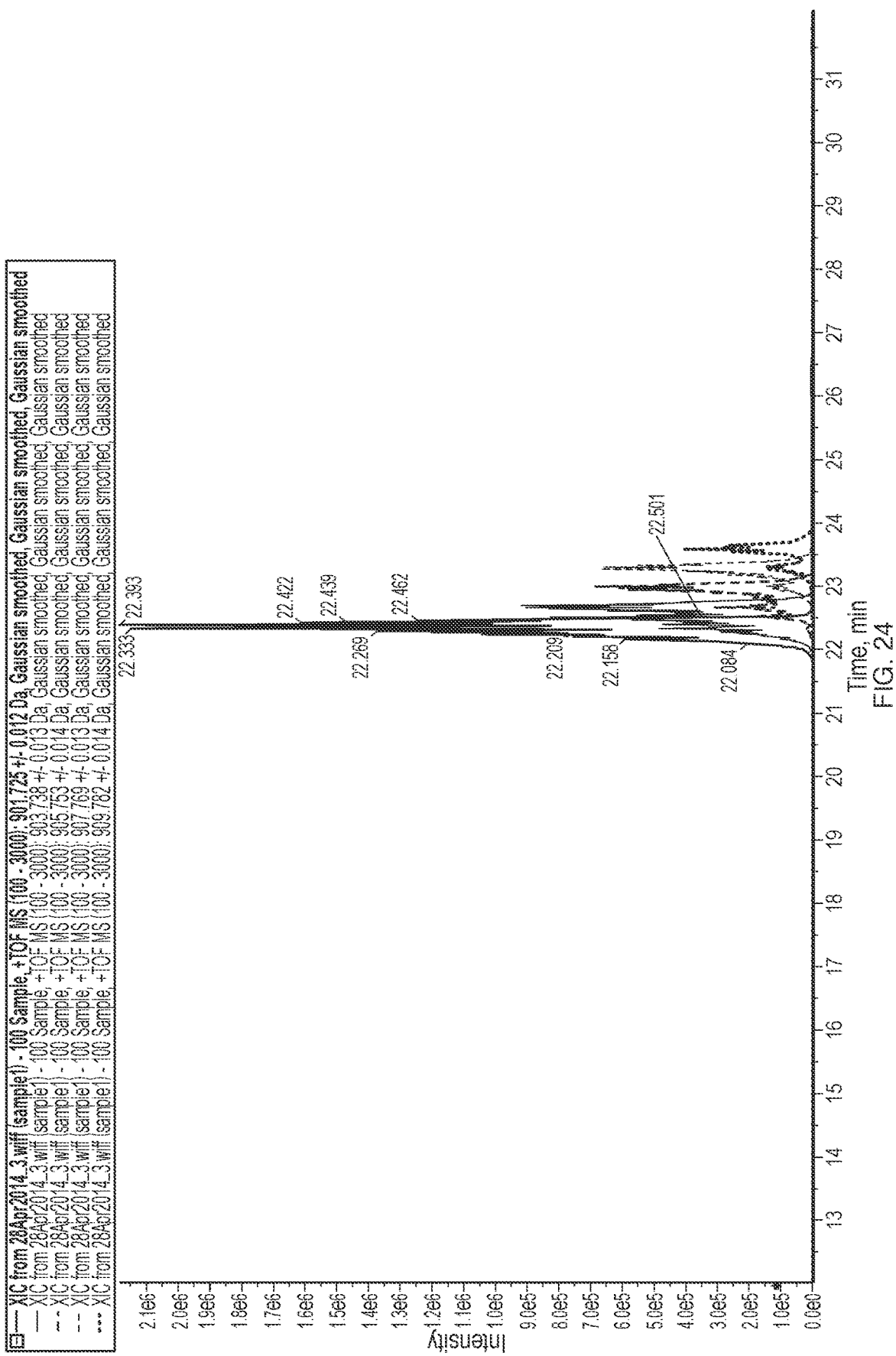
FIG. 24 illustrates XICs of light stress sample, m/z 901 (blue), 903 (pink), 905 (orange), 907 (green), and 909 (light blue).
Figure 25:
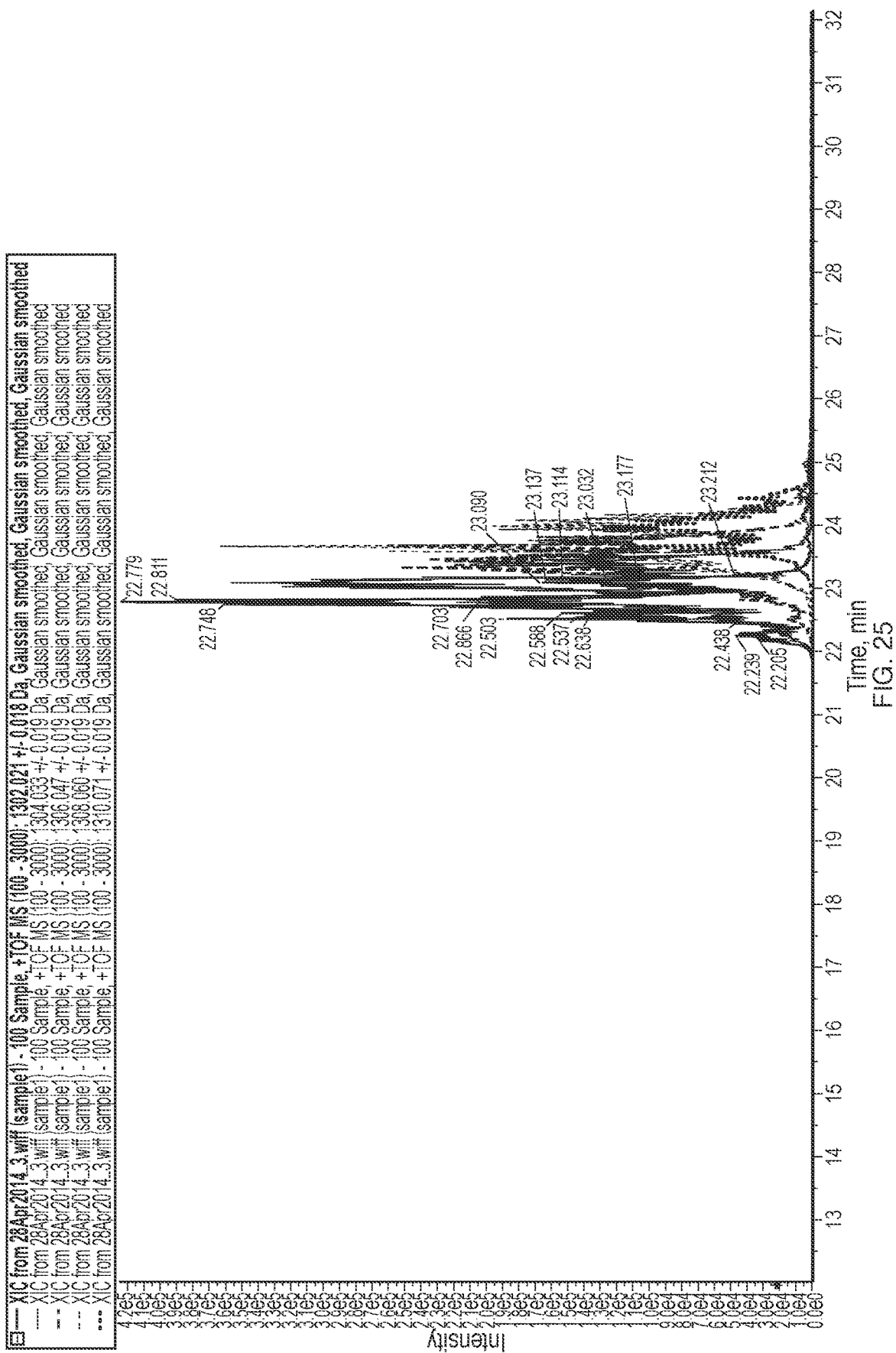
FIG. 25 illustrates XICs of light stress sample, m/z 1302 (blue), 1304 (pink), 1306 (orange), 1308 (green), and 1310 (light blue).
Figure 26:
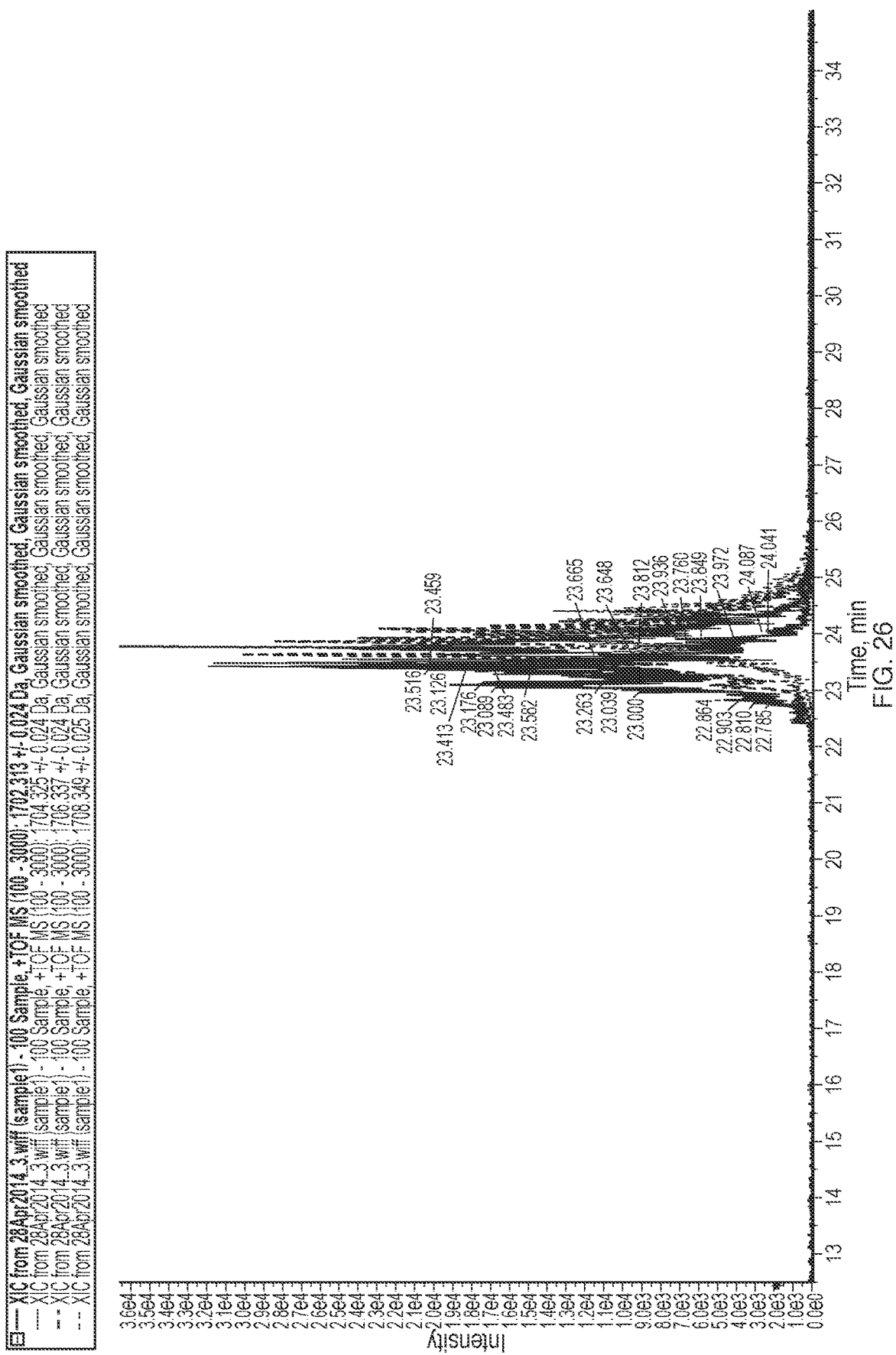
FIG. 26 illustrates XICs of light stress sample, m/z 1702 (blue), 1704 (pink), 1706 (orange), and 1708 (green).
Figure 27:
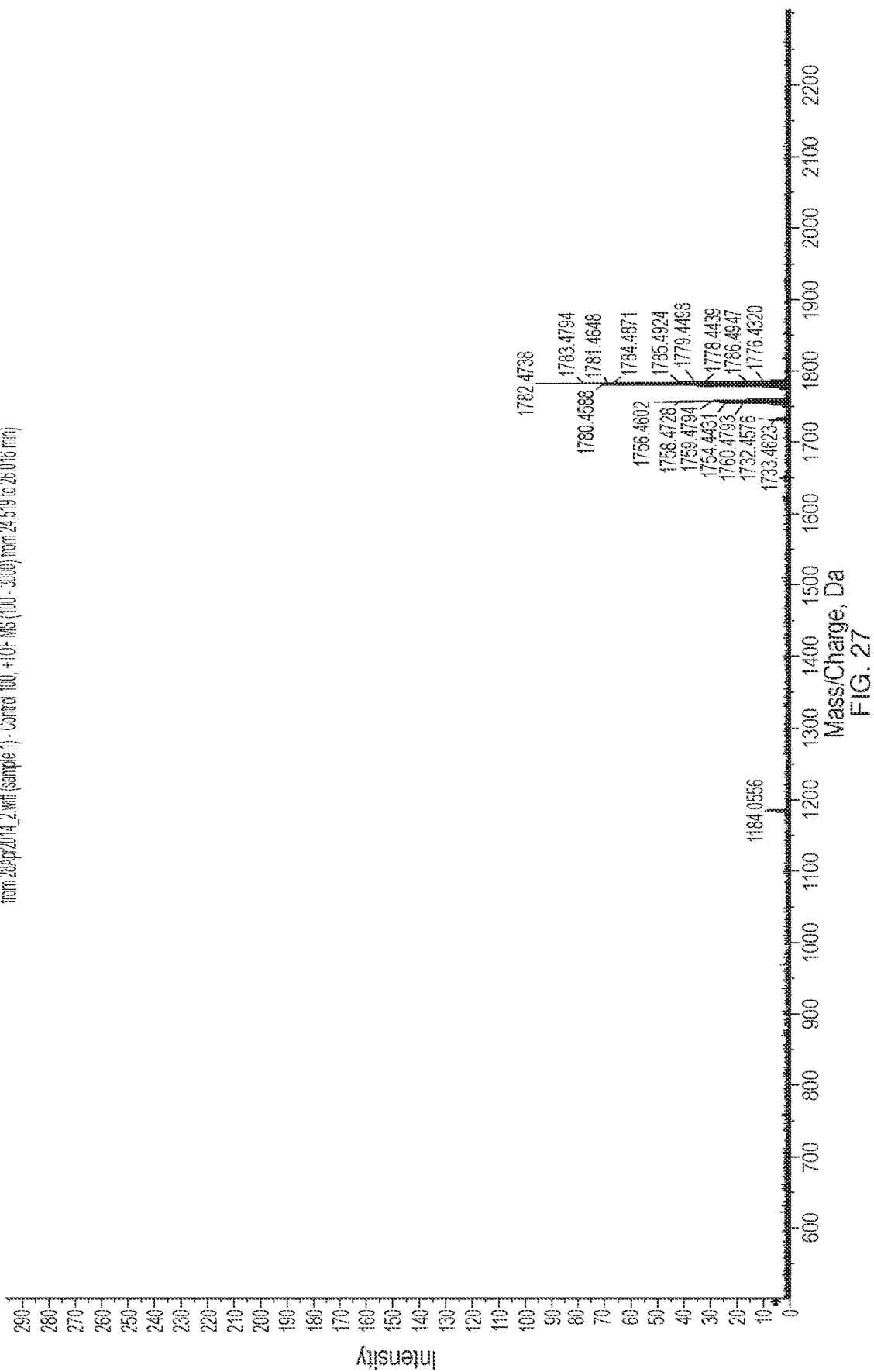
FIG. 27 illustrates the mass spectrum of control sample, region 4.
Figure 28:
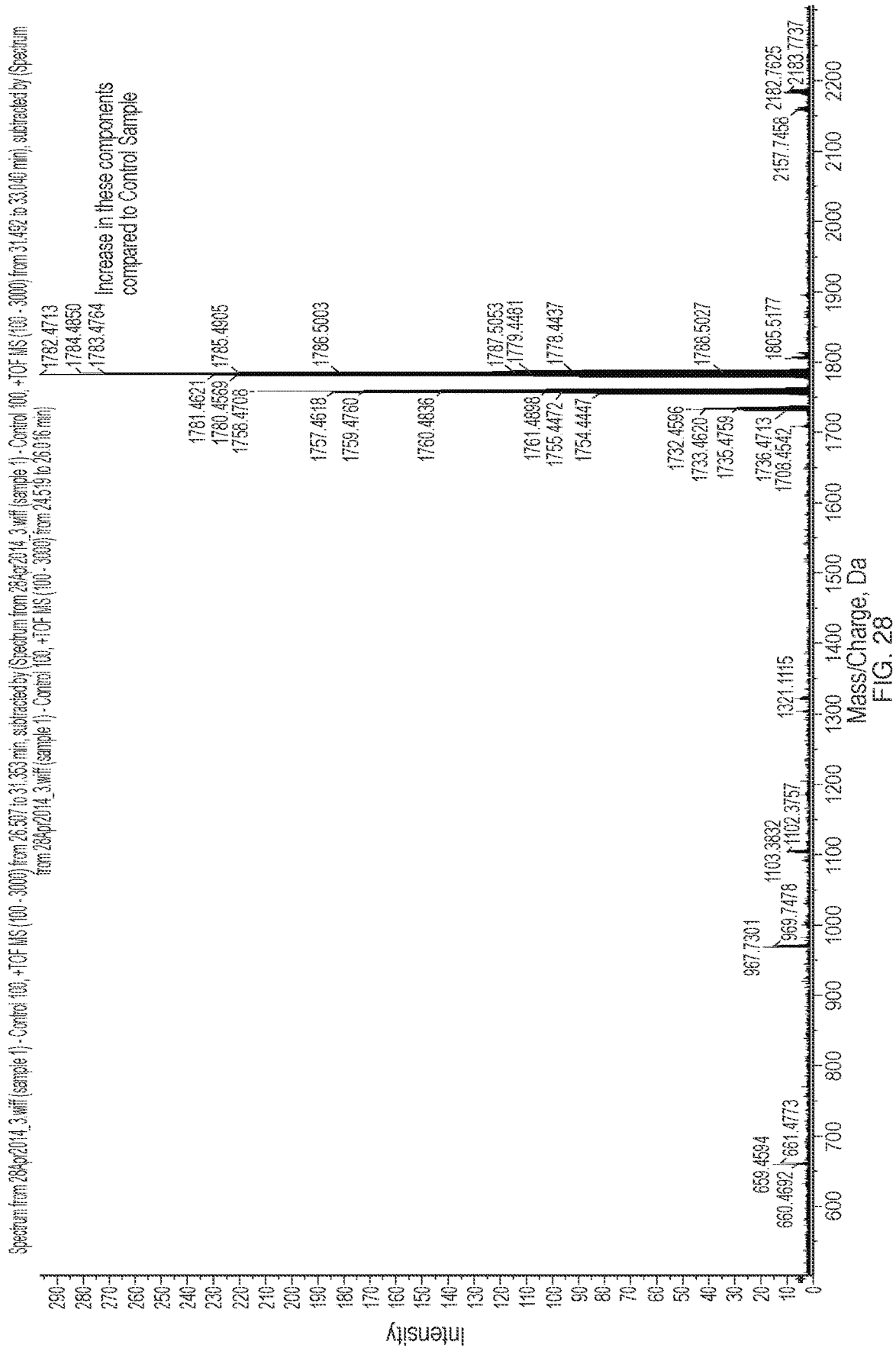
FIG. 28 illustrates the mass spectrum of light stress sample, region 4.
Figure 29:
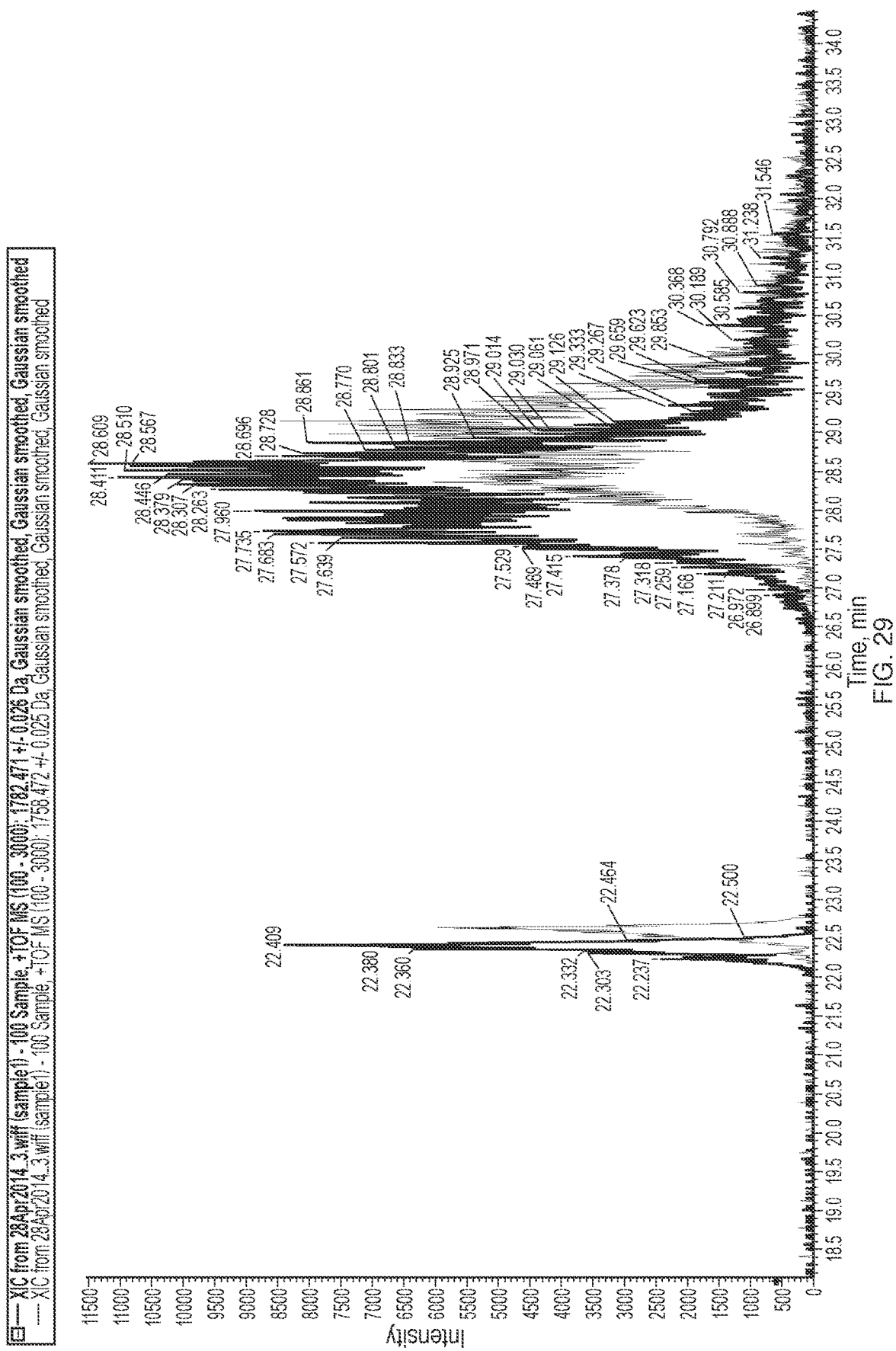
FIG. 29 illustrates XICs of light stress sample, m/z 1782 (blue) and 1758 (pink).

When the 10 µg/mL sample was subjected to MS2 under positive ionization with a collision energy of 90 eV, the 1304 and 1306 ions were fragmented to form similar product ions. The molecule with m/z=1304 produced 703.8 and 1023.5 (FIG. 14) and the molecule with m/z=1306 produced 704 and 1023.8 (FIG. 15). Additional MS data is presented in FIGS. 16 to 29. FIG. 16 illustrates a mass spectrum, the major response at ~9.8 minutes in CAD, region 1, light stress sample; proposed empirical formula: $C_{80}H_{124}O_9$ (mass error −1.9 ppm). FIG. 17 illustrates a mass spectrum, the minor response at ~10.4 minutes in CAD, region 1 light stress sample. FIG. 18 illustrates an extracted ion chromatogram (XIC), light stress sample, m/z 626. FIG. 19 illustrates the mass spectrum of control sample, region 2. FIG. 20 illustrates the mass spectrum of light stress sample, region 2. FIG. 21 illustrates XICs of light stress sample, m/z 933 (blue), 935 (pink), and 937 (orange). FIG. 22 illustrates the mass spectrum of control sample, region 3. FIG. 23 illustrates the mass spectrum, 100 sample, region 3. FIG. 24 illustrates XICs of light stress sample, m/z 901 (blue), 903 (pink), 905 (orange), 907 (green), and 909 (light blue). FIG. 25 illustrates XICs of light stress sample, m/z 1302 (blue), 1304 (pink), 1306 (orange), 1308 (green), and 1310 (light blue). FIG. 26 illustrates XICs of light stress sample, m/z 1702 (blue), 1704 (pink), 1706 (orange), and 1708 (green). FIG. 27 illustrates the mass spectrum of control sample, region 4. FIG. 28 illustrates the mass spectrum of light stress sample, region 4. FIG. 29 illustrates XICs of light stress sample, m/z 1782 (blue) and 1758 (pink).

The $^1$H NMR and $^{13}$C NMR study of this adduct coupled with HRMS study suggest that the adduct in fraction 1 was a mixture of two major components: the adduct of testosterone enanthate with OLL (adduct A) and testosterone enanthate with OOL (adduct B; Scheme 1). These proposed structures are consistent with a testosterone enanthate sodium adduct formed with OLL and OOL which has a m/z=1304 and 1306 respectively. The proposed structure of adduct A is consistent with a testosterone enanthate sodium adduct formed with OLL, and a likely fragmentation pathway of adduct A to produce the product ion that has m/z=1023.8 is also described (Scheme 2). The proposed structure of adduct B is consistent with a testosterone enanthate sodium adduct formed with OOL (Scheme 3).

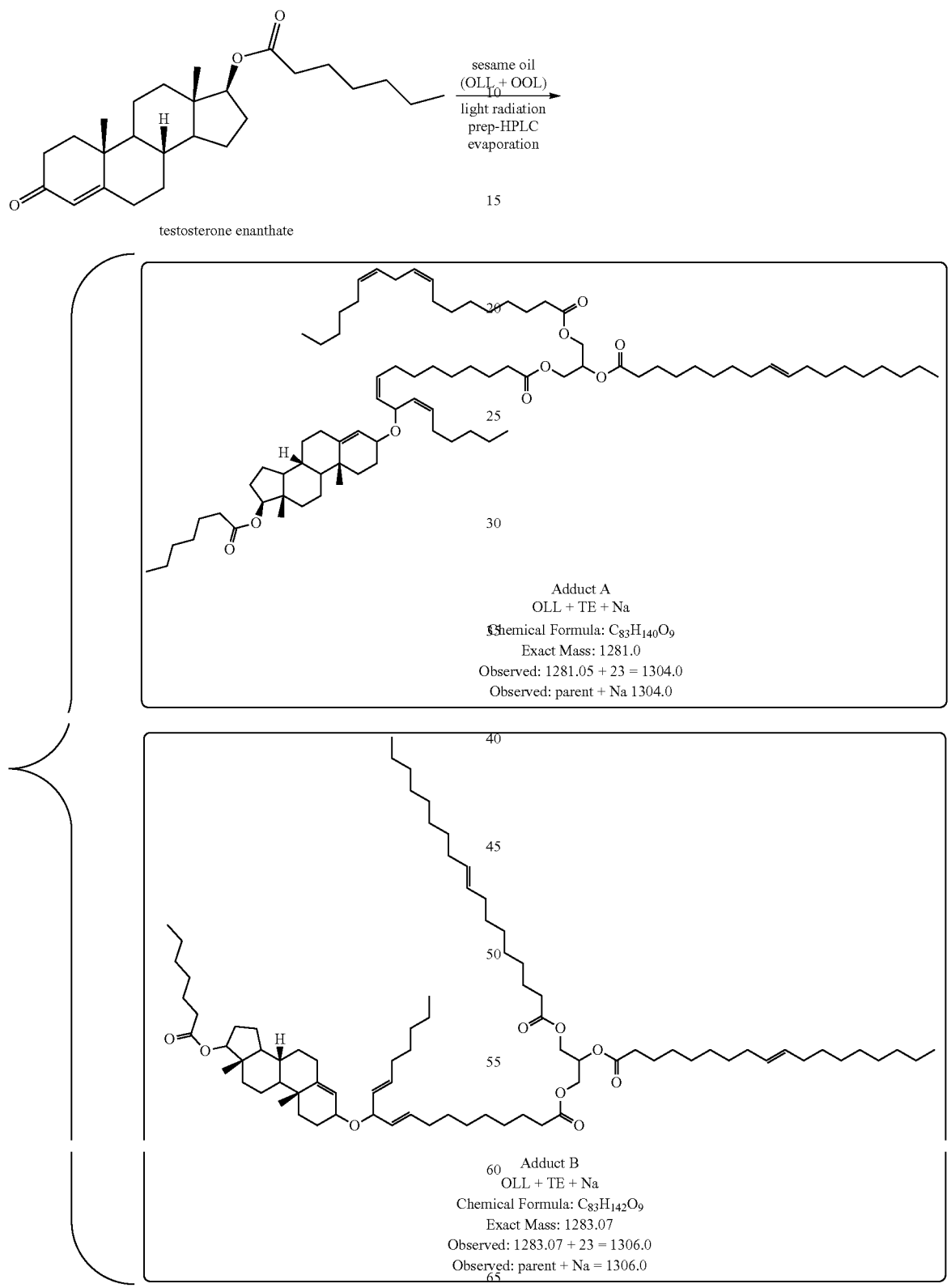
Scheme 1 Reaction scheme and structures of OLL and OOL Testosterone Triglyceride Adducts after stress induced by light radiation
Adduct A
OLL + TE + Na
Chemical Formula: $C_{83}H_{140}O_9$
Exact Mass: 1281.0
Observed: 1281.05 + 23 = 1304.0
Observed: parent + Na 1304.0
Adduct B
OLL + TE + Na
Chemical Formula: $C_{83}H_{142}O_9$
Exact Mass: 1283.07
Observed: 1283.07 + 23 = 1306.0
Observed: parent + Na = 1306.0

Scheme 2 Fragmentation Pathway of adduct A to Form a Product Ion with m/z = 1023.8
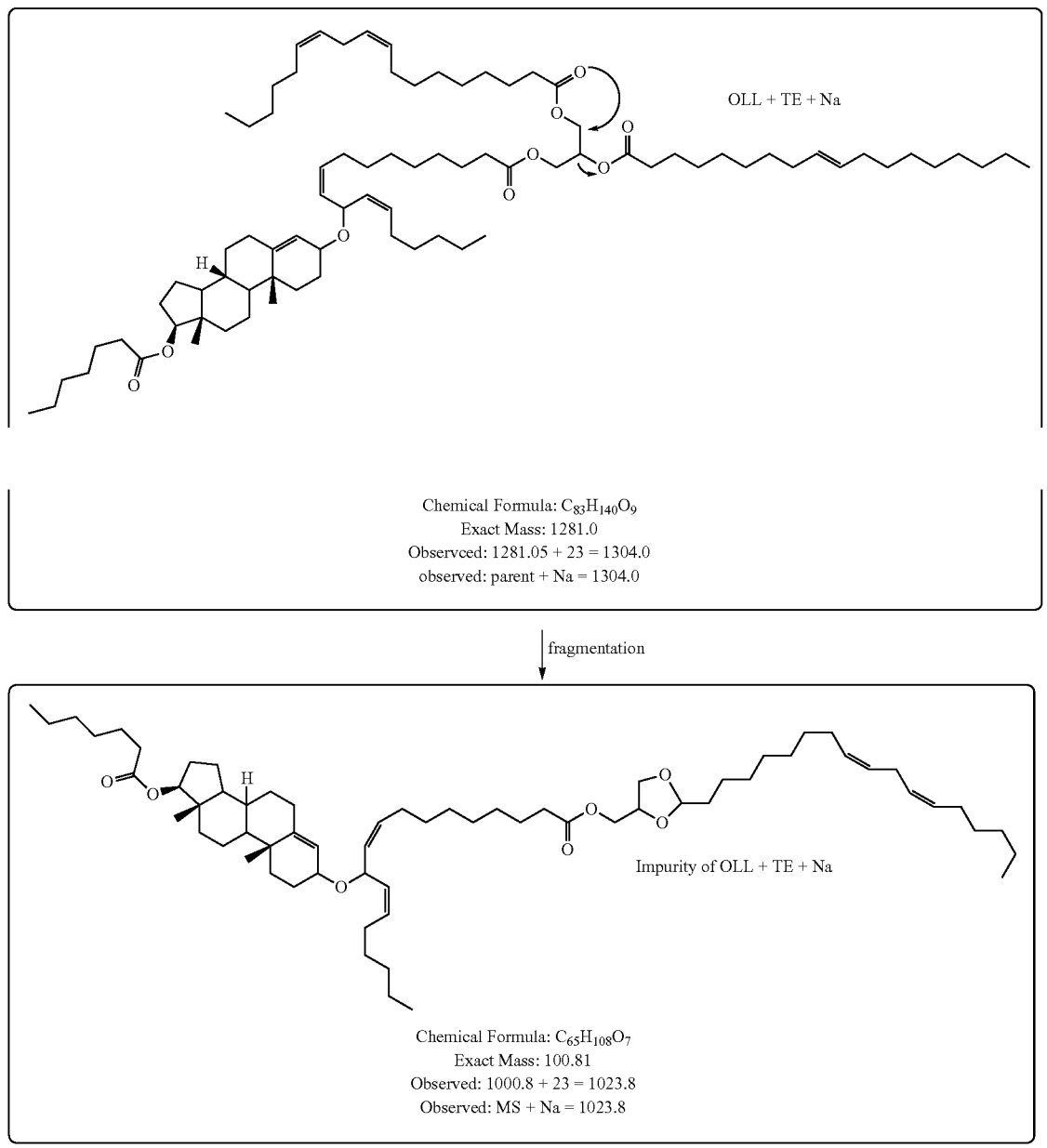
Scheme 3 Fragmentation Pathway of Adduct B to Form a Product Ion with m/z = 1023.8
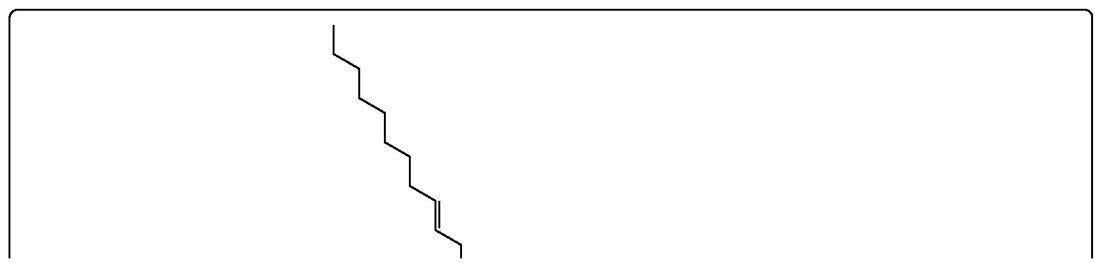

-continued
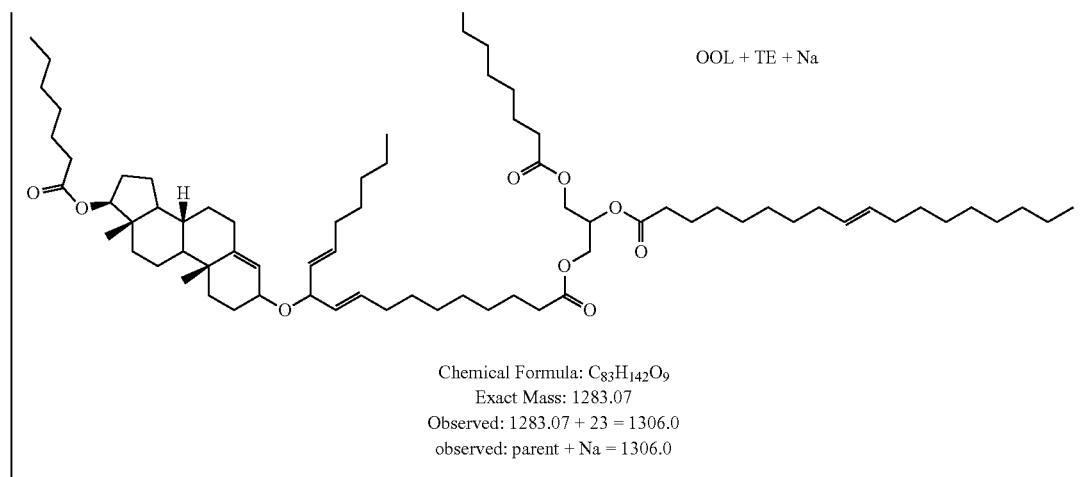
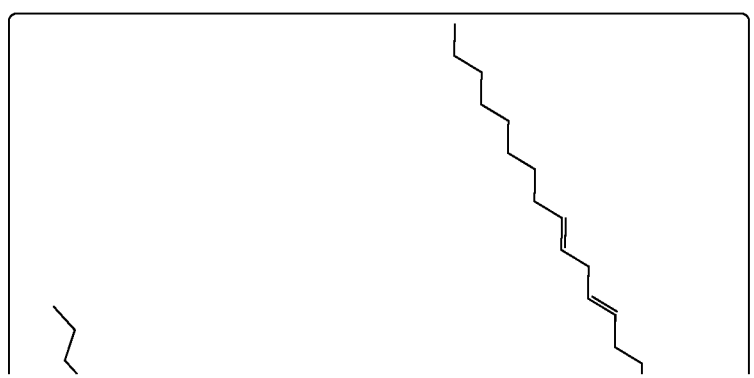
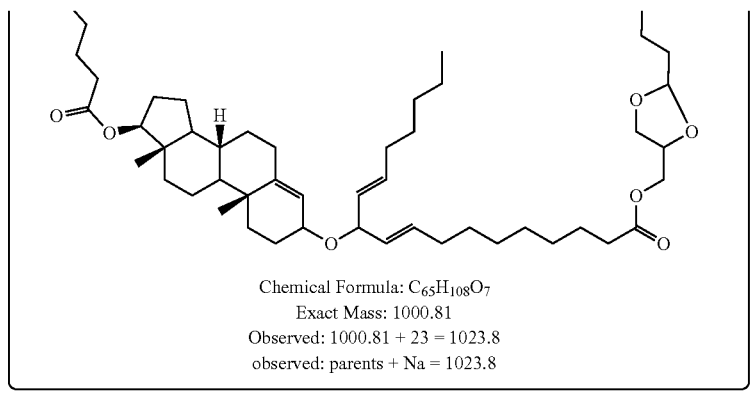
Most signals of adducts A and B are overlapped in both the $^1$H NMR and $^{13}$CNMR spectra (FIG. 7 to FIG. 12). For simplicity, only adduct A (OLL+TE) is assigned and shown here as an example (Scheme 4).

Scheme 4: Proton and Carbon Assignment based on the $^1$H NMR and $^{13}$C NMR Results

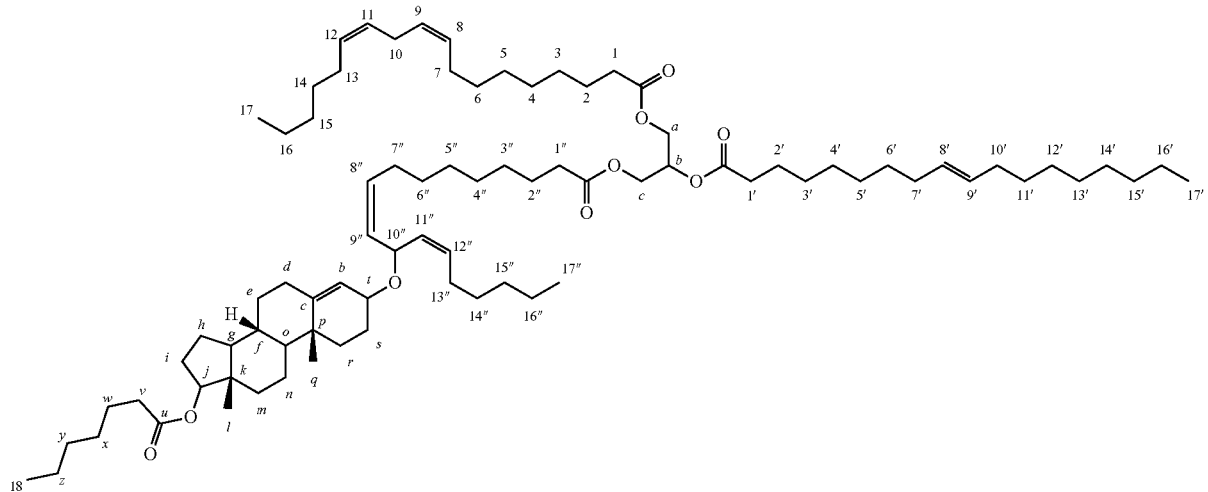

$^1$H NMR: δ 0.85 (m, 3H, H17'), 0.9 (m, 15H, H17, H17", H18, Hi, Hq), 1.3 (m, 67H, H3, H4, H5, H6, H14, H15, H16, H3', H4', H5', H6', H11', H12', H13', H14', H15', H16', H3", H4", H5", H6", H14", H15", H16", Hx, Hy, Hz, He, Hf, Hg, Hh, Hm, Hn, Ho, Hr), 1.61 (m, 8H, H2, H2', H2", Hw), 2.0 (m, 16H, H7, H7', H7", H10, H10', H13, H13", Hd,), 2.32 (m, 10H, H1, H1', H1", Hv, Hs), 2.77 (m, 2H, H10), 4.15 (m, 3H), 4.30 (m, 3H), 5.32 (m, 2H), 5.36 (m, 10H, H8, H9, H11, H12, H8', H9', H11', H12', H8", H9")

$^{13}$CNMR: δ 14.3 (C17, C17', C17", C18), 22.71 (C16, C16', C16", Cz), 22.79 (C2, C2', C2", Cw), 22.90, 25.06, 25.29, 25.84, 27.41, 27.44, 27.80, 29.02, 29.27, 29.34, 29.39, 29.54, 29.70, 29.74, 29.84, 29.88, 29.92, 30.66, 31.68, 31.74, 32.12, 32.75, 34.24, 34.41, 62.31 (Ca, Cc), 69.09 (Cb), 128.10, 128.28, 128.45, 129.92, 130.23, 130.44, 173.04, 173.46, 174.13.

In conclusion, after a mixture of testosterone enanthate in sesame oil was subjected to a stress treatment by light radiation (as specified in the ICH guideline), a new adduct was formed. This adduct was purified by preparative HPLC followed by evaporation of the excess solvent to yield the purified fraction 1 (net weight: 587 mg). According to both the $^1$H and C$^{13}$ NMR data, the purified fraction 1 includes two major adducts, i.e., OLL+TE+Na (adduct A) and OOL+TE+Na (adduct B; Scheme 1). Based on the proton NMR data, the purity of the two adducts (m/z=1304 and 1306 combined) is approximately 86%. The mass spectra data showed that the two adduct ions had approximately equal intensities under the same ionization condition. Assuming similar ionization energies, then the two adducts were present in the fraction as an approximately 50:50 mixture. Therefore, purified fraction 1 can be useful for estimating OLL+TE+Na or OOL+TE+Na adduct which may present as impurity in a given TE-sesame oil product.

Example 2: Method Development Summary of HPLC-MS Method for Estimation of Photo-Degradation in Xyosted Drug Product The photo-degradants of testosterone enanthate (TE) in Xyosted Drug Product (Drug Product) could not be detected by preliminary development-level HPLC methods. These methods were comprised of multiple combinations of column polarities ranging from normal phase to reverse phase with various carbon chain lengths and mobile phases with different eluotropic strengths ranging from aqueous-based to purely organic organic-based mobile phases. Since the photo-degradants were not detected in chromatography in which small (both polar and non-polar) molecules typically appear, it was thus hypothesized that the photo-degradants were most likely not breakdown products of the TE molecule, but were adducts between the TE molecule and triglycerides (TGs), which are the major components of sesame oil.

One of the major challenges for methods development was identification of an HPLC-compatible solvent to dissolve the photo-degraded drug product samples. Following exposure of Drug Product to the ICH light conditions, an approximate 60-90% decrease was observed in Assay and thus it was concluded that substantial degradation had occurred. This photo-degraded Drug Product sample was not completely dissolved in the sample diluent used in the preliminary HPLC method, i.e., DMF/ACN: 80/20, nor was it fully dissolved in several other commonly used high solubilizing solvents such as DMSO. Alcohols (e.g., ethanol or isopropanol) were the only solvents, among the numerous solvents tested, that could completely dissolve the photo-degraded Drug Product. Thus, ethanol was chosen as the eluting mobile phase. Following method optimization, the final optimized HPLC conditions used for light forced degradation are shown in Table 3.

TABLE 3

New HPLC Method Used in ICH Photolysis

| | |
|---|---|
| Mobile Phase A: | 90:10 Water/ACN |
| Mobile Phase B: | Ethanol |

TABLE 3-continued

| New HPLC Method Used in ICH Photolysis | |
|---|---|
| Flow Rate: | 1.1 mL/minute |
| Column: | Synergi Max-RP 80A, 150 × 4.6 mm, 4 μm |
| Column Temperature: | 30° C. |
| Injection Volume: | 20 μL |
| Detection Wavelength | 242 nm |
| CAD Settings: | Gas Pressure - 35 psig |
| | Range - 100 pA or setting suitable to provide sufficient sensitivity |
| | Nebulizer Temperature - 30° C. |
| Run Time: | 60 minutes |

| Gradient Program: | Time (Minutes) | % Mobile Phase A | % Mobile Phase B |
|---|---|---|---|
| | 0 | 30 | 70 |
| | 2 | 30 | 70 |
| | 20 | 0 | 100 |
| | 50 | 0 | 100 |
| | 55 | 30 | 70 |
| | 60 | 30 | 70 |

Figure 30:
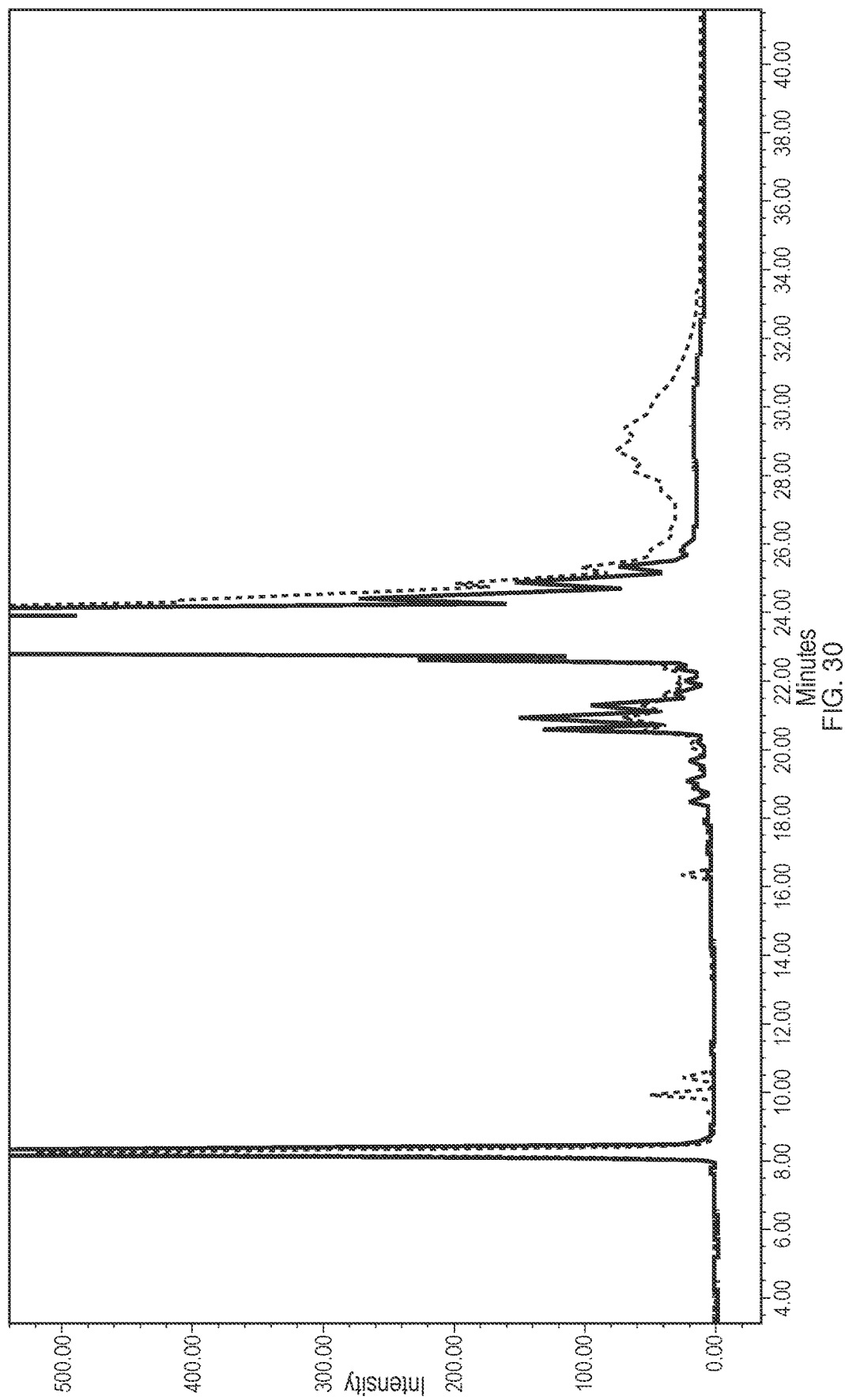
FIG. 30 illustrates exemplary chromatograms of control sample and ICH photolysis sample (charged aerosol detection—CAD; pink=stress; black=control).
Figure 31:
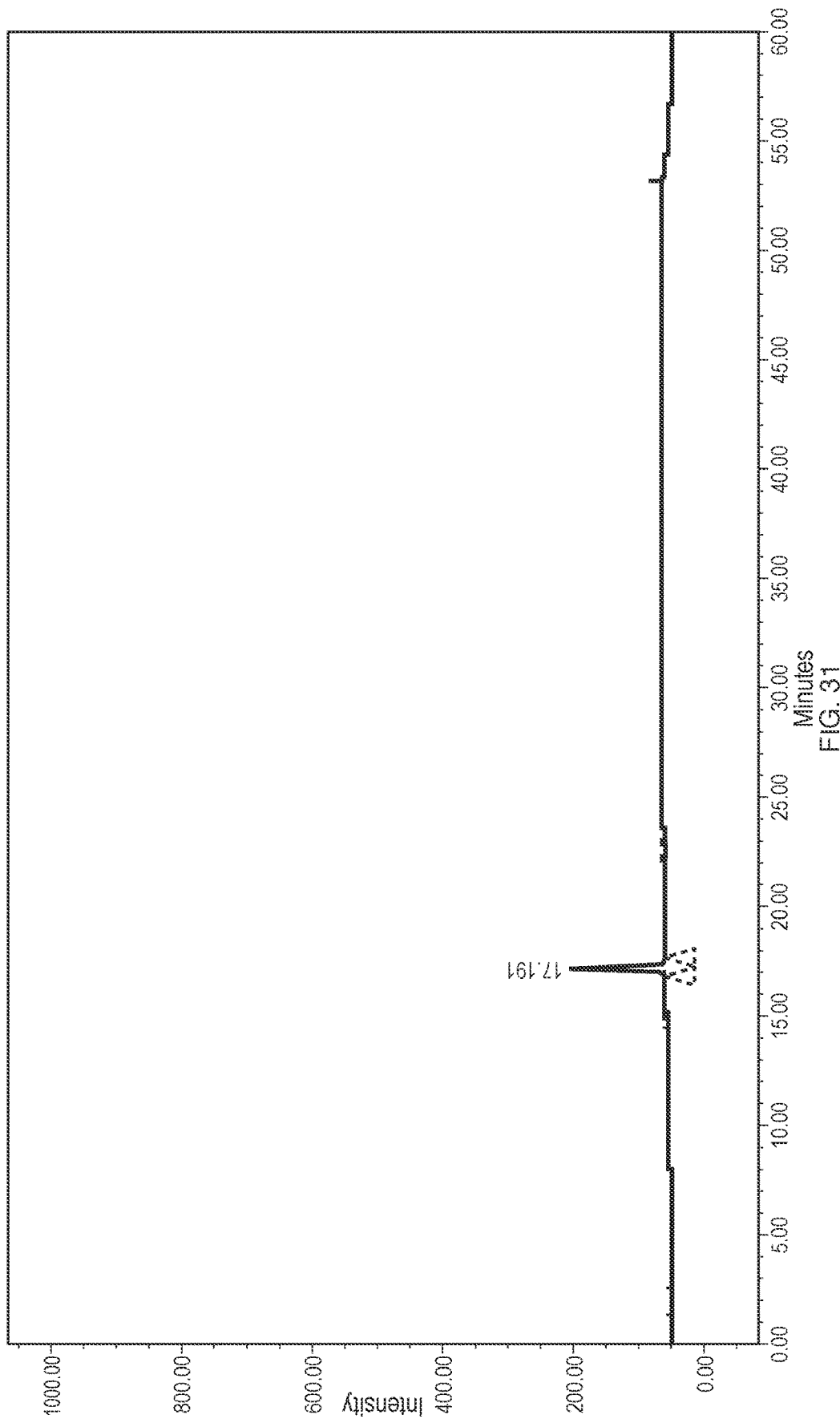
FIG. 31 illustrates a tocopherol chromatogram (UV).
Figure 32:
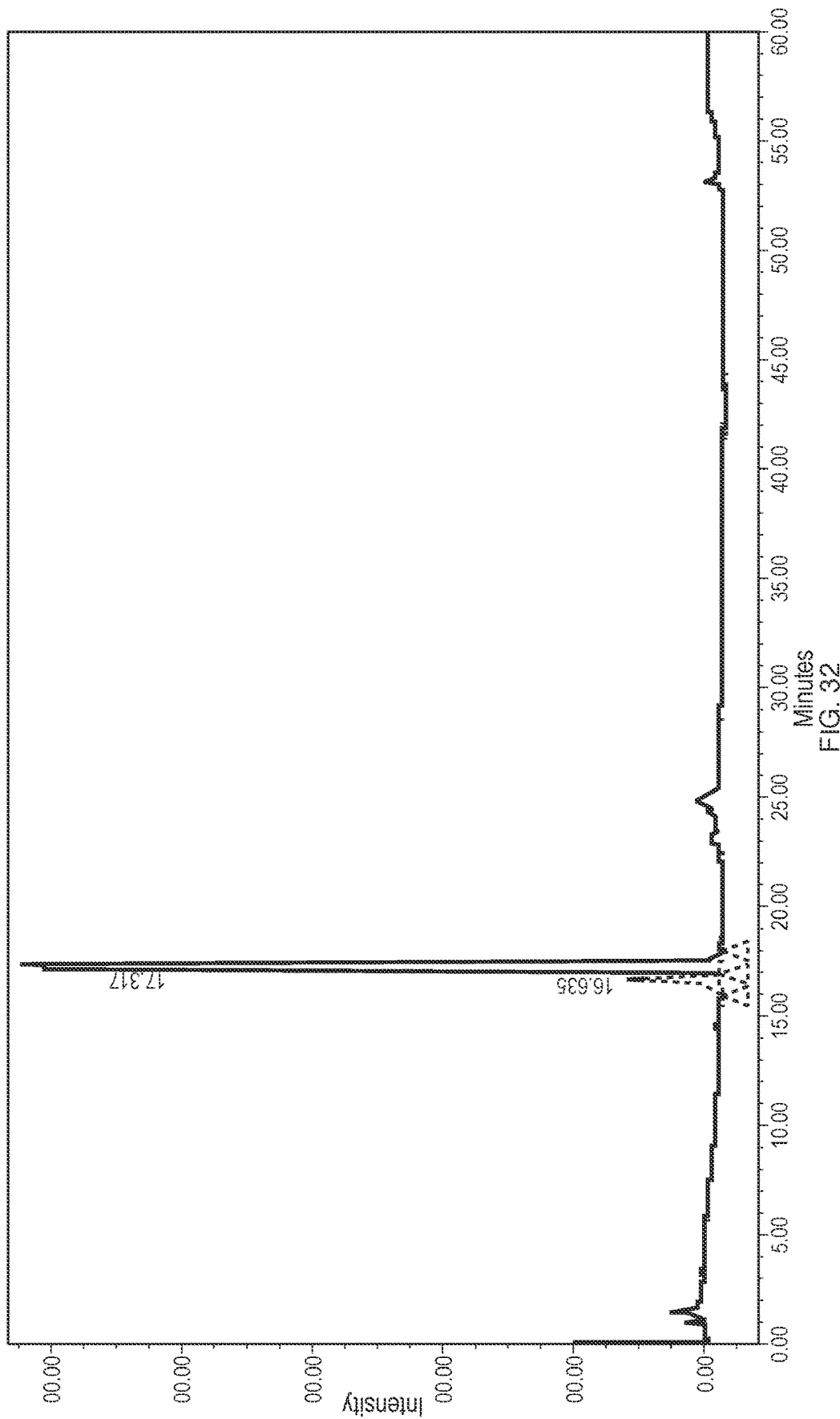
FIG. 32 illustrates a tocopherol chromatogram (CAD).
Figure 33:
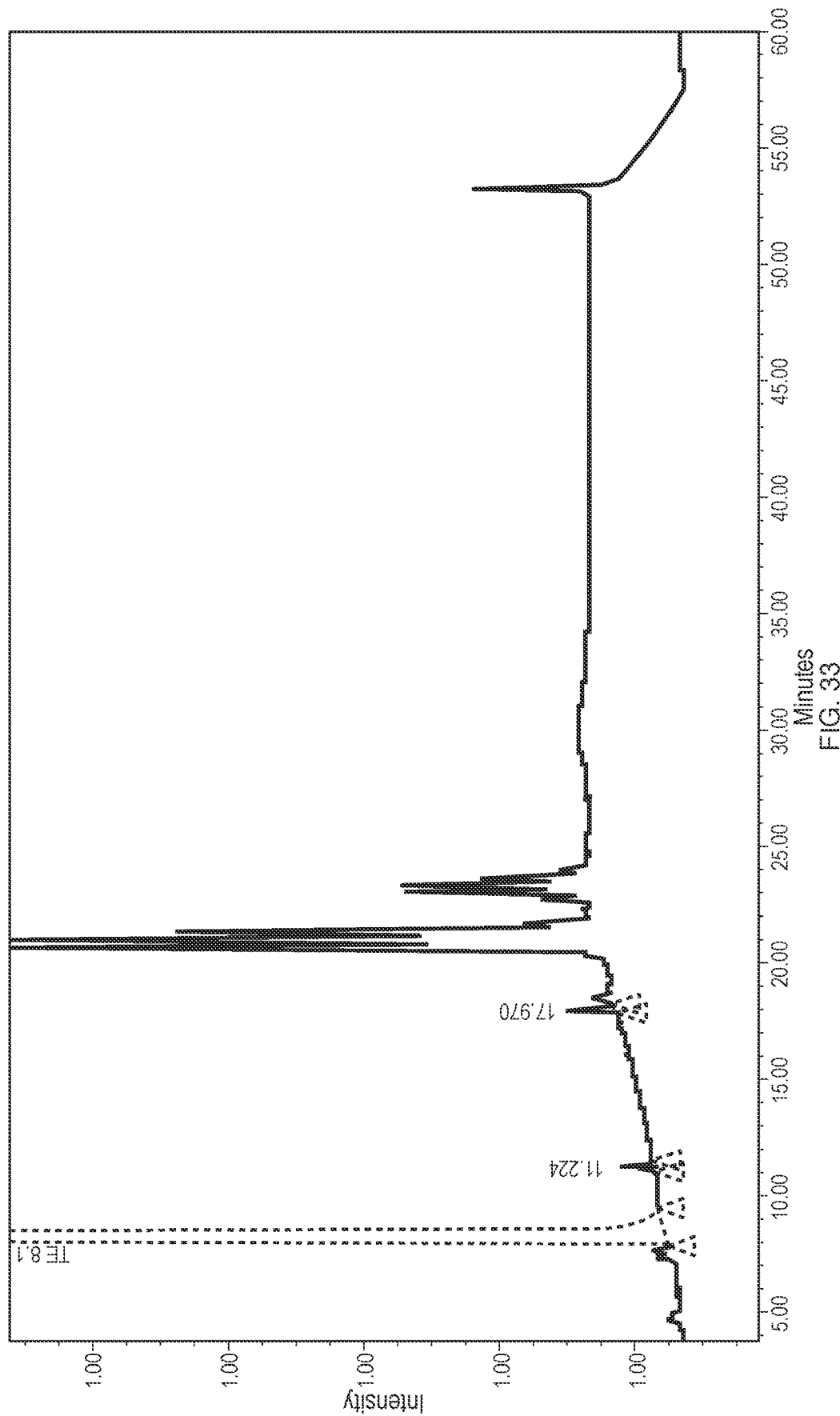
FIG. 33 illustrates a control sample chromatogram (UV 242 nm).
Figure 34:
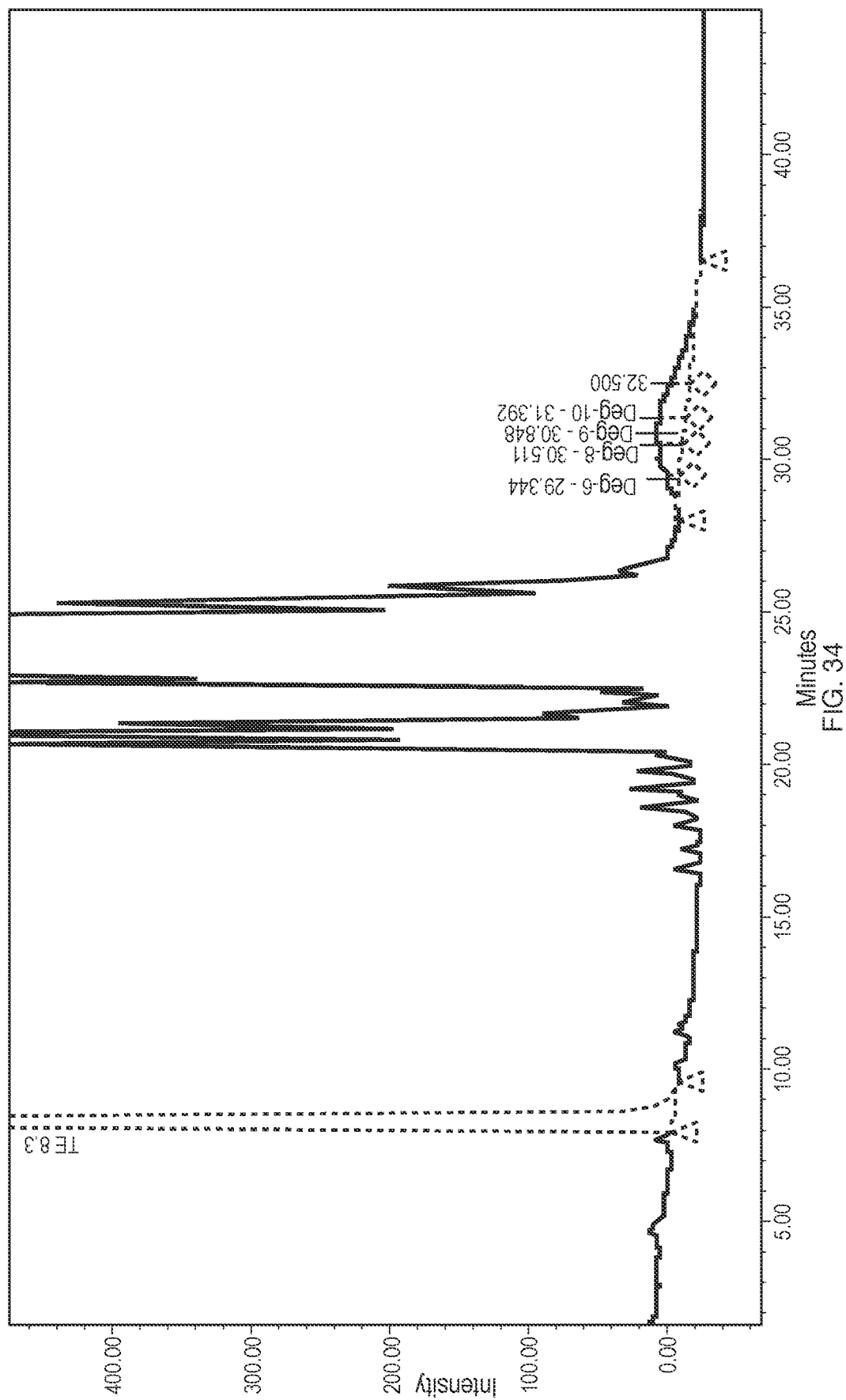
FIG. 34 illustrates a control sample chromatogram (CAD).
Figure 35:
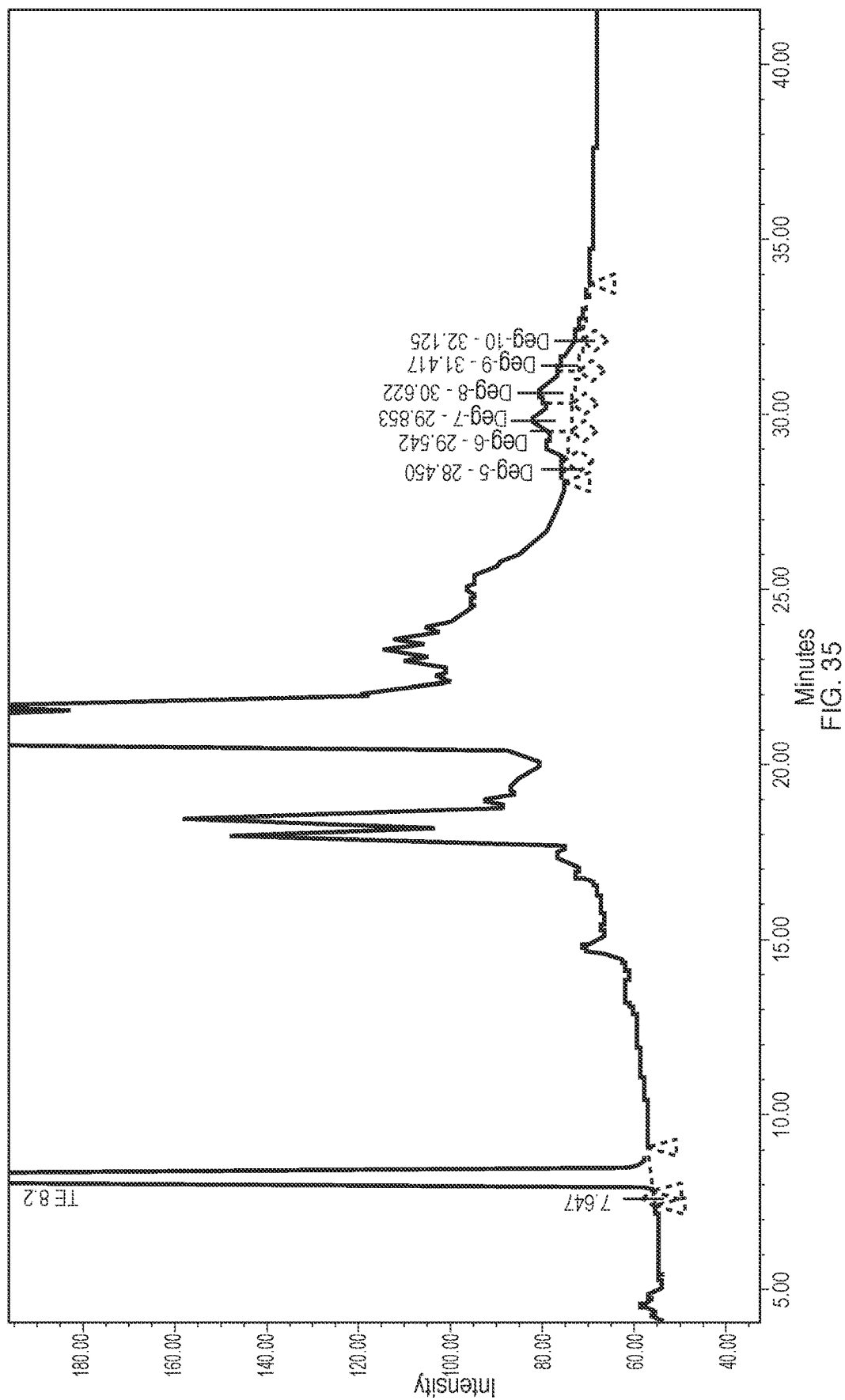
FIG. 35 illustrates a light exposed sample chromatogram (UV 242 nm).
Figure 36:
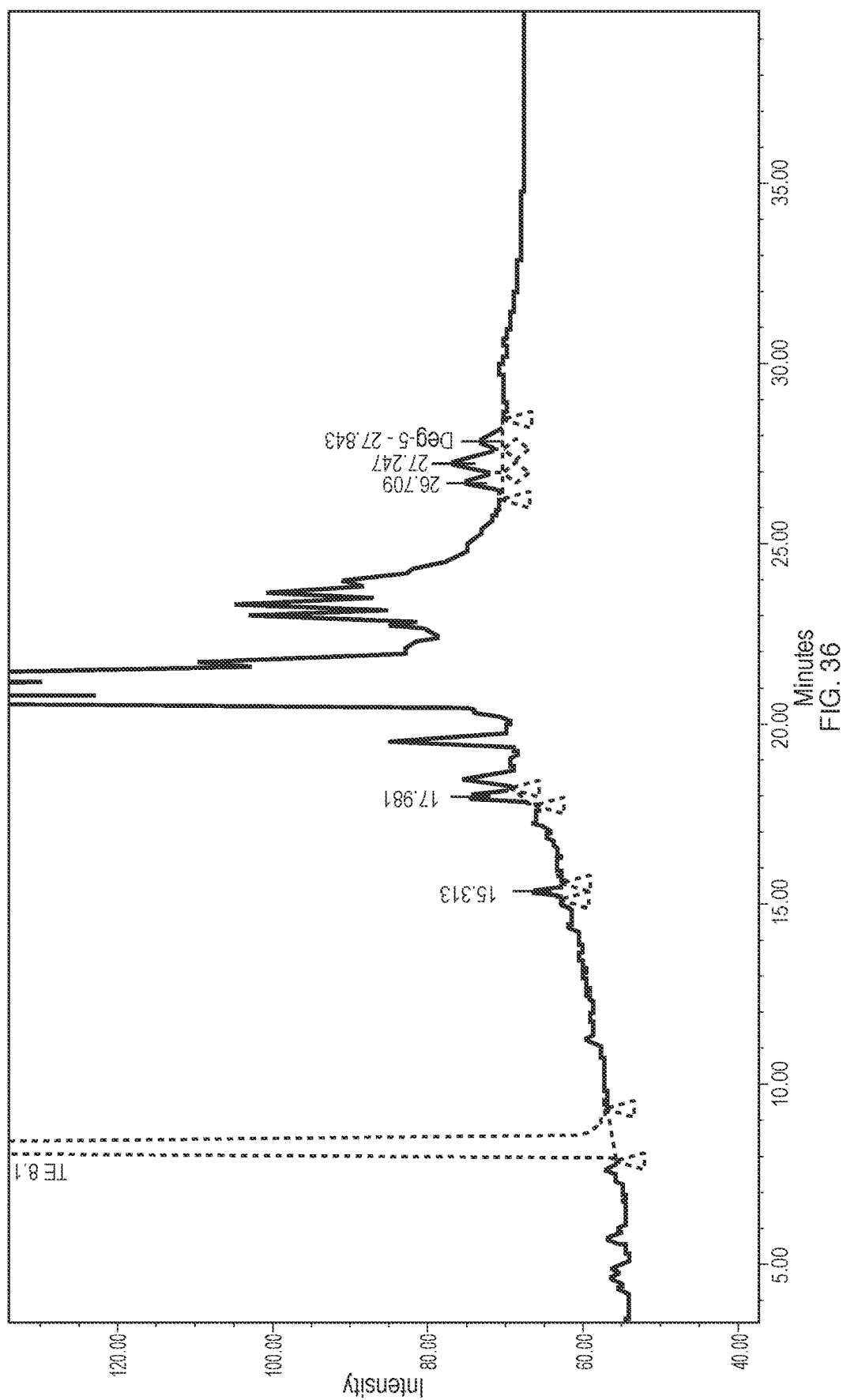
FIG. 36 illustrates a light exposed sample with tocopherol chromatogram (UV 242 nm).
Figure 37:
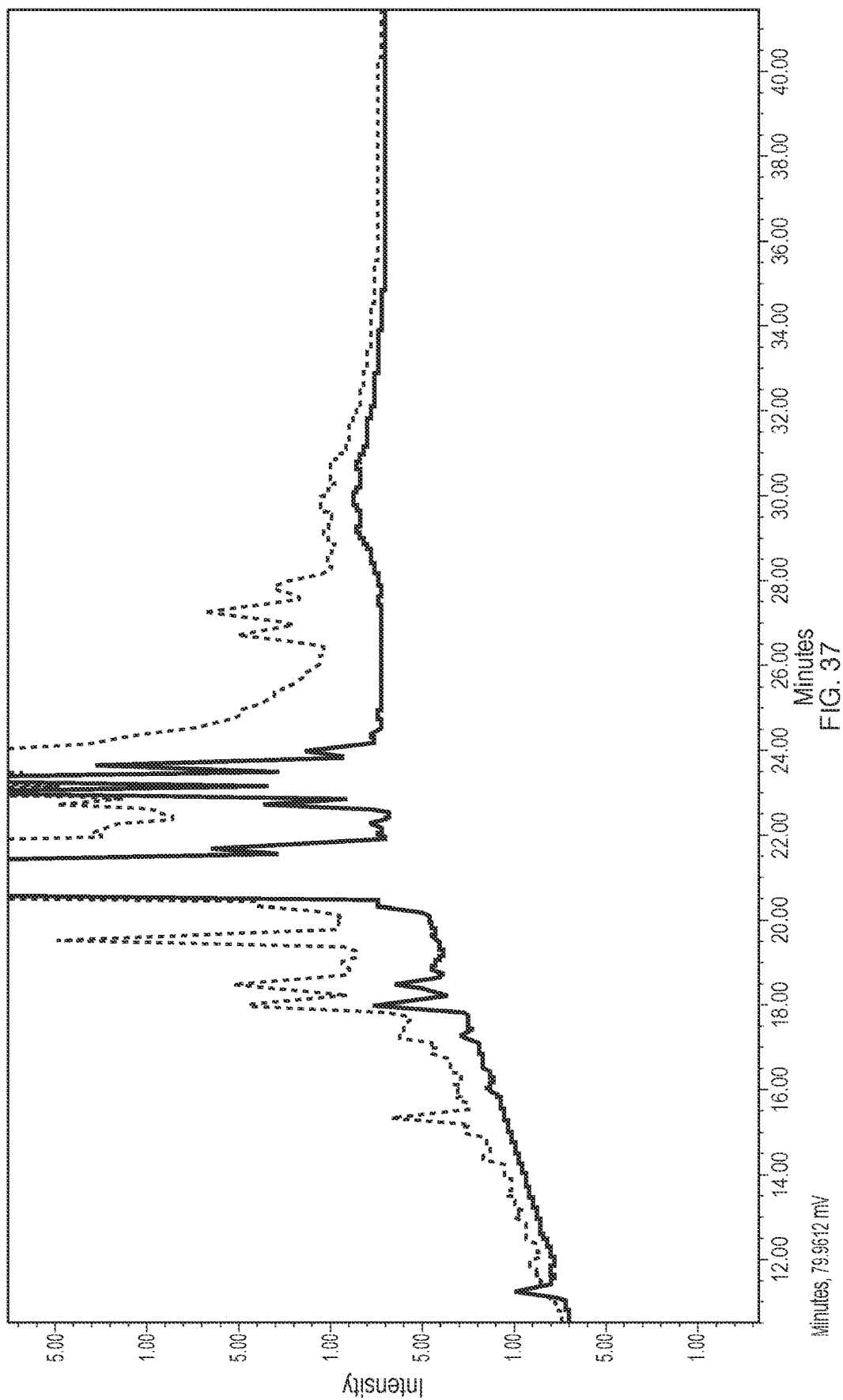
FIG. 37 illustrates superimposed chromatograms: control sample—black, sample with tocopherol—blue (242 nm).
Figure 38:
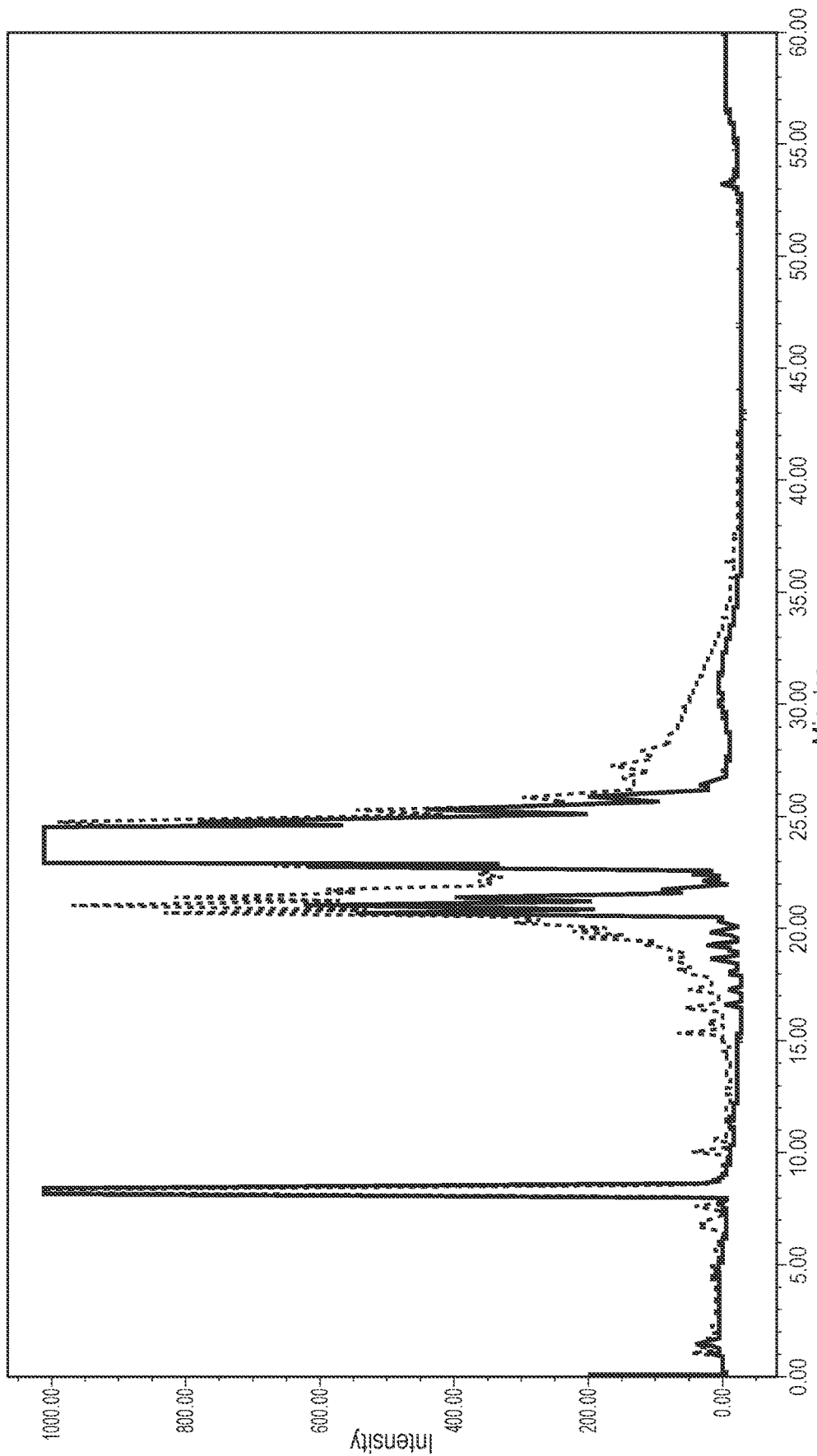
FIG. 38 illustrates superimposed chromatograms: control sample—black, sample with tocopherol—green (CAD).
Figure 39:
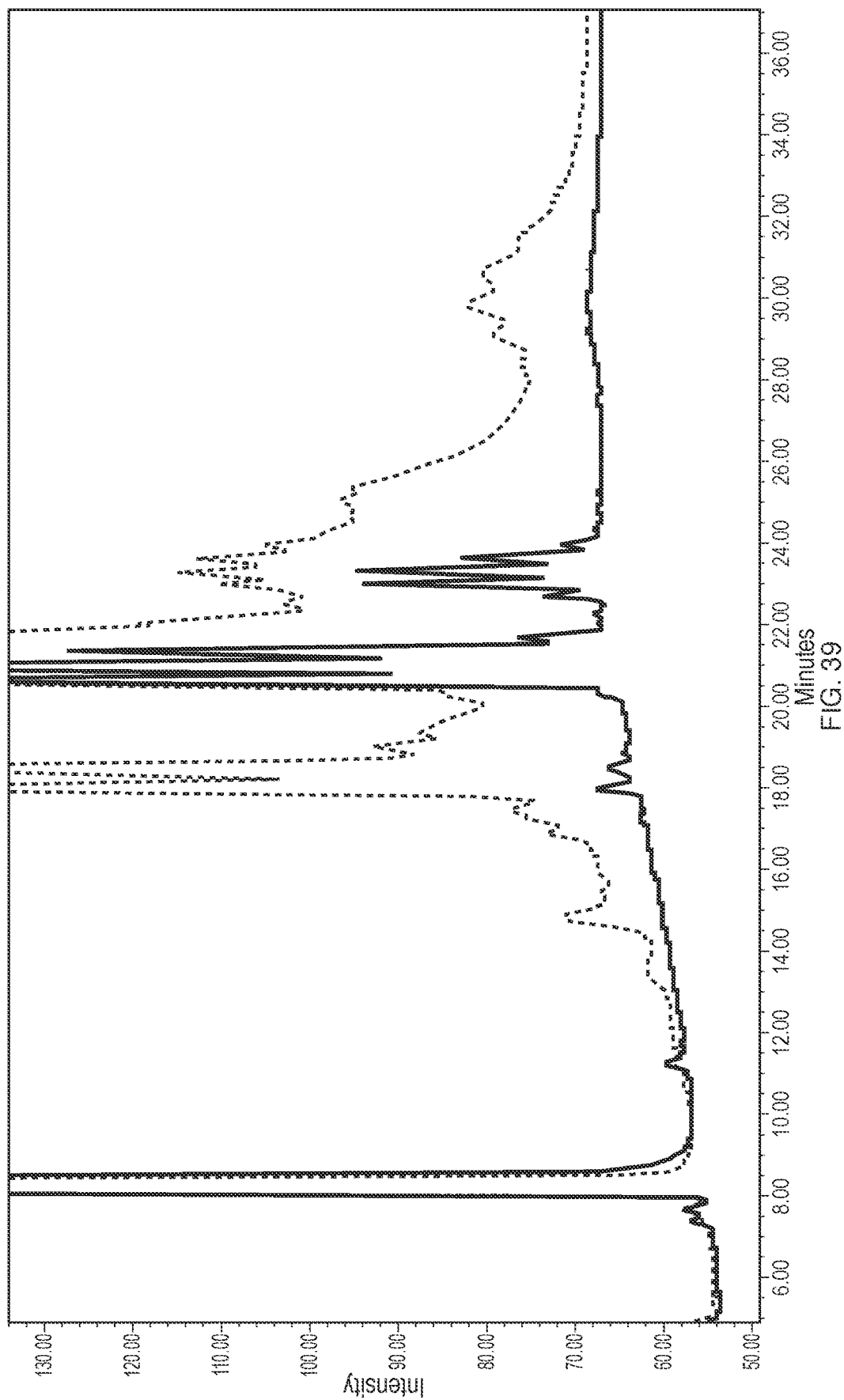
FIG. 39 illustrates superimposed chromatograms: light exposed sample—red, control sample—black (UV).
Figure 40:
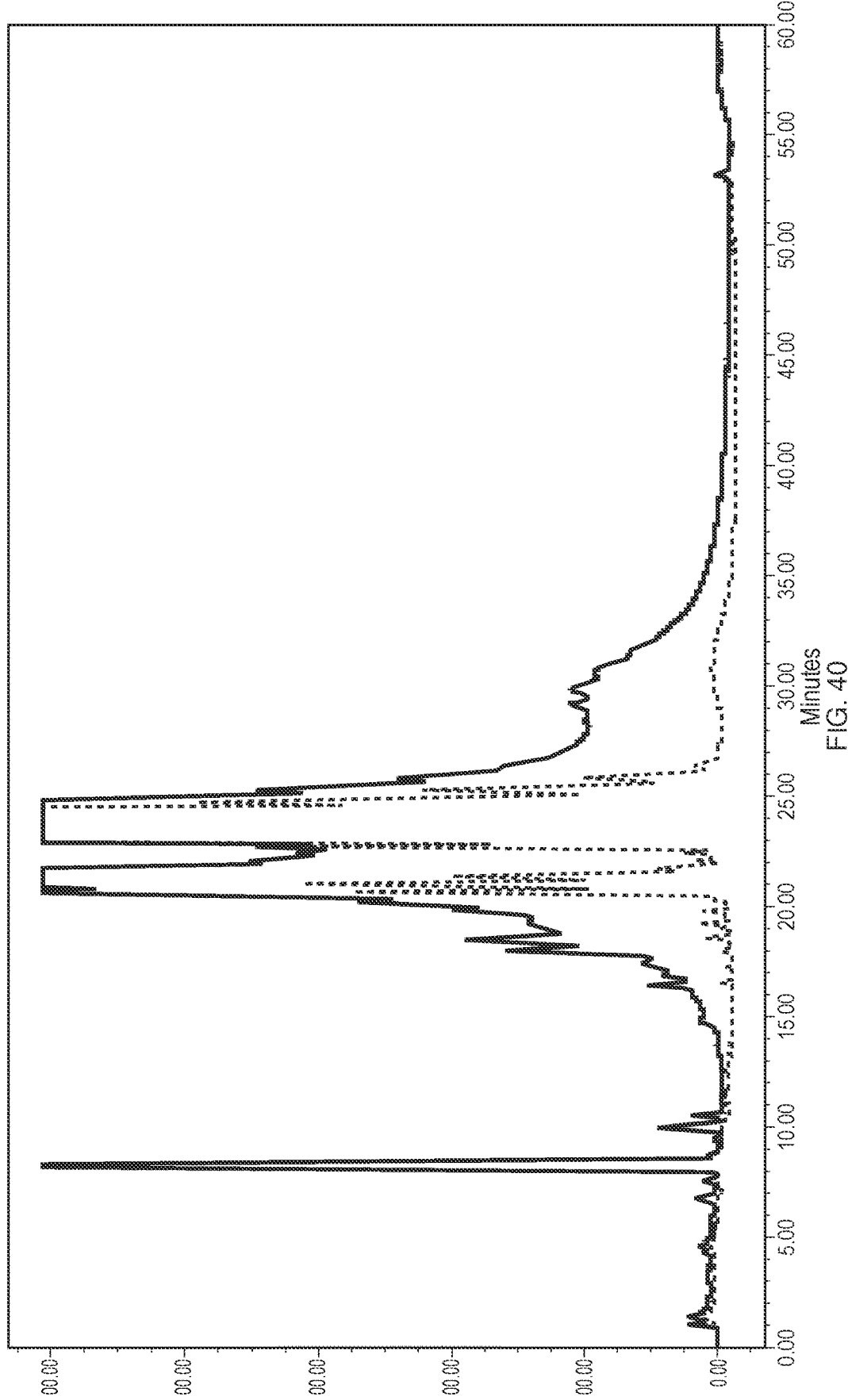
FIG. 40 illustrates superimposed chromatograms: light exposed sample—black, control sample—brown (CAD).
Figure 41:
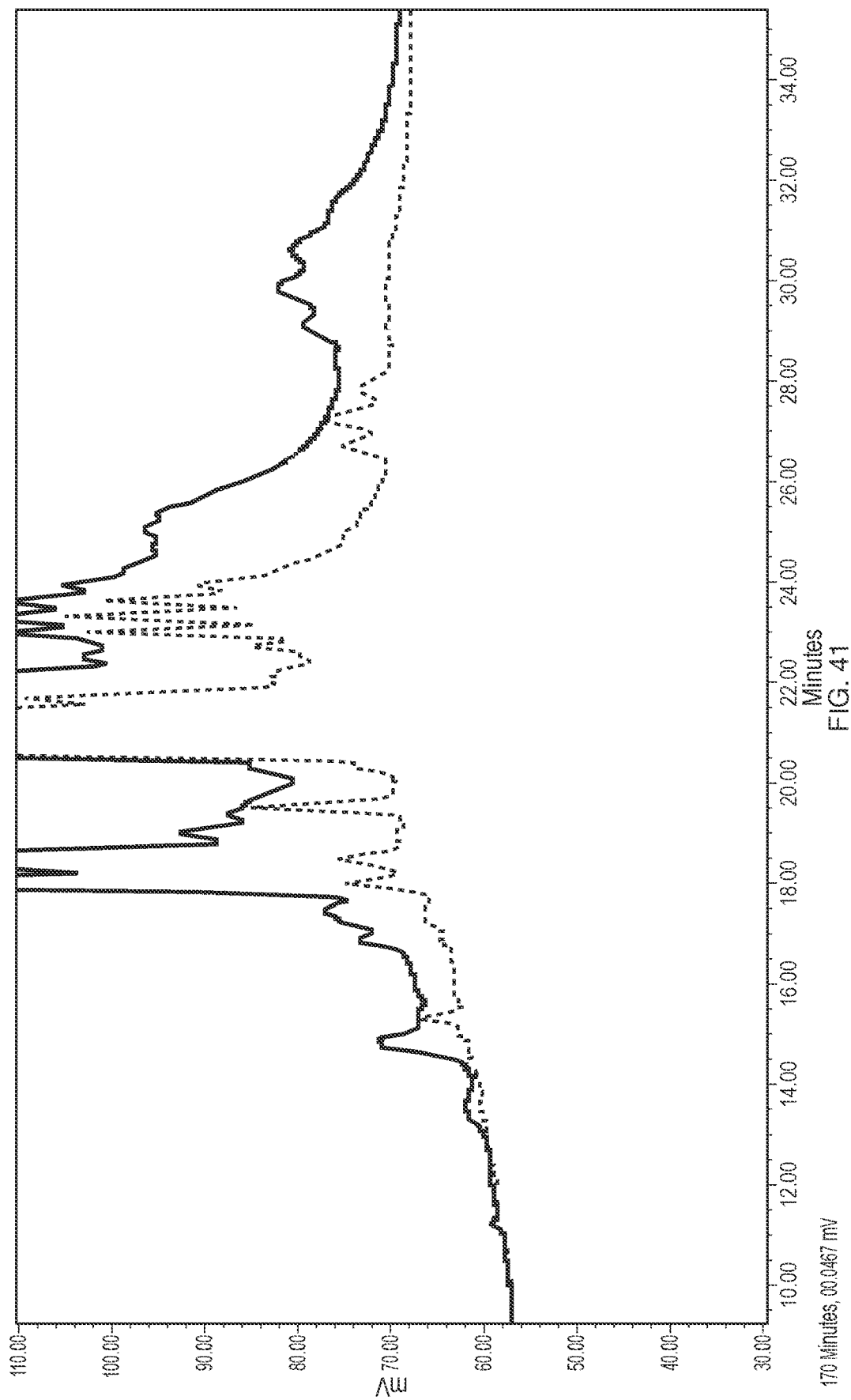
FIG. 41 illustrates superimposed chromatograms: light exposed sample—black, sample plus tocopherol—blue (UV).
Figure 42:
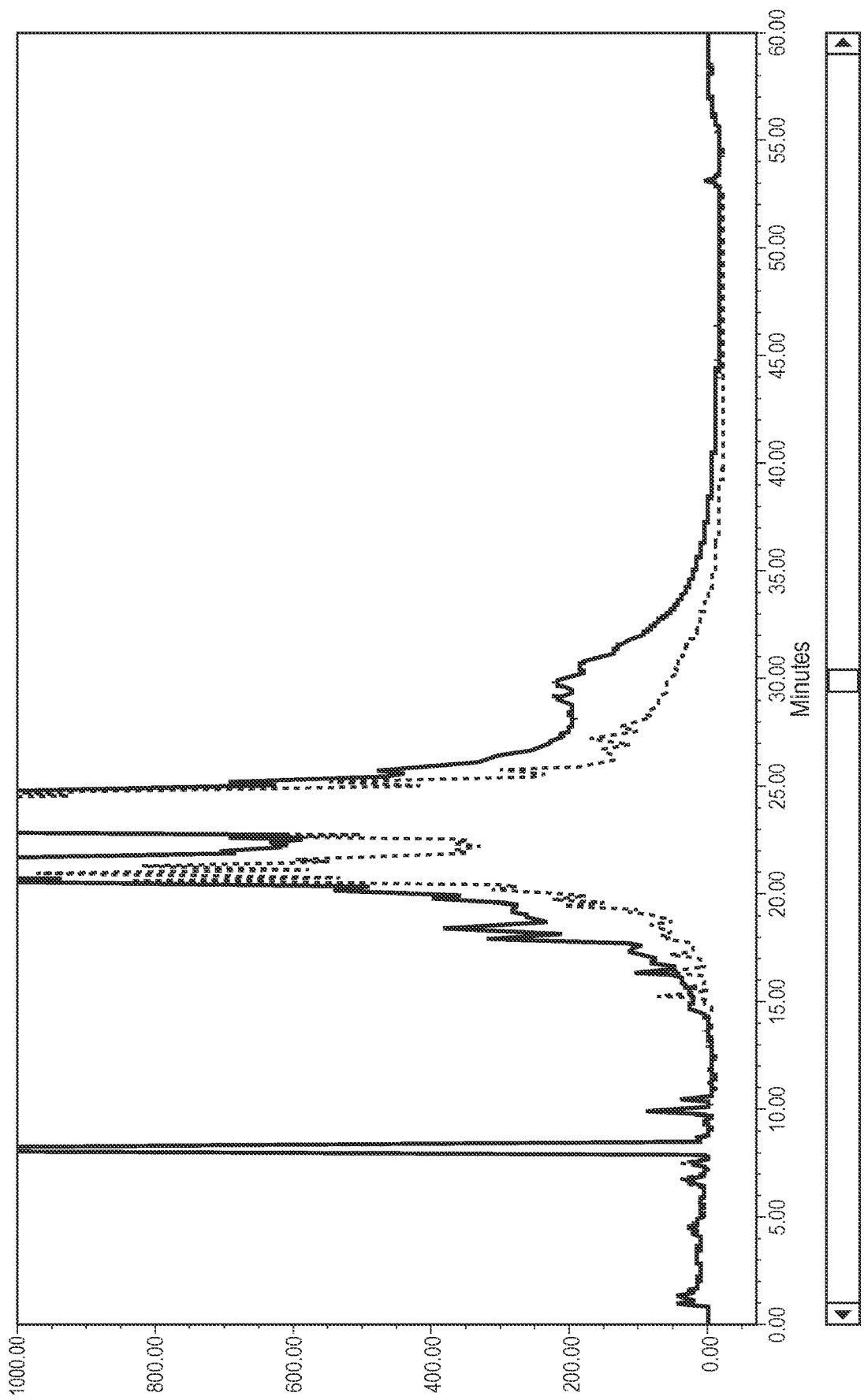
FIG. 42 illustrates superimposed chromatograms: light exposed sample—black, sample plus additive—green (CAD).
Figure 43:
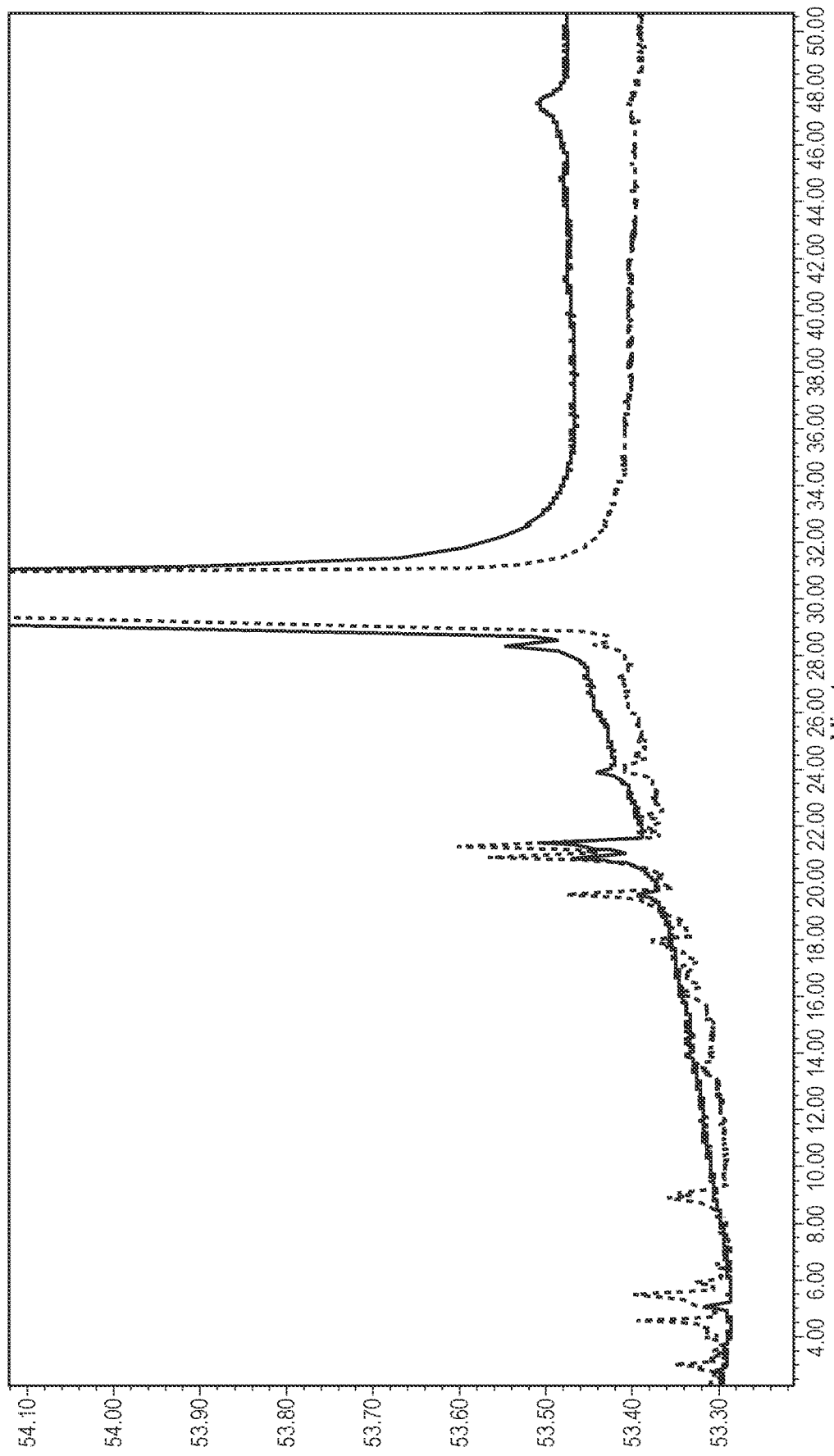
FIG. 43 illustrates superimposed chromatograms: control sample—black, light exposed sample—blue.
Figure 44:
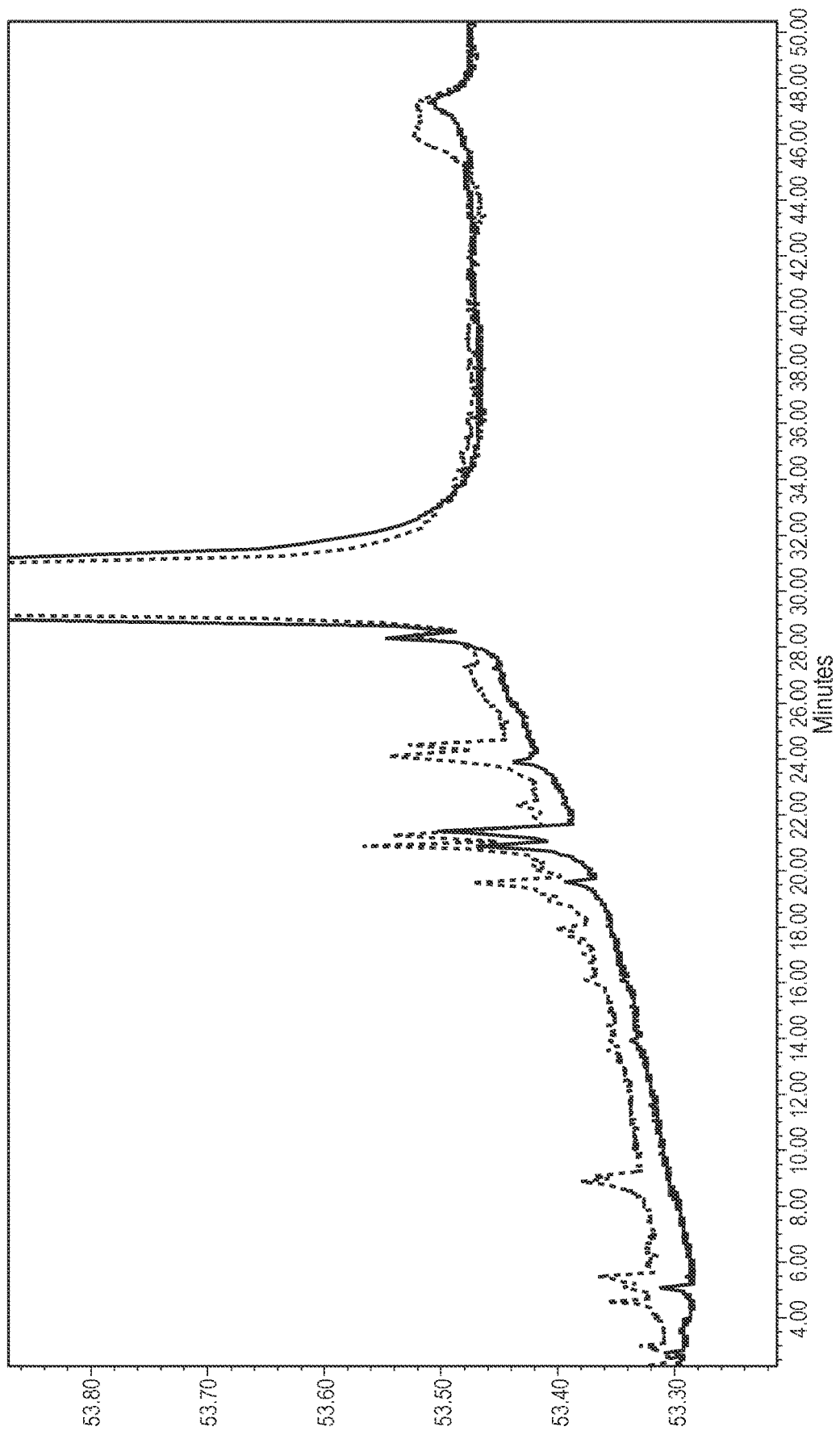
FIG. 44 superimposed chromatograms: control sample—black, sample plus tocopherol—green.
Figure 45:
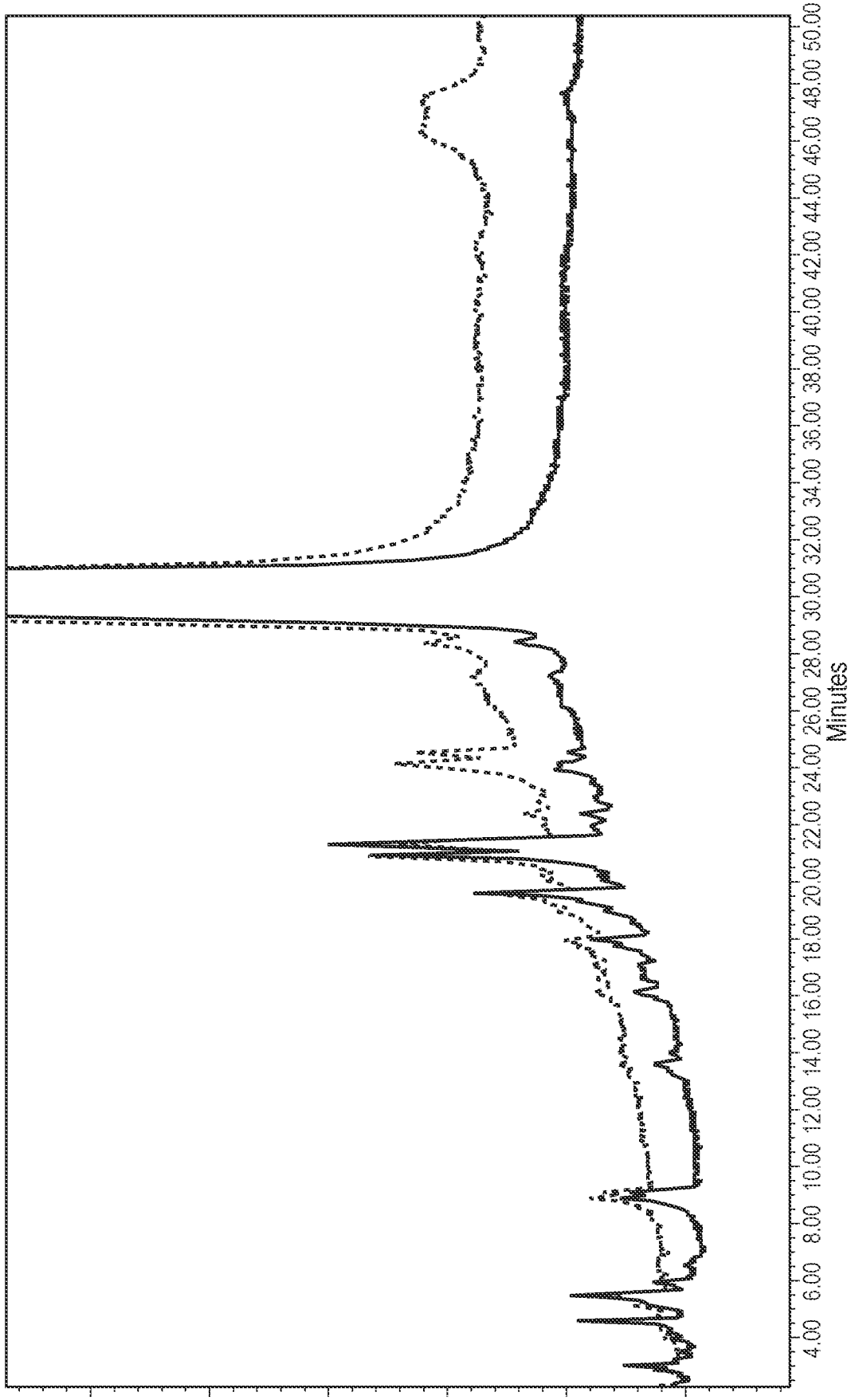
FIG. 45 superimposed chromatograms: control sample—black, sample plus tocopherol—green.
Figure 46:
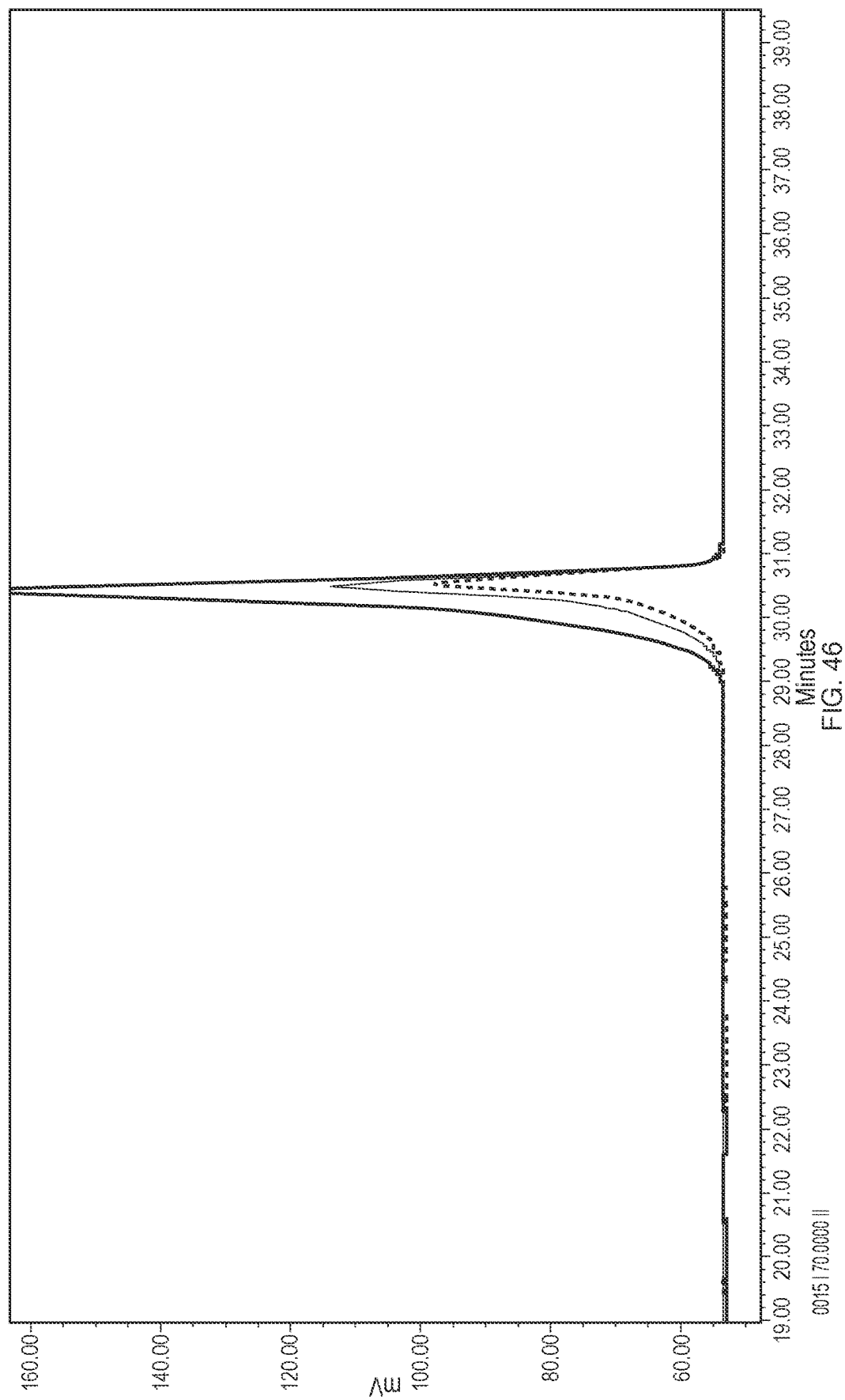
FIG. 46 superimposed chromatograms: TE Peak, control sample—black, sample plus tocopherol—green, sample—blue.

Example chromatograms of the TE Injection in unprotected prefilled syringe (PFS) exposed to the CH light conditions, and the Control (i.e., the same drug product sample not exposed to the ICH light conditions) are shown in FIG. 1 with UV detection at 242 nm, and FIG. 30 with Charged Aerosol Detection (CAD). In addition, both the light stress and control samples were chromatographed using the same conditions listed in Table 3, but with Mass Spectrometry (MS) detection. Peak identification for the peaks shown in FIGS. 1 and 30 based on the MS results are summarized in Table 4.

TABLE 4

Peak Identifications

| Retention Time (min) | Molecular Mass per MS | Identity |
|---|---|---|
| <8 | Not determined | Most likely not Testosterone related photo-degradants since they are seen in the Control |
| 8 | Not determined | Testosterone (TE) |
| 9-19 | 1226 (RT 16.5 min) 614 (RT 9.8 min) | Most likely not Testosterone related photo-degradants since they are seen in the Control |
| 19-21 | 886-916 ($M_{TG}$ + 32)[1] | Triglyceride Hydroperoxides (TGHP) |
| 22-23 | 855-885 ($M_{TG}$) | Triglycerides (TGs) |
| 22.5-24 | $M_{TG}$ + 400[2] | TE + TG adducts |
| | $M_{TG}$ + 2 × 400 | 2TE + TG adducts |
| 27-31 | 2 $M_{TG}$ | TG dimers[3] |

[1]TGs become TGHP by adding two oxygen atoms, thus the molecular mass increase by 32, where $M_{TG}$ is the molecular mass for TG.
[2]400 is the molecular mass for TE.
[3]Based on both MS and NMR.

The stability indicating capability of an HPLC method is often determined based on the peak purity of the active peak, and the mass balance, which is the sum of the assay and the total impurities. The peak purity of the main peak has previously been demonstrated, and detection of the photo-degradants using the method in Table 3 has not changed this assessment since the photo-degradants elute significantly later in the chromatogram. Using mass balance to assess the stability-indicating capability requires well characterized authentic impurity standards so that the relative response factors (RRFs) of the impurities can be determined and the majority of the impurities can be accurately quantitated.

Alternatively, the stability indicating capability of HPLC methods can be evaluated based on the inclusiveness of the chromatography and detection. The proposed HPLC method detects all photo-degradants since the gradient program ranged from a 70% ethanol/27% water/3% acetonitrile to 100% ethanol, which is capable of eluting not only the Drug Product, but also all hydrophobic sesame oil components including the TE-TG adducts. Additionally, universal detection (CAD and MS) was used to ensure that potential degradants with weak UV chromophore could be detected.

As described in Example 1, fractions at retention times (RT) 22.5 to 24 mins that corresponded to the TE+TG adducts were isolated by preparative HPLC, and two major TE-TG adducts were identified via MS and NMR, as TE-OLL and TE-OLL. The structures of these TE-TG adducts were deduced to form at the methylene group located vicinally between two homoconjugated double bonds (i.e., the C11 position) on the linoleoyl fatty acid side chain of TGs by reaction with the carbonyl group on the A-ring of TE, as shown in Scheme 1.

The TG composition of sesame oil per USP is shown in Table 5. Based on the photodegradation shown in Scheme 1, potential photo-degradants are adducts between TE with any TGs containing the linoleoyl fatty acid, i.e., TE-OLL, TE-OOL, TE-LLL, TE-POL, TE-PLL and TE-SOL, with TE-OLL and TE-OOL being the predominant degradants since these are the two major TG components reported in sesame oil. Other degradants may also include adducts between two TE molecules and one TG molecule containing two linoleoyl fatty acid chains, or adducts between three TE molecules and one TG molecule containing three linoleoyl fatty acid chains.

TABLE 5

Triglyceride Composition in Sesame Oil

| Triglyceride | USP Limit |
|---|---|
| OLL | 13.0-30.0 |
| OOL | 14.0-25.0 |
| LLL | 7.0-19.0 |
| POL | 8.0-16.0 |
| OOO | 5.0-14.0 |
| PLL | 5.0-9.0 |
| SOL | 2.0-8.0 |
| POO | 2.0-8.0 |

Preliminary to TE-TG adducts chromatographic separation, a limit test LC-MS method has been developed to selectively estimate the two major degradants, i.e., TE-OLL and TE-OOL. The chromatographic conditions shown in Table 1 were adopted with some minor modifications needed for the MS detection for the new LC-MS method.

Example 3: The Effect of Antioxidants on the Photo-Degradation of Testosterone Ester Triglycerides Formulations Sesame oil is the vehicle of Xyosted Testosterone Enanthate (TE) Injection drug product. Sesame oil is composed of various Triglycerides (TGs), and the TG composition of the United States Pharmacopeia (USP) grade sesame oil is shown in Table 5. TGs with the side chains containing the homoconjugated double bonds, such as the linoleoyl side chain, are labile to autoxidation in the presence of oxygen, or light and oxygen. The autoxidation of the linoleoyl side chain generates a linoleoyl hydroperoxide, along with a linoleoyl free radical, and a linoleoyl peroxy radical, as shown in Scheme 5. Because the linoleoyl free radical, and the linoleoyl peroxy radical are reactive, the autoxidation is an autocatalytic chain reaction.

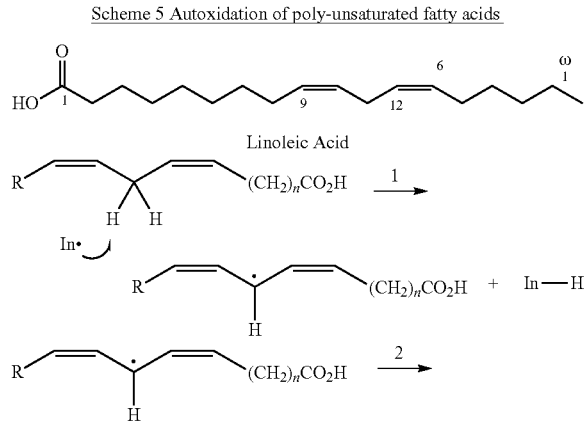

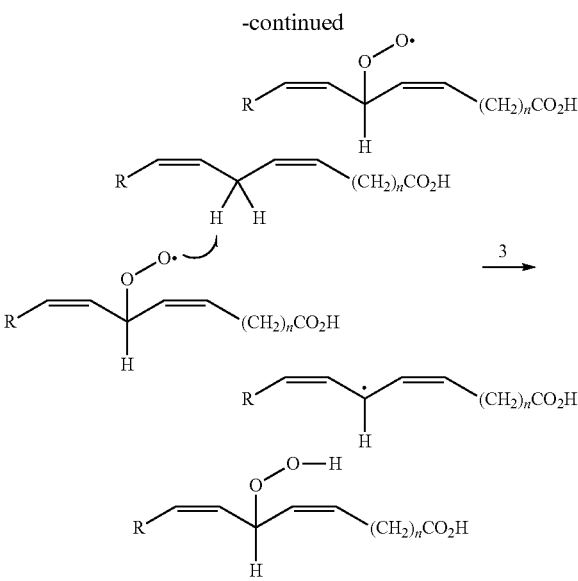

In Scheme 5, "In" represents any species that initiates the chain reaction, which can be $O_2$ or light. Note that the linoleic acid free radical formed in step 1 is doubly allylic. Once formed, the radical reacts with molecular oxygen in step 2 to produce a linoleic peroxy radical which abstracts a hydrogen atom from another linoleic acid molecule in step 3, which produces a hydroperoxide of linoleic acid and a new linoleic acid free radical, thereby propagating the chain reaction. The extent of oxidation of TGs can be measured by a USP test called the Peroxide Value (PV). The peroxide value is defined as the amount of peroxide oxygen per 1 kilogram of fat or oil (milli-eqivalent of $O_2$/kg of oil). As shown in Table 6, the PV of the Xyosted drug product increased over time, indicating that sesame oil (or TGs) in the drug product was oxidized over time.

TABLE 6

Stability Results of Peroxide Value of Xyosted with and without BHT

| Strength mg/0.5 mL | Batch Number | % BHT | Peroxide Value (milli-equivalent/Kg oil) Duration at 25° C./60% RH (month) | | | | | | |
|---|---|---|---|---|---|---|---|---|---|
| | | | Initial | 3 | 6 | 9 | 12 | 15 | 18 | 24 |
| 50 | 16HH0032 | 0 | 7.0 | 16.8 | 23.3 | 35.3 | 37.5 | 42.9 | 49.0 | 73.8 |
| | 16HH0033 | | 6.7 | 15.9 | 22.0 | 34.0 | 36.2 | 46.3 | 46.8 | 70.7 |
| | 16HH0034 | | 6.5 | 12.5 | 23.1 | 36.0 | 38.0 | 47.3 | 48.5 | 70.0 |
| 75 | 16HH0094 | | 7.2 | 14.3 | 21.5 | 35.7 | 38.8 | 41.6 | 55.5 | 73.8 |
| 100 | 16HI0002 | | 7.6 | 15.7 | 24.2 | 35.6 | 42.7 | 50.1 | 54.7 | 65.8 |
| | 16HI0003 | | 8.4 | 10.4 | 26.7 | 38.9 | 41.6 | 49.1 | 58.1 | 80.3 |
| | 16HI0004 | | 7.6 | 17.3 | 26.1 | 41.2 | 44.7 | 54.5 | 56.7 | 84.4 |
| 50 | TE3-140-1 | 0.07[1] | 2 | 4 | 4.6 | 4.6 | 6.2 | NT[2] | 7.2 | 8.4 |
| 100 | TE3-140-2 | 0.06[1] | 5.3 | 6.3 | 7.3 | 7.7 | 8.7 | NT | 11.1 | 11.7 |

[1]Prepared in sesame oil containing 750-1000 ppm of BHT

[2]NT = not tested

Butylated hydroxytoluene (BHT) is a known anti-oxidant, which acts as a free radical scavenger. It stops the autoxidation of TGs by donating a hydrogen atom to convert the peroxy radicals to the hydroperoxides and TG radicals to TGs, while generating a BHT radical, as shown in Scheme 6 (R* can be linoleoyl free radical, or linoleoyl peroxy radical).

Scheme 6 BHT is a Free Radical Scavenger

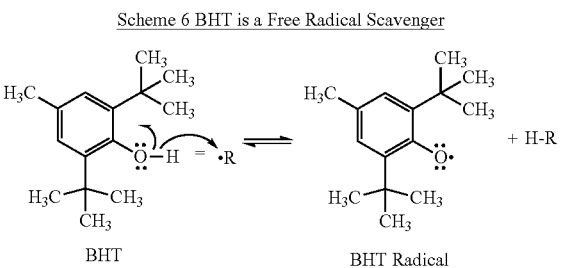

Once formed, the BHT radical cannot react further because the large tert-butyl groups create so much steric hindrance that the oxygen atom bearing the unpaired electron cannot make the required contact with other molecules to allow a reaction. Formation of the BHT radical stops radical chain reactions (e.g., the autoxidation in Scheme 5). As shown in Table 6, oxidation of sesame oil was effectively inhibited in the presence of 0.06-0.07% of BHT, as the PV level remained at a much lower level (i.e., <12), compared to the PV level of approximately 70-80 without BHT, when stored at 25° C./60% RH for 24 months.

Following exposure of the Drug Product to the ICH light conditions, i.e., including UV light exposure of not less than 200 watt/square meter and visible light exposure of not less than 1.2 million lux hours, the assay was decreased from 100% to 42.8% for the 50 mg/0.5 mL strength TE formulation, and from 100% to 63.4% for the 100 mg/0.5 mL strength TE formulation. The reduction indicates thus approximately 37-57% of total photo-degradation (Table 7). As shown in Table 7, however, photo-degradation was reduced by approximately 42% and 32% for the 50 mg/0.5 mL strength formulation, and the 100 mg/0.5 mL strength formulation, respectively, in the presence of 0.06-0.07% BHT.

TABLE 7

Assay per M10303 for TE PFS Exposed to 1 × ICH Light Conditions

| Batch Number | % BHT | Strength (mg/0.5 mL) | Assay (%) | ~Total Degradation (%) | % Degradation Reduction |
|---|---|---|---|---|---|
| 10404.001 | 0 | 50 | 42.8 | 57.2 | NA |
| 10403.002 | 0 | 100 | 63.4 | 36.6 | NA |
| TE-3-140-1 | ~0.07 | 50 | 66.8 | 33.2 | 42[(1)] |
| TE-3440-2 | ~0.06 | 100 | 75.0 | 25.0 | 32[(2)] |

[(1)]Compared to the results of the same strength = [(57.2%-33.2%)/57.2%] × 100
[(2)]Compared to the results of the same strength = [(36.6.2%-25.0%)/36.6%] × 100

Similar results were obtained using tocopherol as an antioxidant. Samples of 50 mg/0.5 mL were employed, with or without 10 µL of tocopherol, were exposed to 1×ICH light conditions (Table 8, FIGS. 31 to 46). Addition of ~2% of (±)-α-tocopherol in the drug product reduced the photo-degradation from ~62.3% to ~47.2% after exposure to 1×ICH light conditions.

TABLE 8

Effect of (±)-α-Tocopherol in Photo-degradation Reduction

| Sample[(1)] | % Assay | % Total Degradation[(2)] |
|---|---|---|
| Control-Unexposed Sample | 100.8 | Not applicable |
| Sample Exposed to 1 × ICH Light | 38.5 | ~62.3 |
| Sample with 2% Tocopherol[(3)] Exposed to 1 × ICH Light | 53.6 | ~47.2 |

[(1)]The 50 mg/0.5 mL strength formulation was used
[(2)]% Total Degradation = % Assay (Control) − % Assay (exposed sample)
[(3)]Approximately 10 µL of tocopherol was added to ~0.5 mL of Xyosted drug product, which is approximately 2% using the density of 950 Kg/m$^3$ of tocopherol While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

The invention claimed is:
1. A light stable testosterone ester pharmaceutical formulation for parenteral administration comprising a testosterone ester of Formula 1, a pharmaceutically acceptable carrier comprising a triglyceride of Formula 2, and a testosterone ester adduct of Formula 3:

Formula 1

Formula 2

Formula 3 wherein in Formula 1 and Formula 2:
$R_1$ is an alkyl or alkenyl substituent; and
each of $R_2$, $R_3$, and $R_4$ is an acyl group corresponding to a fatty acid selected from the group consisting of linoleic acid, oleic acid, palmitic acid, ricinoleic acid, linolenic acid, and stearic acid;
wherein in Formula 3:
$R_1$ is an alkyl or alkenyl substituent as defined in Formula 1;
$R_5$ is an acyl group corresponding to an unsaturated fatty acid;
G is a glycerol, or monoglyceride, or diglyceride residue;
n is 1, 2, or 3; and
the testosterone residue is connected to an allylic or doubly allylic carbon of $R_5$;
wherein the light stability of the pharmaceutical formulation is assessed a period of time after making the formulation by measuring a concentration of available testosterone ester and comparing it to an initial testosterone ester concentration in the pharmaceutical formulation, and by measuring a concentration of between 0.005 mg/ml and 25 mg/ml of the testosterone ester adduct of Formula 3.

2. The light stable testosterone ester pharmaceutical formulation of claim 1, wherein $R_1$ is selected from the group consisting of propyl, butyl, pentyl, hexyl, heptyl, octyl, nonyl, decyl, undecyl, dodecyl, cyclopentylethyl, and unsaturated analogs thereof.

3. The light stable testosterone ester pharmaceutical formulation of claim 1, wherein the testosterone ester is testosterone enanthate, testosterone cypionate, testosterone propionate, or testosterone undecanoate.

4. The light stable testosterone ester pharmaceutical formulation of claim 1, wherein the testosterone ester is testosterone enanthate.

5. The light stable testosterone ester pharmaceutical formulation of claim 1, wherein the triglyceride is selected from the group consisting of trilinolein (LLL), 1,2-dilinoleoyl-3-oleoyl-rac-glycerol (OLL), 1,2-dioleoyl-3-linoleoyl-rac-glycerol (OOL), triolein (OOO), 12-dilinoleoyl-3-palmitoyl-rac-glycerol (PLL), 1-palmitoyl-2-oleoyl-3-linoleoyl-rac-glycerol (POL), 1,2-dioleoyl-3-palmitoyl-rac-glycerol (POO), and 1-linoleoyl-2-oleoyl-3-stearoyl-rac-glycerol (SOL).

6. The light stable testosterone ester pharmaceutical formulation of claim 1, wherein the pharmaceutically acceptable carrier comprises a vegetable oil.

7. The light stable testosterone ester pharmaceutical formulation of claim 6, wherein the vegetable oil is sesame oil.

8. The light stable testosterone ester pharmaceutical formulation of claim 1, further comprising an antioxidant selected from the group consisting of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and glutamate monosodium.

9. The light stable testosterone ester pharmaceutical formulation of claim 8, wherein the testosterone ester is testosterone enanthate, the pharmaceutically acceptable carrier comprises sesame oil, and the antioxidant is BHT.

10. The light stable testosterone ester pharmaceutical formulation of claim 1, wherein the concentration of the testosterone ester ranges from 50 mg/mL to 200 mg/mL.

11. The light stable testosterone ester pharmaceutical formulation of claim 8, wherein the concentration of the antioxidant ranges from 0.01% to 0.1%.

12. The light stable testosterone ester pharmaceutical formulation of claim 8, wherein the concentration of the antioxidant ranges from 0.1 mg/mL to 1 mg/mL.

13. The light stable testosterone ester pharmaceutical formulation of claim 1, the testosterone ester adduct having any one of Formulas 4-11:

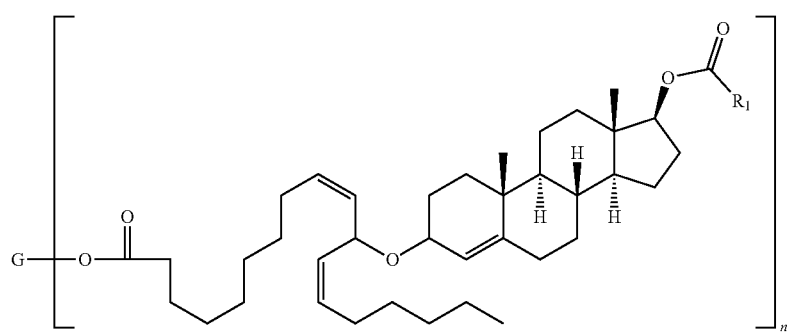

Formula 4

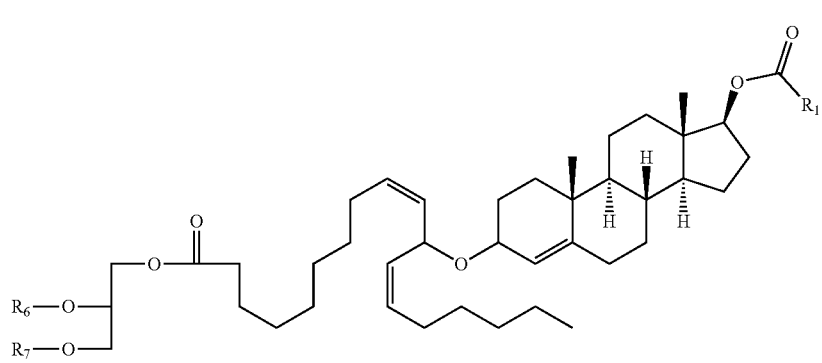

Formula 5

Formula 6
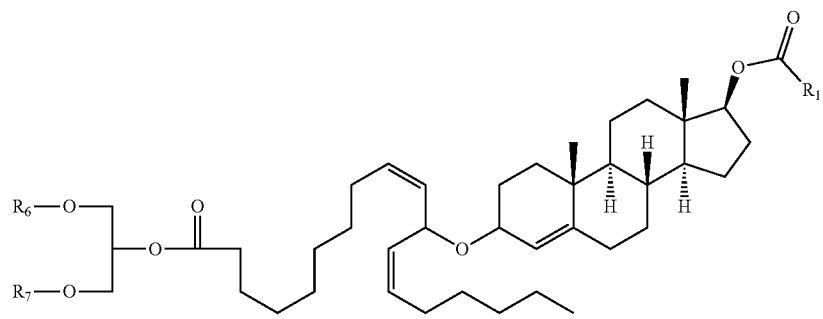
Formula 7
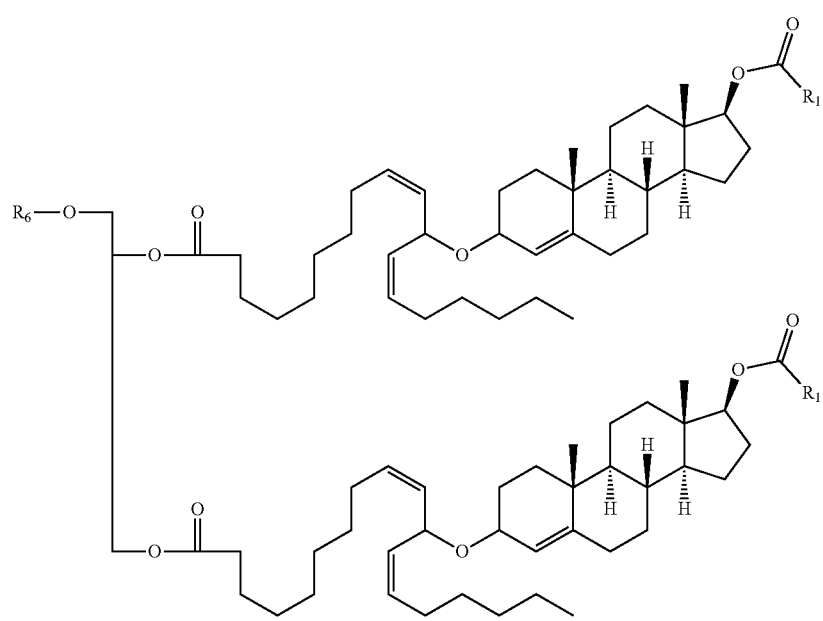
Formula 8
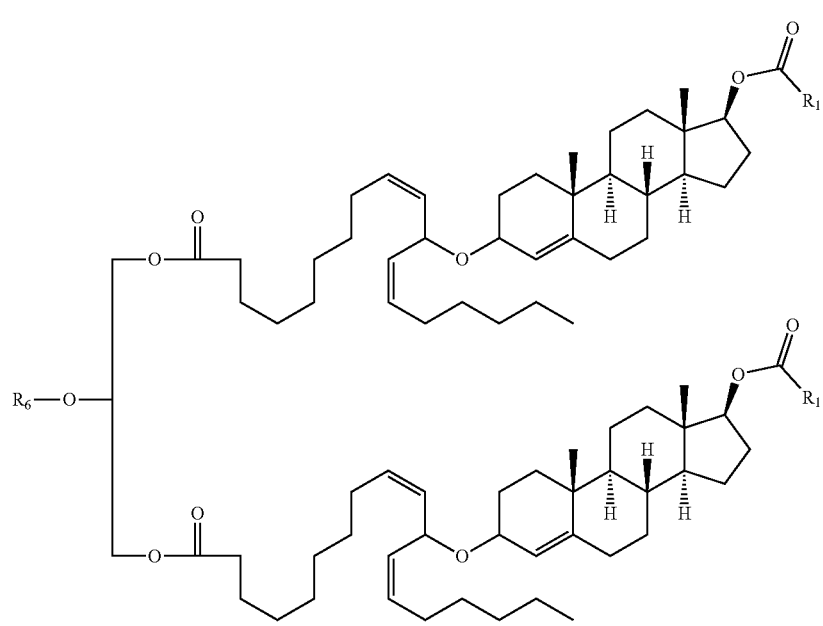

Formula 9
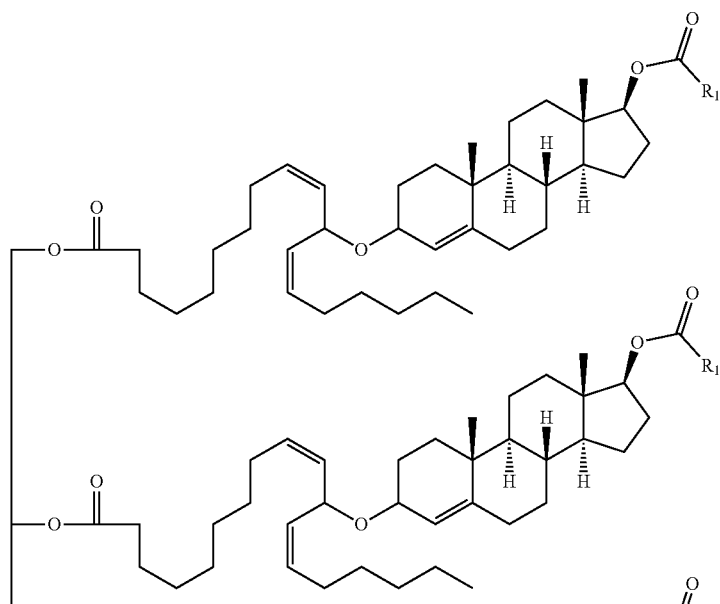
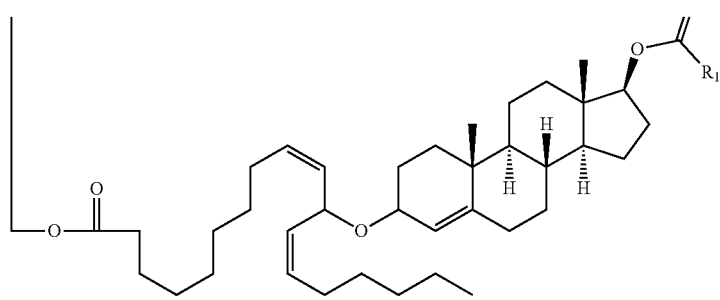
Formula 10
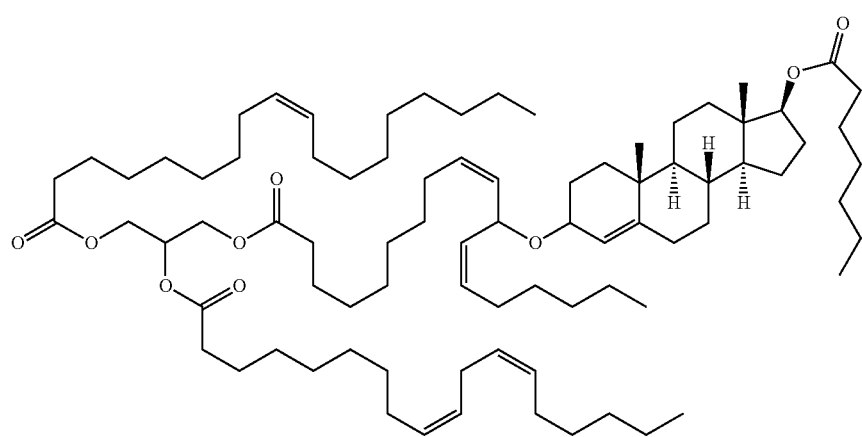

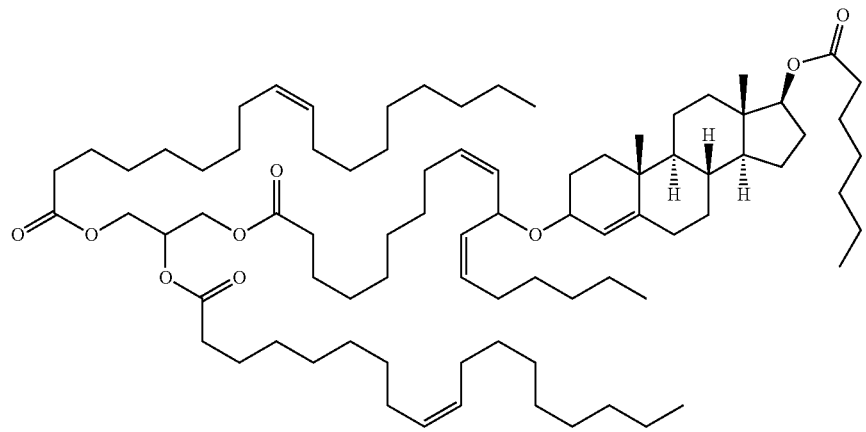

Formula 11 wherein each one of $R_6$ and $R_7$ is independently an acyl group corresponding to a fatty acid selected from the group consisting of linoleic acid, oleic acid, palmitic acid, ricinoleic acid, linolenic acid, and stearic acid.

14. The light stable testosterone ester pharmaceutical formulation of claim 1, further comprising an antioxidant, wherein the testosterone ester is testosterone enanthate, the triglyceride is selected from the group consisting of trilinolein (LLL), 1,2-dilinoleoyl-3-oleoyl-rac-glycerol (OLL), 1,2-dioleoyl-3-linoleoyl-rac-glycerol (OOL), triolein (OOO), 12-dilinoleoyl-3-palmitoyl-rac-glycerol (PLL), 1-palmitoyl-2-oleoyl-3-linoleoyl-rac-glycerol (POL), 1,2-dioleoyl-3-palmitoyl-rac-glycerol (POO), and 1-linoleoyl-2-oleoyl-3-stearoyl-rac-glycerol (SOL), and the pharmaceutically acceptable carrier comprises a vegetable oil.

15. The light stable testosterone ester pharmaceutical formulation of claim 14, wherein the antioxidant is selected from the group consisting of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and glutamate monosodium.

16. The light stable testosterone ester pharmaceutical formulation of claim 14, wherein the pharmaceutically acceptable carrier comprises sesame oil, the antioxidant is BHT, and the testosterone ester adduct has Formula 11:

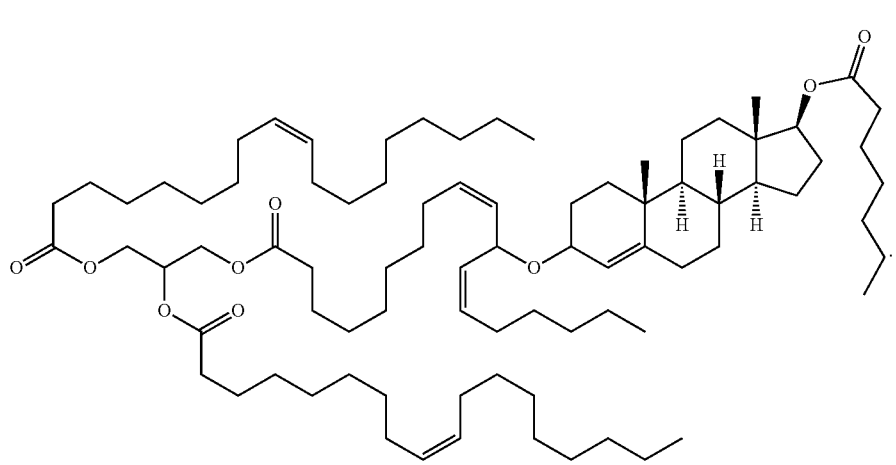

Formula 11

* * * * *